United States Patent
Belohlavek et al.

(10) Patent No.: US 11,123,141 B2
(45) Date of Patent: Sep. 21, 2021

(54) SYSTEMS AND METHODS FOR NAVIGATING A CATHETER AND DELIVERING A NEEDLE

(71) Applicant: MAYO Foundation for Medical Education and Research, Rochester, MN (US)

(72) Inventors: Marek Belohlavek, Scottsdale, AZ (US); Eileen M. McMahon, Cocoa, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 823 days.

(21) Appl. No.: 15/136,064

(22) Filed: Apr. 22, 2016

(65) Prior Publication Data

US 2016/0235485 A1 Aug. 18, 2016

Related U.S. Application Data

(63) Continuation-in-part of application No. 13/816,796, filed as application No. PCT/US2011/047711 on Aug. 15, 2011, now abandoned.

(Continued)

(51) Int. Cl.
*A61B 34/20* (2016.01)
*A61M 25/01* (2006.01)
(Continued)

(52) U.S. Cl.
CPC ............ *A61B 34/20* (2016.02); *A61B 8/0841* (2013.01); *A61B 8/0883* (2013.01); *A61B 8/12* (2013.01);
(Continued)

(58) Field of Classification Search
CPC ......... A61B 34/20; A61B 8/12; A61B 8/0883; A61B 8/0841; A61B 2090/3929;
(Continued)

(56) References Cited

U.S. PATENT DOCUMENTS 4,217,684 A 8/1980 Brisken et al.
4,425,525 A 1/1984 Smith et al.
(Continued)

FOREIGN PATENT DOCUMENTS

FR 2716266 A1 8/1995

OTHER PUBLICATIONS

Jensen JA (1991). "A model for the propagation and scattering of ultrasound in tissue." J Acoust Soc Am 89:182-90.
(Continued)

*Primary Examiner* — Sanjay Cattungal
(74) *Attorney, Agent, or Firm* — Quarles & Brady LLP

(57) ABSTRACT

Systems and methods for navigating a catheter and delivering a needle to a desired anatomic location are provided. The system includes an injection catheter that includes a needle slidably exposed from, or retracted into, the catheter lumen. The system further includes a first acoustic marker located at a distal end of the catheter and configured to generate an acoustic signal, and a second acoustic marker located at the distal end of the retractable needle and configured to generate an acoustic signal. The acoustic markers allow, in conjunction with a Doppler ultrasound imaging system, identification and navigation of an injection catheter and delivering a needle to a desired anatomic target location.

33 Claims, 34 Drawing Sheets

Related U.S. Application Data

(60) Provisional application No. 61/375,093, filed on Aug. 19, 2010, provisional application No. 62/166,942, filed on May 27, 2015.

(51) Int. Cl.
*A61B 8/08* (2006.01)
*A61M 5/158* (2006.01)
*A61B 8/12* (2006.01)
*A61M 25/00* (2006.01)
*A61B 8/00* (2006.01)
*A61B 90/00* (2016.01)

(52) U.S. Cl.
CPC ........ *A61M 5/158* (2013.01); *A61M 25/0108* (2013.01); *A61B 8/461* (2013.01); *A61B 8/488* (2013.01); *A61B 2034/2063* (2016.02); *A61B 2090/3929* (2016.02); *A61M 25/0084* (2013.01); *A61M 2005/1588* (2013.01)

(58) Field of Classification Search
CPC . A61B 2034/2063; A61B 8/461; A61B 8/488; A61M 5/158; A61M 25/0108; A61M 2005/1588; A61M 25/0084
See application file for complete search history.

(56) References Cited

U.S. PATENT DOCUMENTS

| | | | |
|---|---|---|---|
| 4,441,503 A | 4/1984 | O'Donnell | |
| 4,470,305 A | 9/1984 | O'Donnell | |
| 4,569,231 A | 2/1986 | Carnes et al. | |
| 4,697,595 A | 10/1987 | Breyer et al. | |
| 4,706,681 A | 11/1987 | Breyer et al. | |
| 5,161,536 A | 11/1992 | Vilkomerson et al. | |
| 5,329,927 A | 7/1994 | Gardineer et al. | |
| 5,588,432 A * | 12/1996 | Crowley | A61B 5/02007 600/374 |
| 5,830,144 A * | 11/1998 | Vesely | A61B 5/0422 600/459 |
| 5,840,030 A | 11/1998 | Ferek-Petric et al. | |
| 5,840,031 A * | 11/1998 | Crowley | A61B 8/12 600/440 |
| 5,860,923 A * | 1/1999 | Lenker | A61B 5/02014 600/433 |
| 6,004,269 A * | 12/1999 | Crowley | A61B 8/4461 600/374 |
| 2003/0036696 A1 | 2/2003 | Willis et al. | |
| 2006/0106375 A1* | 5/2006 | Werneth | A61B 18/1492 606/32 |
| 2007/0167822 A1* | 7/2007 | Webler | A61M 25/0009 600/463 |
| 2007/0213616 A1* | 9/2007 | Anderson | A61B 8/0833 600/448 |
| 2007/0299404 A1* | 12/2007 | Katoh | A61M 25/008 604/173 |
| 2008/0275380 A1 | 11/2008 | Hennings et al. | |
| 2009/0005675 A1 | 1/2009 | Grunwald et al. | |
| 2009/0030380 A1* | 1/2009 | Binmoeller | A61M 25/104 604/264 |
| 2009/0118612 A1 | 5/2009 | Grunwald et al. | |
| 2010/0179522 A1* | 7/2010 | Companion | A61B 34/10 606/10 |
| 2012/0165785 A1* | 6/2012 | Schatz | A61M 25/0074 604/508 |
| 2014/0094692 A1* | 4/2014 | Tolkowsky | G06T 7/33 600/424 |

OTHER PUBLICATIONS

McMahon EM, Jiamsripong P, Katayama M, Chaliki HP, Fatemi M, Belohlavek M. Accurate guidance of a catheter by ultrasound imaging and identification of a catheter tip by pulsed-wave Doppler. Pacing Clin Electrophysiol 2012;35:44-50.

Belohlavek M, Katayama M, Zarbatany D, et al. Acoustically active injection catheter guided by ultrasound: navigation tests in acutely ischemic porcine hearts. Ultrasound Med Biol 2014;40:1650-9.

Williams AR, Trachtenberg B, Velazquez DL, McNiece I, Altman P, Rouy D, Mendizabal AM, Pattany PM, Lopera GA, Fishman J, Zambrano JP, Heldman AW, Hare JM. Intramyocardial stem cell injection in patients with ischemic cardiomyopathy: functional recovery and reverse remodeling. Circ Res 2011;108:792-6. PMID: 21415390.

Losordo DW, Henry TD, Davidson C, Sup Lee J, Costa MA, Bass T, Mendelsohn F, Fortuin FD, Pepine CJ, Traverse JH, Amrani D, Ewenstein BM, Riedel N, Story K, Barker K, Povsic TJ, Harrington RA, Schatz RA. Intramyocardial, autologous CD34+ cell therapy for refractory angina. Circ Res 2011;109:428-36. PMID: 21737787.

Armstrong, et al., Localization of Needle Tip with Color Doppler During Pericardiocentesis: In Vitro Validation and Initial Clinical Application, Journal of the American Society of Echocardiography, 2001, 14:29-37.

Fronheiser, et al., Real-Time 3D Color Doppler for Guidance of Vibrating Interventional Devices, 2004 IEEE Ultrasonics Symposium, 1:149-152.

Fronheiser, et al., Vibrating Interventional Device Detection Using Real-Time 3-D Color Doppler, IEEE Transactions on Ultrasonics, Ferroelectrics, and Frequency Control, 2008, 55(6):1355-1362.

McMahon, et al., Accurate Guidance of a Catheter by Ultrasound Imaging and Identification of a Catheter Tip by Pulsed-Wave Doppler, Pacing and Clinical Electrophysiology, First Published Online: Nov. 6, 2011, DOI: 10.1111/j.1540-8159.2011.03262.x, 7 pages.

PCT International Search Report and Written Opinion, PCT/US2011/047711, dated Dec. 16, 2011.

Anagnostopoulos PC, Pislaru C, Seward JB and Belohlavek M (2002). "Epicardial ultrasound guidance of coronary catheter placement in an experimental animal model." J Am Soc Echocardiogr 15:1387-90.

Asanuma T, Belohlavek M, Bae RY, Greenleaf JF and Seward JB (2001). "Radiofrequency spectral analysis of attenuated ultrasound signals in experiments with echo contrast microbubbles." J Am Soc Echocardiogr 14:789-97.

Asanuma T, Khandheria BK, Seward JB and Belohlavek M (2002). "Radio frequency dual-spectra analysis of regional myocardial perfusion." J Am Soc Echocardiogr 15:1277-84.

Belohlavek M, Foley DA, Gerber TC, Kinter TM, Greenleaf JF and Seward JB (1993). "Three- and four-dimensional cardiovascular ultrasound imaging." Mayo Clin Proc 68:221-40.

Belohlavek M, Foley DA, Seward JB and Greenleaf JF (1994). "Diagnostic performance of two-dimensional versus three-dimensional transesophageal echocardiographic images of selected pathologies evaluated by receiver operating characteristic analysis." Echocardiography 11 :635-45.

Belohlavek M, Manduca A, Buithieu J, Greenleaf JF and Seward JB (1996). "Extraction of endocardial boundary from echocardiographic images by means of the Kohonen self-organizing map." Acoustical Imaging. Plenum Press 22:197-202.

Belohlavek M, Asanuma T, Kinnick RR and Greenleaf JF (2001). "Vibro-acoustography: quantification of flow with highly-localized low-frequency acoustic force." Ultrason Imaging 23:249-56.

Bjaerum S, Torp H and Kristoffersen K (2002). "Clutter filter design for ultrasound color flow imaging." IEEE Trans Ultrason Ferroelectr Freq Control 49:204-16.

Fatemi M and Greenleaf JF (1998). "Ultrasound-stimulated vibroacoustic spectrography." Science 280:82-5.

Heimdal A and Torp H (1997). "Ultrasound Doppler measurements of low velocity blood flow: limitations due to clutter signals from vibrating muscles." IEEE Trans Ultrason Ferrorelec Freq Control 44:873-881.

Karmarkar PV, Kraitchman DL, Izbudak I, Hofmann LV, Amado LC, Fritzges D, Young R, Pittenger M, Bulte JW and Atalar E (2004). "MR-trackable intramyocardial injection catheter." Magn Reson Med 51:1163-72.

(56) References Cited

OTHER PUBLICATIONS

Kenny A, Wisbey CR and Shapiro LM (1994). "Measurement of left anterior descending coronary artery flow velocities by transthoracic Doppler ultrasound." Am J Cardiol 73:1021-2.

Lloyd-Jones OM, Larson MG, Leip EP, Beiser A, D'Agostino RB, Kannel WB, Murabito JM, Vasan RS, Benjamin EJ and Levy D (2002). "Lifetime risk for developing congestive heart failure: the Framingham study." Circulation 106:3068-3072.

Pizzuto F, Voci P, Mariano E, Puddu PE, Chiavari PA and Romeo F (2003). "Noninvasive coronary flow reserve assessed by transthoracic coronary Doppler ultrasound in patients with left anterior descending coronary artery stents." Am J Cardiol 91:522-6.

Rodriguez-Parcel M, Brinton T J, Chen IY, Gheysens 0, Lyons J, I keno F, Willmann JK, Wu L, Wu JC, Yeung AC, Yock P. and Gambhir SS (2008). "Reporter gene imaging following percutaneous delivery in swine moving toward clinical applications." J Am Coll Cardiol 51:595-7.

Sikdar S, Kim Y, Leotta OF, Primozich JF and Beach KW (2004). "Ultrasonic techniques for assessing wall vibrations in stenosed arteries." Conf Proc IEEE Eng Med Biol Soc 2: 1325-8.

Sikdar S, Lee JC, Remington J, Zhao XQ, Goldberg SL, Beach KW and Kim Y (2007). "Ultrasonic Doppler vibrometry." J Am Soc Echocardiogr 20:1386-92.

Voci P, Pizzuto F, Mariano E, Puddu PE, Sardella G and Romeo F (2003). "Usefulness of coronary flow reserve measured by transthoracic coronary Doppler ultrasound to detect severe left anterior descending coronary artery stenosis." Am J Cardiol 92:1320-4.

Von Bibra H, Voigt JU, Froman M, Bone D, Wranne B and Juhlin-Dannfeldt A (1999). "Interaction of Microbubbles with Ultrasound." Echocardiography 16:733-741.

Wada N, Watanabe N, Yamaura Y, Neishi Y, Koyama Y, Kawamoto T, Akasaka T and Yoshida K (2005). "Comparison of high-frequency two-dimensional transthoracic echocardiography versus intravascular ultrasound for evaluation of the left anterior descending coronary artery." Am J Cardiel 96:1746-9.

Wang J, Abraham TP, Korinek J, Urheim S, McMahon EM and Belohlavek M (2005). "Delayed onset of subendocardial diastolic thinning at rest identifies hypoperfused myocardium." Circulation 111:2943-50.

Wang J, Korinek J, Urheim S, Abraham T and Belohlavek M (2005). "Direct identification of subendocardial postsystolic thickening by intracardiac M-mode Doppler echocardiography." Echocardiography 22:145-7.

Wang J, Urheim S, Korinek J, Abraham TP, McMahon EM and Belohlavek M (2006). "Analysis of postsystolic myocardial thickening work in selective myocardial layers during progressive myocardial ischemia." J Am Soc Echocardiogr 19:1102-11.

Yoshifuku S, Chen S, McMahon E, Korinek J, Yoshikawa A, Ochiai I, Sengupta PP and Belohlavek M (2007a). "Parametric detection and measurement of perfusion defects in attenuated contrast echocardiographic images." J Ultrasound Med 26:739-48.

Yoshifuku S, Chen S, McMahon EM, Yoshikawa A, Sengupta PP, Korinek J and Belohlavek M (2007b). "Parametric harmonic-to-fundamental ratio contrast echocardiography: a novel approach to identification and accurate measurement of left ventricular area under variable levels of ultrasound signal attenuation." Ultrasonics 46:109-18.

\* cited by examiner

SYSTEMS AND METHODS FOR NAVIGATING A CATHETER AND DELIVERING A NEEDLE

CROSS-REFERENCE TO RELATED APPLICATIONS

This application is a continuation-in-part application of U.S. patent application Ser. No. 13/816,796 filed Apr. 24, 2013, which represents the national stage entry of PCT International Application PCT/US2011/047711 filed on Aug. 15, 2011 and claims benefit of U.S. Provisional Patent Application 61/375,093 filed Aug. 19, 2010. This application also claims benefit of U.S. Provisional Patent Application 62/166,942 filed May 27, 2015. The disclosure of each of the above-mentioned applications is incorporated herein by reference in its entirety.

STATEMENT OF FEDERALLY SPONSORED RESEARCH OR DEVELOPMENT

This invention was made with government support under EB009111 and EB019947 awarded by the National Institutes of Health. The government has certain rights in the invention.

BACKGROUND

Various ways are known in which ultrasound can be used to produce images of objects. In the so-called transmission imaging, for example, an ultrasound transmitter may be placed on one side of an object so as to have sound transmitted through the object to the ultrasound receiver that is placed on the other side of the object. With the transmission method, an image may be produced in which brightness of each pixel of an image is a function of the amplitude of the ultrasound that reaches the receiver ("amplitude-mode" or "A-mode"), or the brightness of each pixel of the displayed image is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver (this is referred to as "reflection", "backscatter" or "echo" imaging).

Several backscatter methods for acquiring ultrasound data are known. In the so-called "A-mode" method, an ultrasound pulse is directed into the object by the transducer and the amplitude of the reflected sound is recorded over a period of time. The amplitude of an echo signal is proportional to the scattering strength of reflecting elements in the object and the time delay is proportional to a distance separating these reflectors from the transducer. In the so-called "brightness-mode" or "B-mode" method, the transducer transmits a series of ultrasonic pulses as it is scanned across the object along a single axis of motion. The resulting echo signals are recorded in a fashion similar to that of the A-mode method and their amplitudes are used to modulate the brightness of pixels on a display. The location of the transducer and the time delay values of the received echo signals determine the display pixels to be illuminated. With the B-mode method, enough data are acquired from which a two-dimensional image of the reflecting elements can be reconstructed. Rather than physically moving the transducer over the subject to perform a scan, sometimes an array of transducer elements is employed while an ultrasonic beam is electronically moved or scanned (swapped) over a region of interest.

Ultrasonic transducers for medical applications are known to include one or more piezoelectric elements sandwiched between a pair of electrodes. A typical piezoelectric element is constructed of lead zirconate titanate (PZT), polyvinylidene diflouride (PVDF), or PZT ceramic/polymer composite. The electrodes of the piezo-element are connected to a voltage source, and application of voltage to the piezo-element triggers its change of dimensions at a frequency corresponding to that of the applied voltage. When a voltage pulse is applied, the piezoelectric element emits an ultrasonic wave, into the media to which it is coupled, at frequencies present in the excitation pulse. Conversely, when an ultrasonic wave strikes the piezoelectric element, the element produces a corresponding voltage across its electrodes. Typically, the front of the element is covered with an acoustic matching layer that improves acoustical coupling with the media in which the ultrasonic waves propagate. In addition, a backing material may be disposed to the rear of the piezoelectric element to absorb ultrasonic waves that emerge from the back side of the element so that they do not interfere. A number of such ultrasonic transducer constructions have been disclosed (see, e.g., U.S. Pat. Nos. 4,217,684; 4,425,525; 4,441,503; 4,470,305 and 4,569,231).

When used for ultrasound imaging, the transducer typically has a number of piezoelectric elements arranged in an array and driven with separate voltages (apodizing). By controlling the time delay (or phase) and amplitude of the applied voltage signals, the ultrasonic waves produced by such a phase array of piezoelectric elements (in the transmission mode) combine to create a net ultrasonic wave focused at a selected point. By controlling the time delay and amplitude of the applied voltages, this focal point can be moved in a plane to scan the subject.

The same principles apply when the transducer is employed to receive the object sound (using echo imaging approach). Specifically, the voltage signals produced at the transducer elements in a phase-array are summed together such that the net signal is indicative of the sound reflected from a single focal point in the object. As with the transmission imaging, this focused reception of the ultrasonic energy is achieved by imparting separate time delay (and/or phase shifts) and gains to the echo signal received by each transducer array element.

Doppler systems employ ultrasonic pulses (pulsed-wave, or PW, Doppler) or continuous acoustic beam (continuous-wave, or CW, Doppler) to measure the velocity of moving reflectors, such as flowing blood cells ("flow" Doppler) or moving cardiac walls ("tissue" Doppler). Velocity is detected by measuring the Doppler shifts in frequency imparted to the ultrasound signal from the moving reflectors. The PW Doppler method is suitable for defining a small sample window, within which velocity of reflectors is measured, whereas the CW Doppler method is typically preferred for measurement of maximum velocity of reflectors moving along the ultrasound beam.

Doppler imaging may be incorporated in a real-time scanning imaging system. The system provides electronic steering and focusing of a single acoustic beam and enables small volumes to be illuminated anywhere in the field of view of the instrument, whose locations can be visually identified on a two-dimensional B-mode image. A Fourier transform processor faithfully computes the Doppler spectrum backscattered from the sampled volumes, and by averaging the spectral components the mean frequency shift can be obtained. Typically the calculated velocity is expressed in the B-mode image by color-coding individual pixels.

With the advent of numerous minimally invasive procedures, proper catheter guidance is becoming increasingly important. Within the field of interventional medicine, catheters have become widely used for a number of both diagnostic and therapeutic procedures. For example, in the particular field of cardiology, catheters and catheter-based tools are used for coronary angiograms, cardiac ablation, and percutaneous procedures including coronary interventions including angioplasty, atherectomy, and stent or closure device placement. Other medical specialties also use catheters for various purposes including fluid drainage, injections, and biopsy or so-called minimally-invasive surgical procedures. Future application of catheters may also include precise in situ delivery of personally tailored drugs or gene therapy.

Regardless of ultrasound (US) equipment used and the type of scan employed by this equipment, the interventions into the cardiovascular system of a patient by the imaging-navigation system have to be minimally invasive in order to be advantageous in comparison with the full-extent (open-chest) surgery and direct (visual) navigation of tools and instruments by a surgeon or skilled and qualified operator.

The related art describes cardiovascular catheter navigation. Traditionally, cardiac catheterization procedures have been done under the guidance of fluoroscopy. One of such methodologies allows for a sparse electromechanical mapping of the endocardial surface of the left ventricle (LV) by employing a so-called NOGA catheter that is placed into the LV under the X-ray control, which is required because NOGA lacks a capability to provide an anatomical image of the heart. This approach has a number of drawbacks such as exposure to ionizing radiation for both a patient and medical personnel, projection of large three-dimensional (3D) imaging field (through the entire depth of body) onto a two-dimensional (2D) plane, and the necessity to use specialized procedure rooms. In addition, while NOGA allows for detection of the endocardial surface, it cannot detect the motion of the cardiac wall and has limited spatial resolution. Finally, the cost of employing this method and the required stereotactic systems is rather prohibitive.

The described limitations led to a development of a number of new methods for catheter guidance including the use of magnetic navigation, registration of previously acquired images with fluoroscopic and/or ablation system images, electroanatomic voltage-gradient guidance, non-contact mapping systems, and remotely-controlled robotic systems.

One of the methods, which is currently at a stage of experimental proof-of-concept, is an intramyocardial injection catheter tracking with magnetic resonance imaging (MRI) by means of a radiofrequency (RF) antenna with a receiver coil at its tip. This approach was shown to identify an infracted myocardium with the use of real-time MRI for guiding the catheter from a carotid artery. The deficiencies of this not-yet-proven technique include a need in a costly MRI suite, confinement of the catheterization team in proximity to the magnet, and prohibition on use of any metallic instruments.

Another approach, which can be used during the applications of sonomicrometry, is to guide catheter with ultrasound imaging. Sonomicrometry uses, for experimental analyses of local cardiac motion, miniature crystals (typically 1-2 mm in diameter; made, for example, from a piezoelectric material). The crystals transmit to and receive from each other approximately 1-MHz US-pulses at about 250-Hz rate, thereby bringing about a measurement of a distance separating these crystals based on the measurement of the time-of-flight.

While a catheter lends itself to being guided with US during insertion, the obtained US-images suffer from speckle patterns and backscatter pattern ambiguity, easily causing errors in the determination of the position of the catheter tip within the cardiovascular system. Such confusing speckle patterns, SP, are indicated in FIG. 1A showing subendocardial placement of the crystals C1 and C2. FIGS. 1B and 1C illustrate similar limitations of a conventional ultrasound modality in depicting a catheter inside the LV using the intracardiac ultrasound scan and the transthoracic scan, both of which otherwise can be used for basic, approximate guidance of the intervention catheter. It was observed that the simultaneous operation of the sonomicrometer and electrocardiography (echo) suffers from acoustic interference hindering the clarity of US images used for navigation of the sonomicrometric catheter and causing the users to turn off the sonomicrometry system while acquiring echoes and, therefore, causing not saving the sonomicrometric data during imaging.

A skilled artisan shall realize, therefore, that while commonly-available, real-time ultrasonographic systems may satisfy the requirement of being minimally invasive and can be used alone to guide catheters, they have fundamental limitations. The use of US imaging system alone to guide catheters within human body (and, in particular, within the heart as discussed herein), suffers from a problem of differentiating the actual tip of the catheter from a bend coming in or out of the 2D plane. Rapidly evolving 3D US imaging is expected to improve spatial determination of objects, including the localization of a catheter. But the transition from 2D to 3D only converts the problem of reliably localizing the tip of the catheter in or out of a 2D plane to a problem of determining the tip location in or out of a 3D space. The fundamental limitations of US signal propagation, including refraction, attenuation, rather unpredictable backscatter patterns, and signal drop-outs are sources of imaging artifacts that compromise catheter navigation regardless of spatial dimensionality. Furthermore, the ultrasound image of the catheter tip is often disguised on the background of an image of soft tissue because the backscatter pattern of the catheter is not unique. As a result, a position of the catheter tip is often misinterpreted or determined inaccurately if the actual tip is located out of the scan plane. This could lead to accidental injury or piercing of the cardiac wall.

As described, injection catheters may be used for delivery of therapeutic or investigative agents, such as emerging intracardiac delivery of cell therapy. Conventional injection catheters typically have a retractable needle at the distal end, that is, at a tip, of the catheter. When the tip of the catheter is in contact with the targeted anatomic location, for example, with an inner surface of the LV wall in the region of infarction, the needle is exposed by means of a manual handle and slider, inserted into the targeted tissue (that is, into myocardium in this example), and the therapeutic or investigative agent is injected.

Furthermore, as described, placement of the injection catheter is frequently performed manually. The physician relies on external landmarks, knowledge of anatomy, experience, and skills to accurately place the catheter tip and insert the needle. Developments in medical imaging technologies, such as computed tomography imaging, magnetic resonance imaging, and ultrasound imaging, have provided some capability for image-guided placement of catheters (and a variety of other minimally invasive investigative or therapeutic instruments) in particular anatomic locations in the heart or elsewhere in the body. In some instances, real-time medical imaging may be available during placement of the catheter. In other instances, a previously obtained image may be available as a guide for catheter placement.

A limitation of intracardiac therapeutic or investigative agent delivery includes accurate guidance of an injection catheter into the desired location. More specifically, the most common problem in such minimally invasive procedures is accurate targeting of an exact anatomic location. This can be particularly challenging within a beating heart.

Additionally, when visualizing catheters using conventional (B-mode) ultrasound, 2D and 3D scans can confuse the tip with a cross section through the catheter body. The catheter also often visually merges with the surroundings or is blurred by image noise and artifacts.

Conventional injection catheters fail to provide a system for determining the depth into which the tip of the needle has reached when inserted into tissue. Inefficient delivery of a therapeutic or investigative agent (for example, suboptimal depth within the LV wall or backward leaking of the agent along a shallowly inserted needle) or LV wall perforation and pericardial effusion are examples of potential complications of inappropriate needle insertion length during transendocardial injections with the intracardiac injection catheter.

Thus, a real-time, accurate, image-guided navigation of a catheter tip to a target anatomic location and depth-controlled location, for example, to perform an efficient delivery of a therapeutic or investigative agent by an injection needle exposed from the catheter tip and inserted into an anatomic target, is highly desirable.

SUMMARY

In a first aspect of the disclosure, an acoustically active catheter (AAC) system is provided for delivering a needle to a desired anatomic location. The AAC system includes an injection catheter including a needle. The injection catheter includes an outer tube including a first lumen. The injection catheter includes an inner tube disposed within the first lumen of the outer tube, where the inner tube includes a second lumen. The needle is slidably disposed within the second lumen of the inner tube. The injection catheter includes a first acoustic marker and a second acoustic marker. The first acoustic marker is at or proximate to a distal end of the injection catheter and configured to generate a first acoustic signal. The second acoustic marker is proximate to the distal end of the needle and configured to generate a second acoustic signal.

In accordance with another aspect of the disclosure, a system is provided including an injection catheter. The injection catheter includes an outer tube comprising a first lumen, an inner tube disposed within the first lumen of the outer tube, the inner tube comprising a second lumen, a needle slidably disposed within the second lumen of the inner tube, and a first acoustic marker proximate to a distal end of the injection catheter and configured to generate a first acoustic signal. The injection catheter also includes a second acoustic marker proximate to the distal end of the needle and configured to generate a second acoustic signal.

In accordance with a third aspect of the disclosure, a method is provided that includes providing a catheter comprising a catheter tip equipped with a crystalline element adapted to actively generate a first acoustic wave at a first frequency and generating, by an ultrasound imaging system including an ultrasound transducer, an image of the catheter tip arranged within a body based on an ultrasound echo produced by ultrasound waves generated by the ultrasound transducer and reflected by the catheter tip. The method also includes detecting, by the ultrasound imaging system, an acoustic interference signal formed by the first acoustic wave generated by the crystalline element and a second acoustic wave generated by the transducer and displaying, by the ultrasound imaging system, a position of the catheter tip in response to the detected acoustic interference signal.

In accordance with yet another aspect of the disclosure, a method is provided that includes producing a first signal having a first frequency using a first acoustic marker located at a catheter tip of an injection catheter, the injection catheter comprising a needle and producing a second signal having a second frequency using a second acoustic marker located at a needle tip of the needle. The method also includes receiving by an ultrasound transducer third and fourth signals having third and fourth frequencies. The third and fourth frequencies are formed due to interaction of the first signal from the first acoustic marker with the Doppler signal transmitted by an ultrasound imaging transducer.

The foregoing and other aspects and advantages of the invention will appear from the following description. In the description, reference is made to the accompanying drawings, which form a part hereof and in which there is shown by way of illustration a preferred embodiment of the invention. However, such embodiment does not necessarily represent the full scope of the invention and reference is made therefore to the claims and herein for interpreting the scope of the invention.

DETAILED DESCRIPTION

Figure 1A:
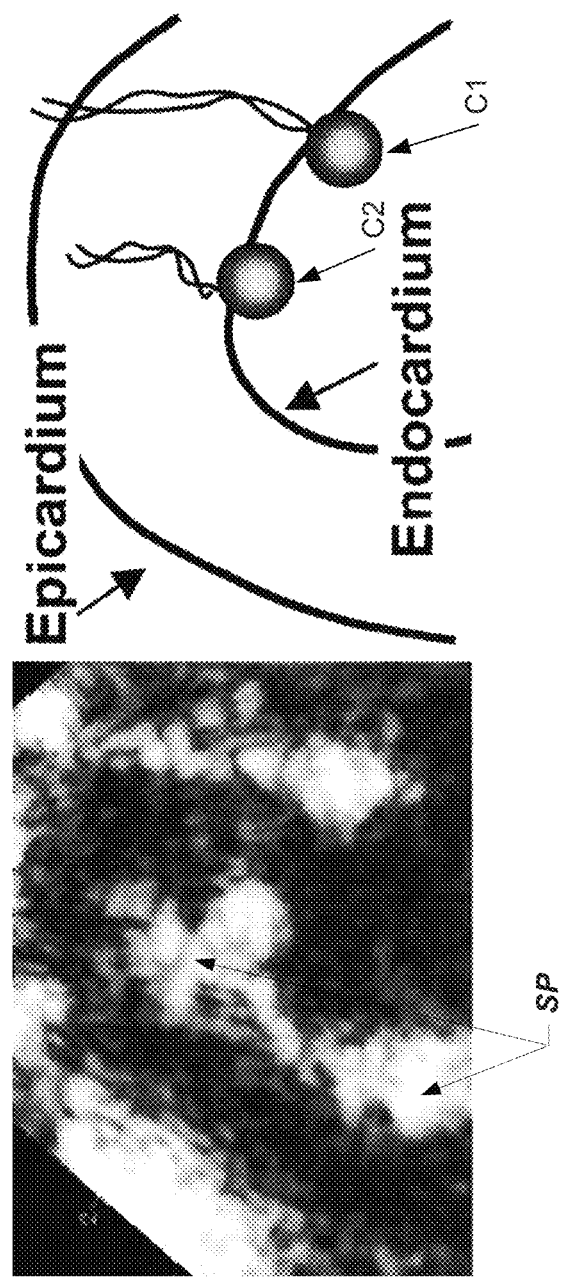
FIG. 1A is an image representing an ultrasound scan of two crystals subendocardially implanted in the anteroapical myocardium. Variable speckle patterns (SP) could be mistaken for the location of the crystal.
Figure 1B:
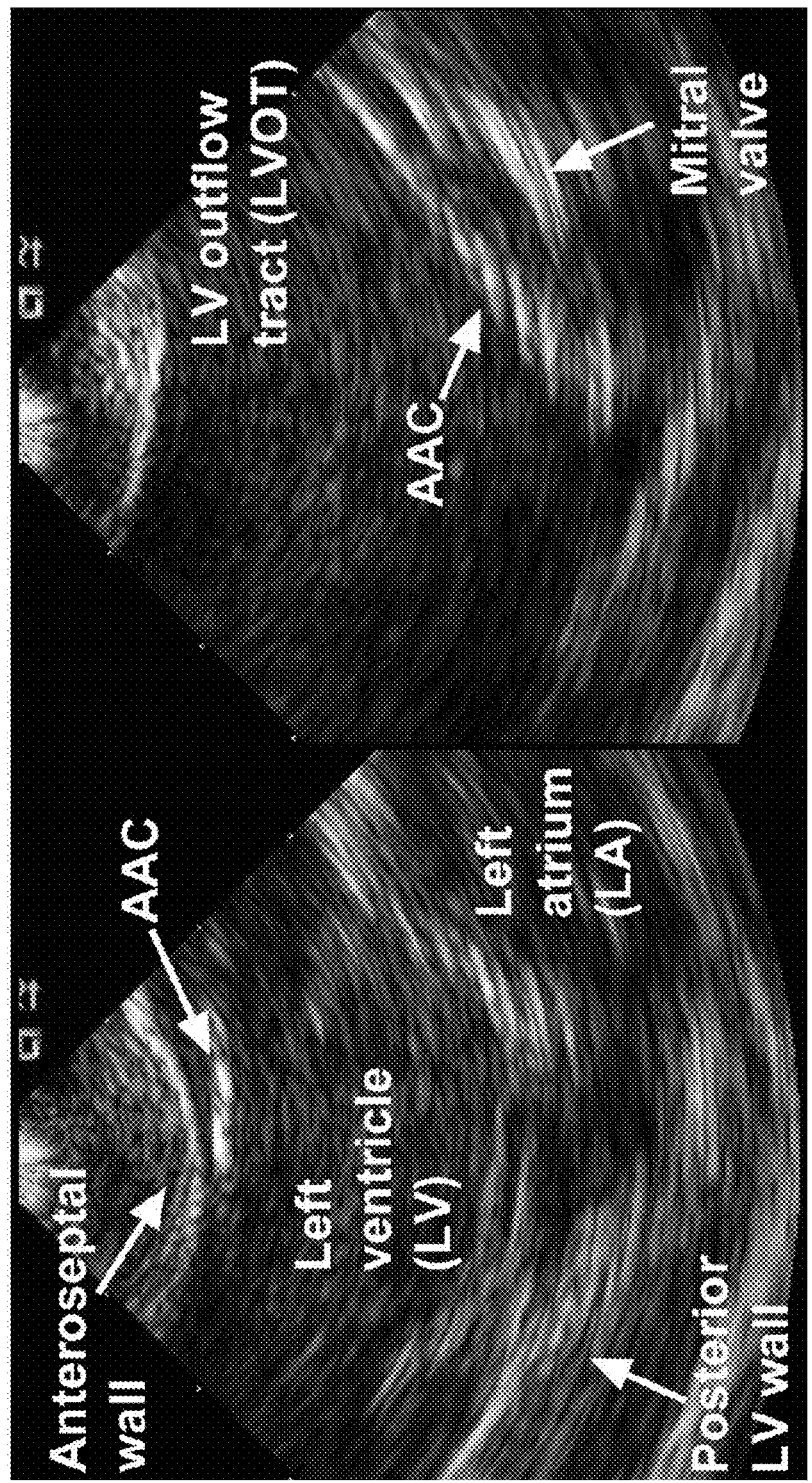
FIG. 1B is an intracardiac ultrasound (ICUS) image, taken from the right ventricle, of the acoustically active catheter (AAC) that is being advanced from the LV cavity towards the posterior wall. Various imaging artifacts could confound determination of the catheter position.
Figure 1C:
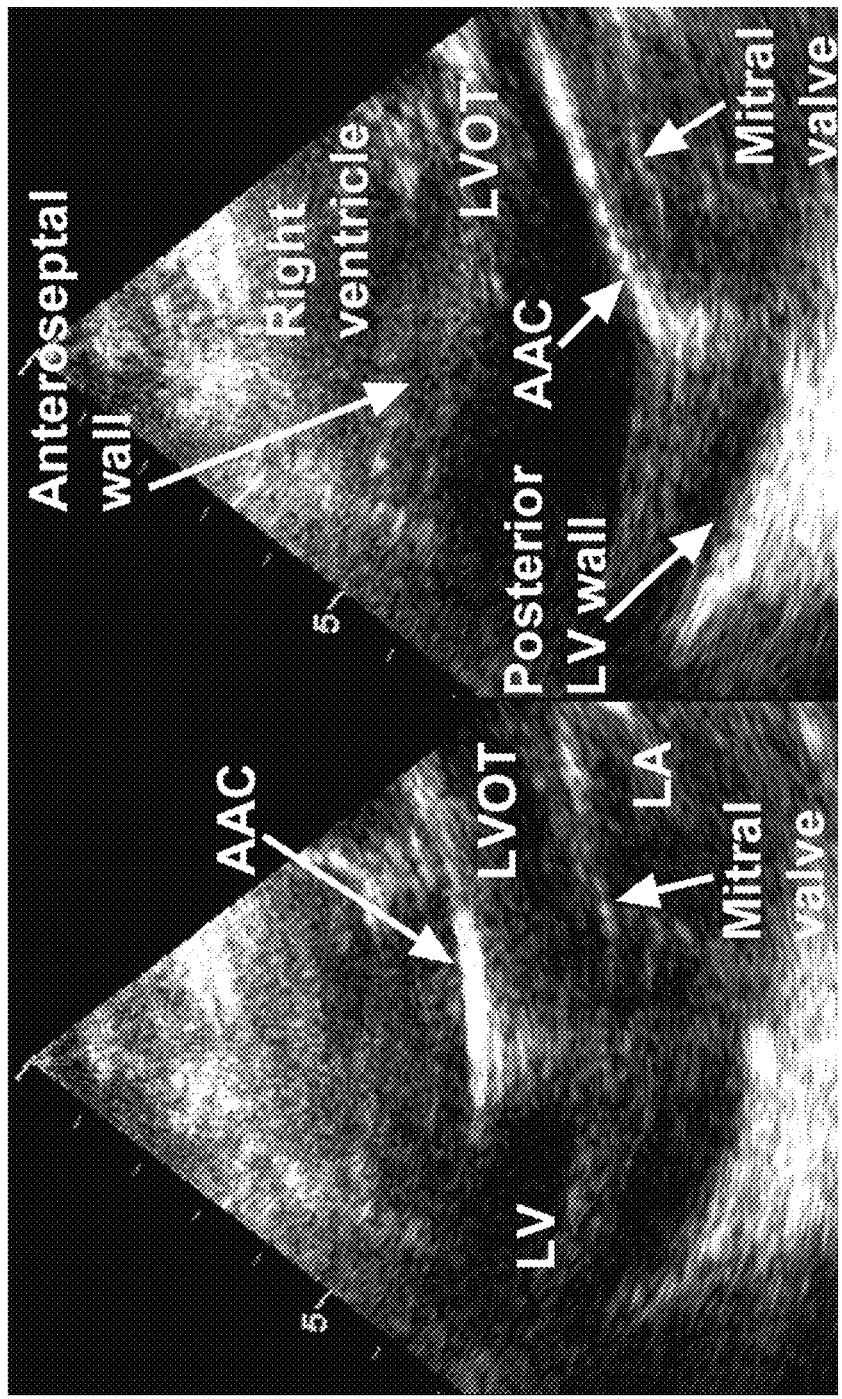
FIG. 1C is an example of a transthoracic scan from the parasternal projection.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and/or in reference to a figure, is intended to provide a complete description of all features of the invention.

In addition, in drawings, with reference to which the following disclosure may describe features of the invention, like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented in this view in order to simplify the given drawing and the discussion, and to direct the discussion to particular elements that are featured in this drawing.

A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily be shown in each and every drawing describing such embodiment, the presence of this detail in the drawing may be implied unless the context of the description requires otherwise. In other instances, well known structures, details, materials, or operations may not be shown in a given drawing or described in detail to avoid obscuring aspects of an embodiment of the invention that are being discussed.

Furthermore, the described features, structures, or characteristics of the invention may be combined in any suitable manner in one or more embodiments. Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

Consequently, the invention as recited in claims appended to this disclosure is intended to be assessed in light of the disclosure as a whole.

The terms "interference", "interferometric", and the like in the context of this disclosure refer to interaction of the signals associated with the crystalline element at the tip of the AAC and the transducer of the US-imaging machine. These signals, referred to interchangeably as "acoustic signals", "acoustic waves", and the like, generally have a wide range of waveform shapes such as, for example, the sinusoidal or square shapes, and acoustic frequencies such as, for example, the frequencies in the audible and ultrasound ranges. The ultrasound transducer and US-imaging system may operate in various Doppler modes, for example, pulsed-wave (PW), continuous-wave (CW), and color flow (CF) during identification of the AAC tip.

Figure 2:
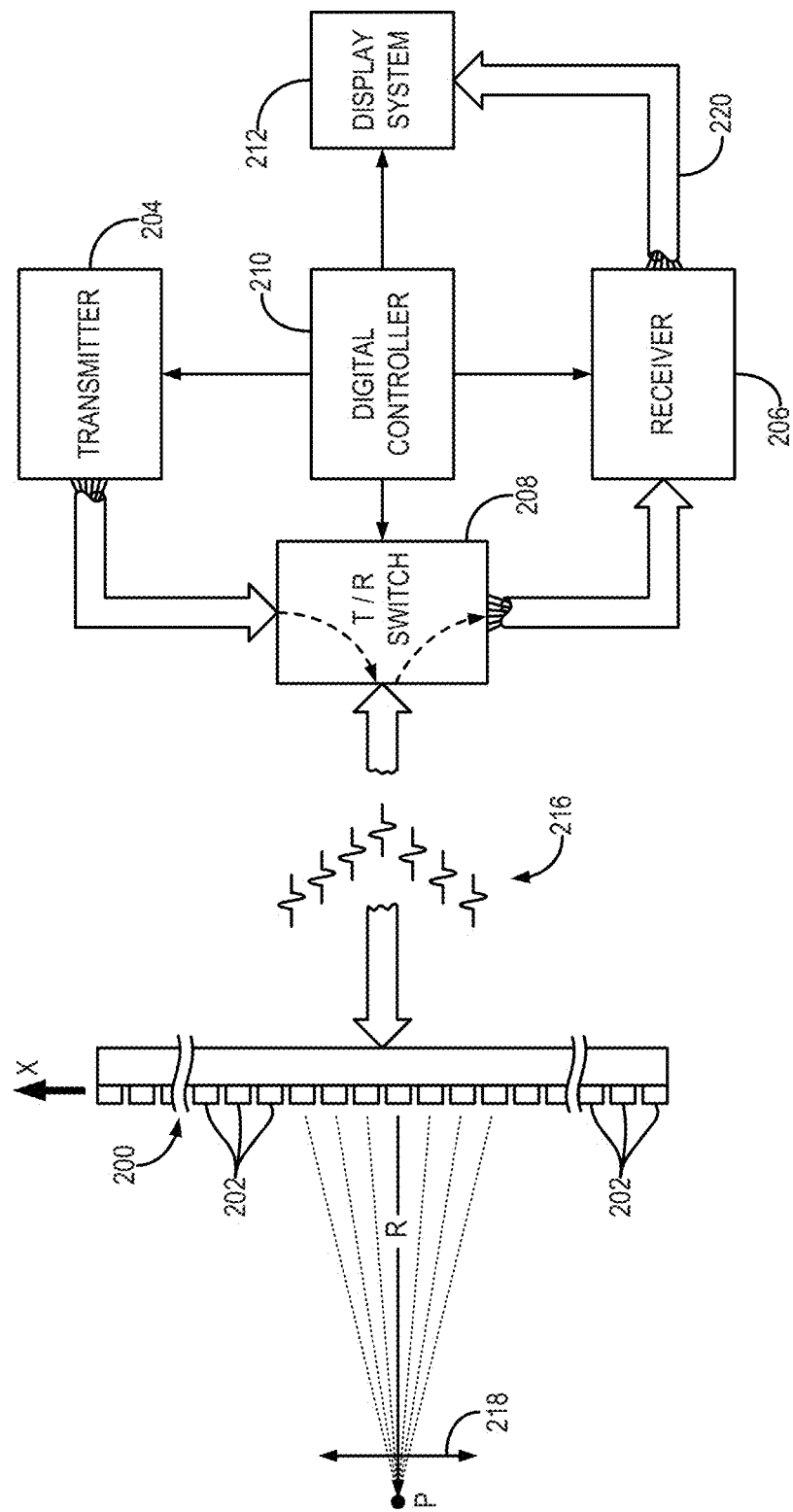
FIG. 2 is a block diagram of an example of the ultrasonic imaging system, which employs an embodiment of the present invention.

Referring particularly to FIG. 2, an ultrasonic imaging system includes a transducer array 200 comprised of a plurality of separately driven elements 202, each of which produces a burst of ultrasonic energy when energized by a pulse generated by a transmitter 204. The ultrasonic energy reflected back to the transducer array 200 from the subject under study (SUT, not shown) is converted to an electrical signal by each transducer element 202 and applied separately to a receiver 206 through a set of switches 208. The transmitter 204, receiver 206, and the switches 208 are operated under the control of a digital controller 210 responsive to the commands input by a human operator. A complete scan is performed by acquiring a series of echoes in which the switches 208 are set to their "transmit" position, the transmitter 204 is gated on momentarily to energize each transducer element 202, the switches 208 are then set to their "receive" position, and the subsequent echo signals produced by each transducer element 202 are applied to the receiver 206. The separate echo signals from each transducer element 202 are combined in the receiver 206 to produce a single "echo" signal that is further employed to produce a line in an image displayed on a display system 212.

The transmitter 204 may drive the transducer array 200 in such a fashion as to direct the produced ultrasonic beam substantially perpendicular to a front surface of the array 200. Referring particularly to FIG. 2, to focus this beam at a range R from the transducer array 200, a subgroup of the elements 202 are energized to produce the beam and the pulsing of the elements 202 that are located in a central portion of the array 200 in this subgroup are delayed relative to those elements 202 that are located in a peripheral portion of the array 200. Consequently, as a result of the interference of the small separate wavelets produced by the subgroup elements, a generated acoustic beam is focused at a point P. The time delay values associated with pulsing of the element 202 determine the depth of focus, or range R, which can be changed during a scan; the purpose of which is to produce a two-dimensional image. The same time delay pattern is used when receiving the echo signals resulting in dynamic focusing of the echo signals received by the subgroup of elements 202. In this manner a single scan line in the image is formed.

To generate the next scan line, the sub-group elements to be energized is shifted by one element-position along the transducer length and another scan line is acquired in a fashion similar to that described above. In operation, therefore, the focal point P of the ultrasonic beam is thus shifted (not shown) along the length of the transducer 200 by repeatedly shifting the location of the energized subgroup of elements 202.

The transducer 200 may be configured to produce an ultrasound beam that is scanned or steered angularly, alternatively or in addition to being scanned along the length of the transducer. For example, in a related embodiment, the transducer 200 is assembled in such a fashion as to have its elements 202 arranged in a two-dimensional matrix, and thereby is configured to produce an US beam that is scanned or steered angularly in two intersecting planes. Addition of such angular steering of the US beam to the longitudinal re-focusing of the beam described above allows the embodiment of FIG. 2 to scan the 3D space.

Color Doppler Imaging.

Recognition of the motion of an object on a local scale with the use of Doppler US imaging in any number of scans (alternately referred to herein as "image frames") acquired in a given scan-line is based on correlation between the pulses that are transmitted and reflected along the corresponding scan-lines (or beams), and depth (or distance) from the transducer element 202. A typical two-dimensional (2D) US image frame may consist of hundreds of scan-lines, and a train of US pulses is sent along each scan-line. As a result, formation of each Doppler-image frame requires numerous correlations of pulses to ultimately be displayed on the display system 212.

When an interrogated object is static and does not move, US-pulses reflected from the object in subsequent scans return to the receiver with the same time delay, because the pulses traverse the same round-trip distance between the transducer and the non-moving object. As a result, the corresponding pulses in the subsequent scans are optimally correlated. This optimal correlation indicates to the US-system that the object is not moving along the scan-line with respect to the transducer elements 202.

If, however, the interrogated object is moving, then reflected signals corresponding to two different scans have different time-delays. The time delay associated with a second scan is longer or shorter than that associated with a first scan depending on whether the object is moving away from or towards the transducer, respectively. As a result, there is a change in a degree of correlation between the corresponding pulses in the first and second scans. This change of correlation indicates to the US-system that the object is moving. By electronically "shifting" the pulse obtained in the second scan with respect to the pulse of the first scan, the US-system can be configured, either automatically or with the help of an operator, to find the optimal correlation between the two pulses. The shift needed to recover such optimal correlation is proportional to the displacement of the object along the scan-line that has occurred during the time-delay between the moments when the two subsequent image-frames have been acquired. Since this time-delay is known, the system can calculate both the direction and speed of motion of the object along the scan-line.

As will be described, using these concepts of Doppler imaging, and according to the embodiment of the invention, a local color marker (or overlay) is then associated, in the displayed image and in real-time, with a point along the scan-line at which the pulse reflected from the moving object has been received. The appropriate choice of such color overlay over the image point indicates to the user a direction of motion of the object (for example, red may mean "motion away from" the transducer and blue may mean "motion towards" the transducer, respectively) and speed (expressed, for example, on corresponding red-yellow or blue-green scales or according to any other chosen color-gamut).

In combination with a method of interferometric ultrasonography described below, the use of color-coding offers an operational advantage over the related art in that the proposed technique allows detecting and making visible even stationary objects. The present invention recognizes that, in order to effectuate a detection of the stationary objects, the US imaging system can be configured to interpret a stationary object as a moving object and label or tag it with a color marker representing a "change in position" detected through the interpreted "change in correlation" between the two reflected pulses corresponding to two different scan-lines. Having been appropriately color-coded by the US-system, the tagged image point becomes visible to the operator of the US-system as a colored dot on an image display. Moreover, a specific color-map can be further assigned to the tags so as to differentiate, by color coding, the detected tag-signal from the signals corresponding to ordinary motion of blood-flow, motion of tissue, or motion of navigated object itself (for example, the motion corresponding to advancement of a catheter into the heart).

Acoustically-Active Catheter (AAC) System and Modes of Operation

Figure 3A:
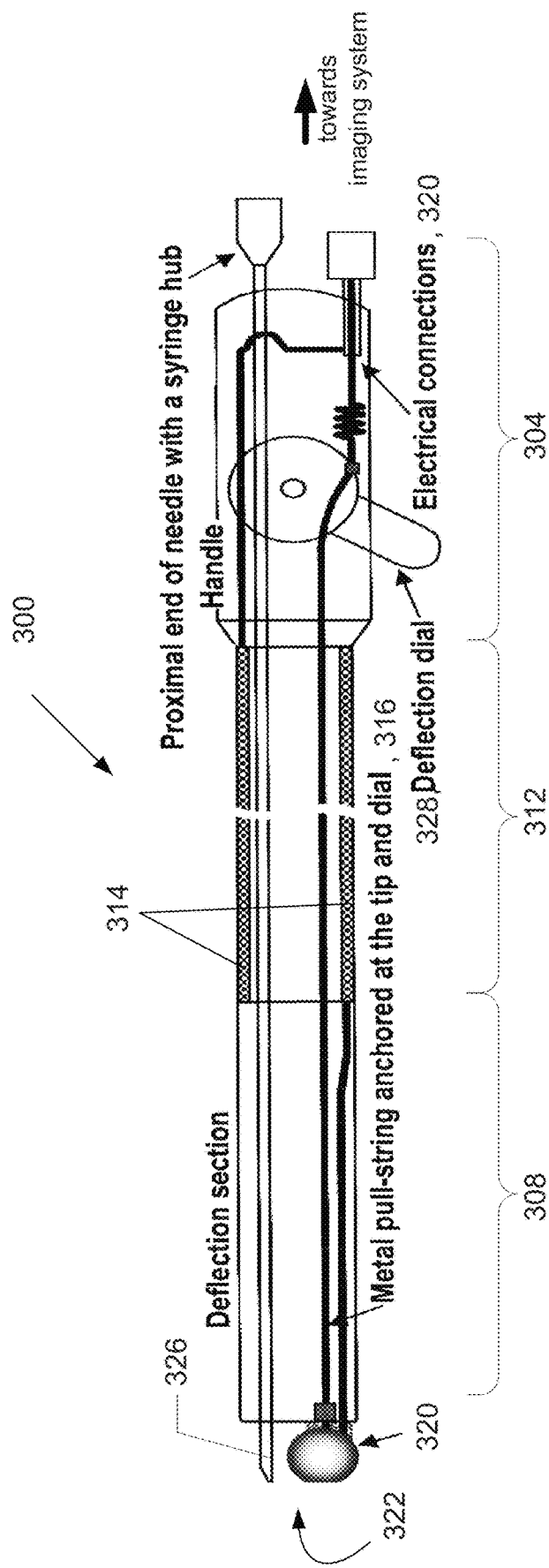
FIG. 3A is a schematic of a steerable intracardiac injection catheter equipped with an acoustically active tip according to one embodiment of the invention.

According to one embodiment, at least one miniature piezoelectric crystal is used as an ultrasonic tag in conjunction with a conventional US Doppler system. In particular, a distal end of a steerable catheter is equipped with a small piezoelectric crystal configured to operate in either transmitting or receiving mode, as discussed below, thereby forming an AAC-system of the invention. As schematically shown in FIG. 3A, an exemplary AAC-system 300 may include a proximal end having an AAC handle 304 and connected to a deflection section 308 of the catheter, which is located at its distal end, through a middle section 312 that may be strengthened with copper braiding 314. A metal pull-string 316 inside the catheter 300 is equipped with a crystalline element 320 (for example, a piezoelectric crystal) that is firmly affixed at the tip 322 of the distal section 308. Both the crystal 320 and the copper braiding 314 are appropriately attached via electrical connectors 324 to the electronic system (not shown) of the embodiment. As shown, the AAC 300 additionally includes a needle 326 and a deflection dial 328 governing the operation of the distal section 308. The AAC-system 300 is further operable with an US-imaging system, as known in the art (not shown).

The crystalline element 320 may be a single crystal located at the tip of the AAC 300. The crystalline element 320 may generate an acoustic signal having a frequency in a range of, for example, a few kHz, tens of kHz, or hundreds of kHz.

In the disclosure, the crystalline element 320 located at the catheter tip of the AAC 300 may vibrate and transmit energies omnidirectionally. The US signal caused by the vibration of the crystalline element 320 interacts with the Doppler ultrasound imaging signal transmitted by the US transducer and the resulting Doppler shift signal received by the transducer identifies the catheter tip of the AAC 300 in pulsed-wave (PW) or color Doppler scans. This works with any Doppler imaging system without any special wiring or direct connection between the AAC 300 and the Doppler imaging system.

In a particular implementation, a steerable AAC may employ a commercially-available steering catheter such as a Stiletto or a Myostar catheter. Stiletto is a trademark of Boston Scientific, Inc. (Natick, Mass.) and Myostar is a trademark of Biosense Webster, Inc. (Diamond Bar, Calif.). The Stiletto device, for example, consists of two concentric fixed-curve guide catheters (9 Fr and 7 Fr) and an inner spring-loaded needle component, and the steering of its distal end is achieved by manipulating the positions of the two concentric guide catheters relative to each other. The Myostar device is an 8 Fr deflectable catheter equipped with a 27-gauge extendable and retractable needle having adjustable depth for targeted intramyocardial delivery. The distal tip of the Myostar device is deflected by pulling an internal metal string anchored to the inner side of the distal deflection system. The pull wire simultaneously serves as an electrical connection to the metal tip of the catheter, and the catheter is both strengthened and electrically shielded by copper braiding.

Figure 3B:
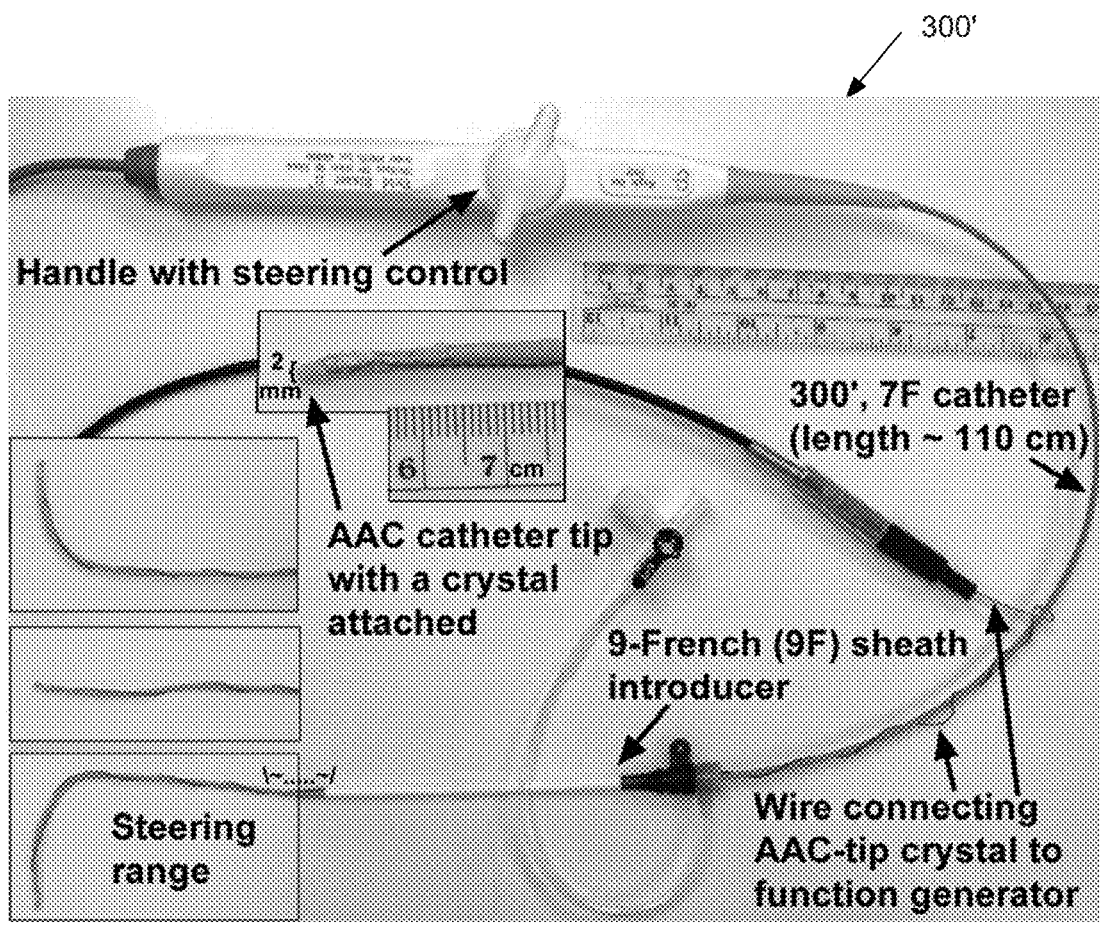
FIG. 3B is a picture of an exemplary Blazer™ catheter; the catheter is furnished with an acoustically active tip according to an alternative embodiment of the invention.
Figure 3C:
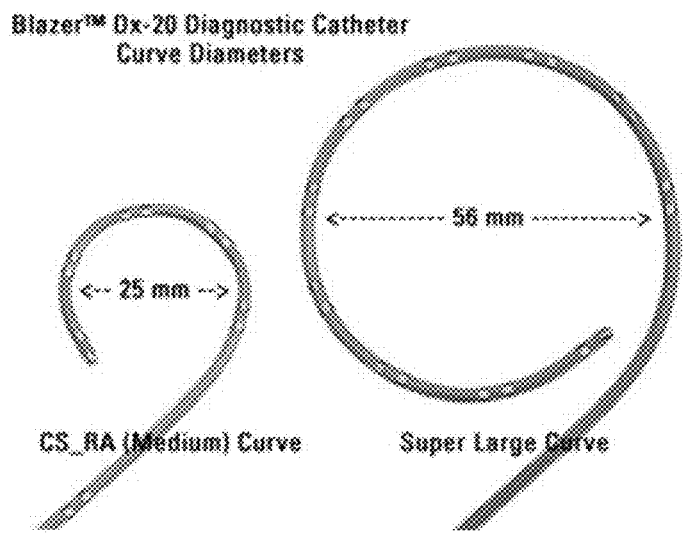
FIG. 3C is a diagram showing that the tip-end of the catheter of FIG. 3B is deflectable, at different radii, to ensure a movement of the tip in all three spatial dimensions.

In a related embodiment, a different type if steerable catheter without an injection needle such as a Blazer catheter can be used. Blazer is a trademark of Boston Scientific, Inc. (Natick, Mass.). The Blazer catheter has a steerable tip deflectable and is bendable in three dimensions as shown in FIGS. 3(B, C). The deflection movement of the Blazer tip is controlled with a knob in the middle of the handle, which angularly steers the end of the catheter by curving it in a loop shown in FIG. 3C. Control of the rotation of the catheter within a 360 degree angle is provided by twisting the handle, thereby causing the end of the catheter to rotate around the longitudinal axis of the catheter. The length of the distal end of the catheter inserted into the cardiovascular system is controlled by pushing and pulling of the handle at the proximal end of the catheter. A combination of these three degrees of movement—the steering of the tip through angular deflection, the rotational motion of the tip caused by the rotation of the catheter handle, and the controlled longitudinal insertion of the catheter—empowers the user to manipulate the tip of the Blazer™ device within 3D space, such as, for example, an intracardiac chamber.

In yet another related embodiment, a steerable sheath such as a Unison steerable sheath can be used. Unison is a trademark of Greatbatch Medical (Minneapolis, Minn.). This sheath has, in principle, the same steering capabilities and manual controls like the Blazer, Myostar, or Stiletto devices. The lumen of the Unison sheath can accommodate an up to 8 Fr catheter or tubing, thus facilitating prototyping of a steerable catheter. By affixing a crystalline element at the tip of the Unison sheath, an acoustically active catheter can be built, such as an injection AAC schematically shown in FIG. 7 and depicted in FIGS. 11A and 12A. Besides injection catheters, the AAC-system of the invention can be used with a variety of catheter systems including electrophysiological, biopsy, or ablation catheters and other investigative or surgical tools for catheter guidance during minimally invasive interventions.

According to one embodiment of the invention, the AAC 300 of FIG. 3A or the AAC 300' of FIGS. 3(B, C) is functionally reconfigurable in that it may be operated as a transmitter or as a receiver. Either type of operation of the AAC can be advantageously used for catheter navigation, as discussed below.

In a transmitting mode, for example, the crystalline element 320 is electrically driven to emit an acoustic signal (a pulse, a train of pulses, or a continuous wave) characteristics of which (such as amplitude, frequency, recurrence) are controllable in reference to the US-system frame rate and/or pulse repetition frequency. Relation(s) between, for example an amplitude (or intensity) and timing of the emitted acoustic signal and the US-system frame rate can be selected to make the catheter reproducibly and uniquely identifiable in US Doppler scans regardless of signal attenuation and ambiguity of backscatter patterns. In a specific embodiment, the crystalline element 320 is configured to transmit in an interferometric regime, when a repetition rate and a frequency of acoustic signal(s) generated by the crystalline element are substantially close to those of the PW Doppler modulation of the US-imaging system with which the AAC is being employed. The choice of this specific regime of operation recognizes that (i) an acoustic interference can be created between the PW Doppler signal generated by the imaging system and the signal emitted by the crystal 320 operating in the interference regime; that (ii) this acoustic interference is more pronounced when the crystal is positioned in proximity to or in a Doppler scan plane; and that (iii) the US-imaging system can detect this acoustic interference and uniquely interpret the resulting interference signal as a spatially-localized representation of the tip of the AAC, thereby distinguishing the AAC on the background of images corresponding to a motion of a blood-flow, a motion of the living tissue, or another background motion produced by the anatomic ROI. According to the invention, the imaging system detects the acoustic interference signal and generates an interference output response to the detected signal. The interference output generated by the system is further adopted by the user to navigate the tip of the AAC to a spatial target, such as that marked with a PW Doppler sample window, as discussed below. The output response generated by the system may be, for example, an interferometric image displayed on a monitor device and/or an audible signal generated by the system when the system is appropriately equipped with a digital-to-audio converter. In the following discussion interferometric images are primarily used as examples of the output response of the US-imaging system.

The detection and data-processing of acoustic vibrations produced by the crystal of AAC tip of an embodiment (for example, the crystal 320 of FIG. 3A) can generally be performed as described below. In color-flow Doppler scans, an ensemble of ultrasound pulses can be described by a pulse-repetition frequency (PRF) or the pulse-repetition time interval ($T_{PRF}$), which is an inverse of the PRF. The pulse-echo spatial impulse response of a single-point scatterer, the temporal response of the transducer of the system, the thermal and electronic noise $n(\tau, m)$, and a signal $y(\tau,m)$ received by the US system from the mth transmitted pulse have been described by J. A. Jensen in *J. Acoust. Soc. Amer.*, 89:182-90 (1991) in terms of $T_{PRF}$, the central frequency $f_0$ of the transducer and the speed of sound, c. It follows from that description that both the envelope and phase of the received Doppler signal are modulate with the instantaneous radial displacement of the single-point scatterer (which can be viewed as a single point source). The AAC tip can be confidently approximated as such as single-point scatterer.

It is known that a US transducer can be configured to receive echoes from acoustic interfaces formed due to discontinuities in acoustic impedance at various depths along a path of the acoustic signal towards the ROI. The AAC of the invention can also be operated in the receiving mode advantageously used for navigation of the AAC tip. This embodiment of the invention recognizes that the acoustic field of a flow Doppler scan plane causes the piezoelectric crystal of the AAC to vibrate and produce oscillations representing a highly localized and detectable by the US system signal indicating that the AAC tip intersected the Doppler scan plane. Accordingly, in one embodiment, the AAC tip is navigated through the cardiovascular system based on an acoustic signal received by the crystal of the AAC when the AAC tip is placed within the color-flow Doppler ultrasound scan plane.

Interferometric Tracking of the AAC with the Use of Ultrasound Imaging System

A person skilled in the art would appreciate that, due to the interferometric nature of the interaction between an acoustic wave emitted by the piezoelectric crystal at the tip of the AAC and that of the PW Doppler signal of the imaging system transducer, both the intensity of the resulting interference signal detected by the imaging system and the intensity of the corresponding interferometric image displayed by the system to the user depend inversely on the distance between the tip of the AAC and the chosen Doppler scan plane. A movement of the AAC towards the Doppler scan plane, therefore, is accompanied by an increase of the intensity of the corresponding interferometric signal, while a movement of the AAC away from the Doppler scan plane reduces such intensity. The user can then advantageously exploit this dependency to initially navigate the tip of the AAC towards or away from a Doppler scan plane and, once the resulting interferometric image is acquired, towards or away from a PW Doppler sample window positioned in this Doppler scan plane. While some examples of such navigation are presented below in reference to a cardiovascular system, this particular reference is considered only for the sake of simplicity of explanation and it is understood that, generally, embodiments of the invention are operable within and should be considered with respect to a body and an anatomic target chosen within the body.

Figure 4A:
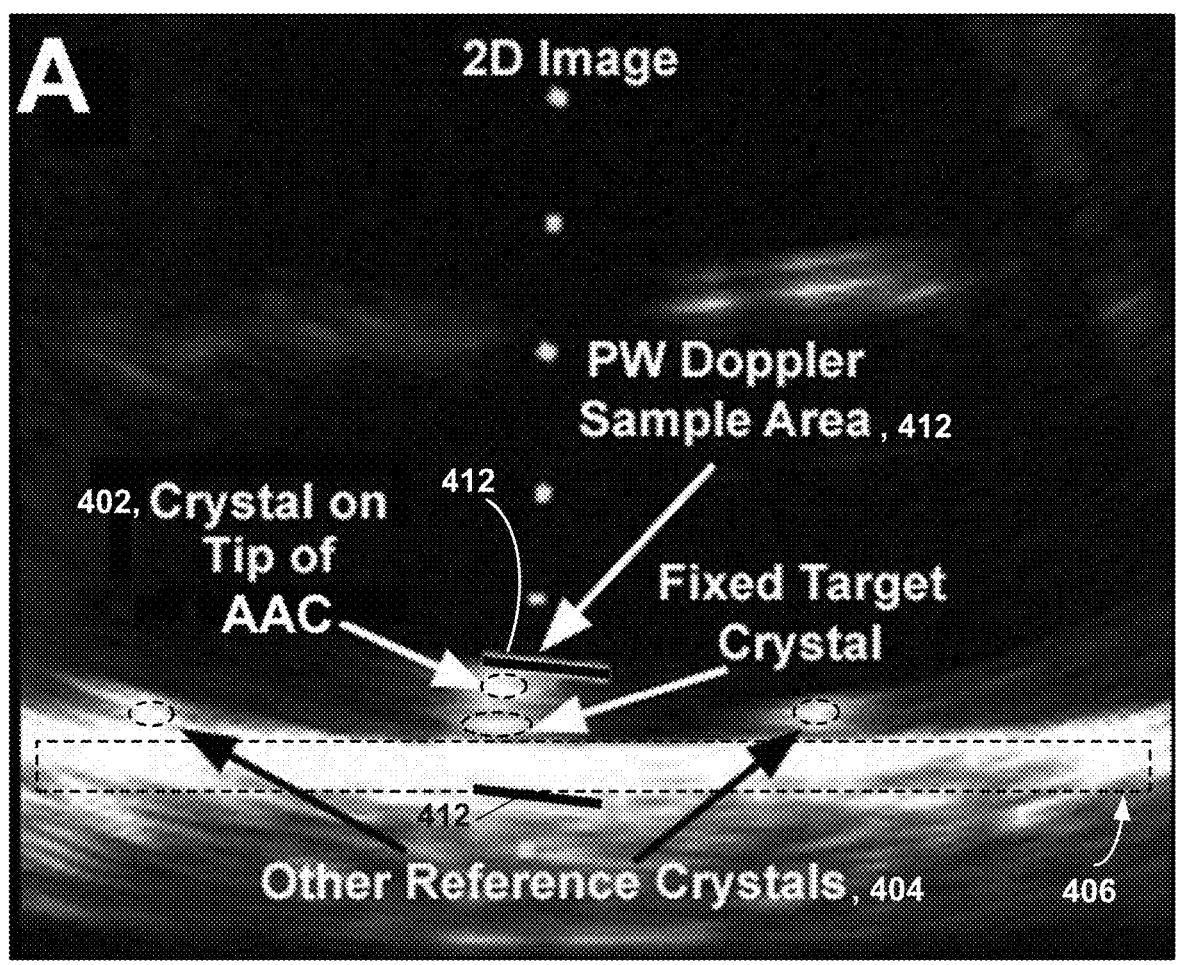
FIG. 4A is an image of a B-mode scan in-vitro using the piezoelectric crystal of an embodiment of the AAC operating as a localized acoustic transmitter, and showing that based on which the crystal cannot be clearly distinguished from the imaging artifacts to be guided by a conventional echo-scan.
Figure 4B:
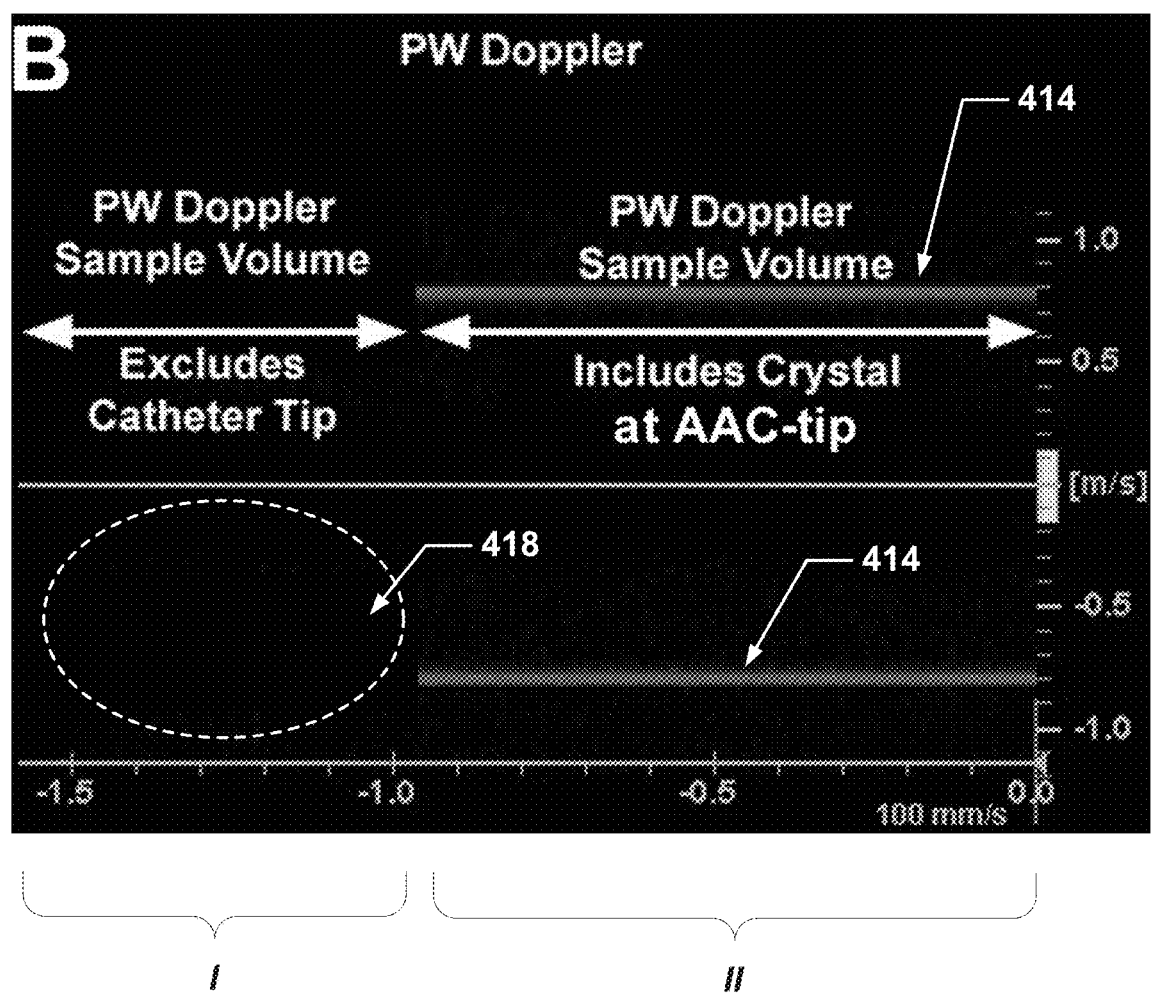
FIG. 4B is a PW Doppler graph created using the piezoelectric crystal of an embodiment of the AAC operating as a localized acoustic transmitter and showing, in comparison, two graphs related to the detected interference (Doppler shift) signals. The display on the left of FIG. 4B (denoted as I) shows no interference (Doppler shift) signal when the crystal at the AAC tip is out of the PW Doppler sample window. The display on the right of FIG. 4B (denoted as II) shows a non-zero Doppler shift signals when the crystal at the AAC tip is located inside the PW sample window or volume.

FIGS. 4A and 4B are images illustrating the application of the above-discussed interferometric regime of operation of the AAC to navigation of the AAC tip to a Doppler scan plane, within a water tank. Here, the ultrasound system is set to a default B-mode scan (1.7 MHz fundamental frequency, 3.4 MHz harmonic frequency) at maximum power. As seen from a conventional in-vitro echo-scan image shown in FIG. 4A and in further reference to FIG. 3A, the tip 322 of the AAC 300, while visually identifiable through its image 402, appears to be substantially similar to images 404 of other piezoelectric crystals and an image 406 of the tissue-density rubber seen at the bottom of FIG. 4A. In FIG. 4A, all of the abovementioned images are outlined with a dashed-line boundary, to facilitate the identification of the images. Overlapped with the image of the B-mode scan of FIG. 4A there is shown a location of a target, a pulsed-wave (PW) Doppler sample window 412. The extraneous images 404, 406 produce visual noise that limits the ability of the operator to precisely navigate the tip of the AAC or to visually differentiate it from other portions of the overall image of FIG. 4A. However, having initially identified the presence of the AAC with the conventional echo-scan image such as that of FIG. 4A, the PW Doppler mode of the US-imaging system can be further used, according to a method of the invention, to interferometrically navigate the tip 322 of the AAC 300 with the activated crystal 320 to the chosen Doppler scan plane. A skilled artisan will recognize that such navigation does not require knowledge of the actual position of the catheter with respect to the target. The proposed method of navigation is not tied to the use of fluoroscopy and is not cost-prohibitive because it may be implemented with commercially-available Doppler echo US systems. The process of navigation turns on a determination of the optimal intensity of the interferometric visual output formed by the imaging system (or, in addition or alternatively, on a determination of the optimal intensity of the interferometric audible output produced by an echo machine of the system.)

FIG. 4B illustrates interferometric images produced as a result of interferometric detection of the activated crystal, of the AAC tip, transmitting a continuous sinusoidal signal with a frequency of 2 kHz and an amplitude of 10 volts peak-to-peak. The right-hand portion II of FIG. 4B shows bright images 414 of interferometric signals produced by the system when the transmitting crystal 320 is positioned exactly within a PW Doppler sample window 412 of FIG. 4A and, at the same time, within the B-mode Doppler scan plane. The left-hand portion I of FIG. 4B shows the absence, 418, of the signal and associated interferometric fringes when the vibrating crystal 320 of FIG. 3A is positioned several centimeters outside of the PW Doppler sample window 412 of FIG. 4A but still within the plane of the Doppler scan. Similarly, the loss or disappearance of the identifying PW Doppler signal occurs if either the AAC tip were completely out of the 2D imaging plane or in the plane but not near the PW sampling window.

It is observed, therefore, that in a PW Doppler mode, the difference between the active AAC tip being within or outside the 2D scan plane is visualized as a detectable change in the strength of the interferometric output produced by the US system. When the crystal at the AAC tip operates by transmitting a continuous sinusoidal wave, placing the PW Doppler sample window 412 over the AAC tip uniquely identifies the AAC tip and distinguishes it from other objects the images 404, 406 of which appear similar to that of the tip in the 2D B-mode image. In this regime, the presence of bright lines 414 on the PW Doppler graph indicates that the AAC tip is located within the PW sample window 412.

Figure 5A:
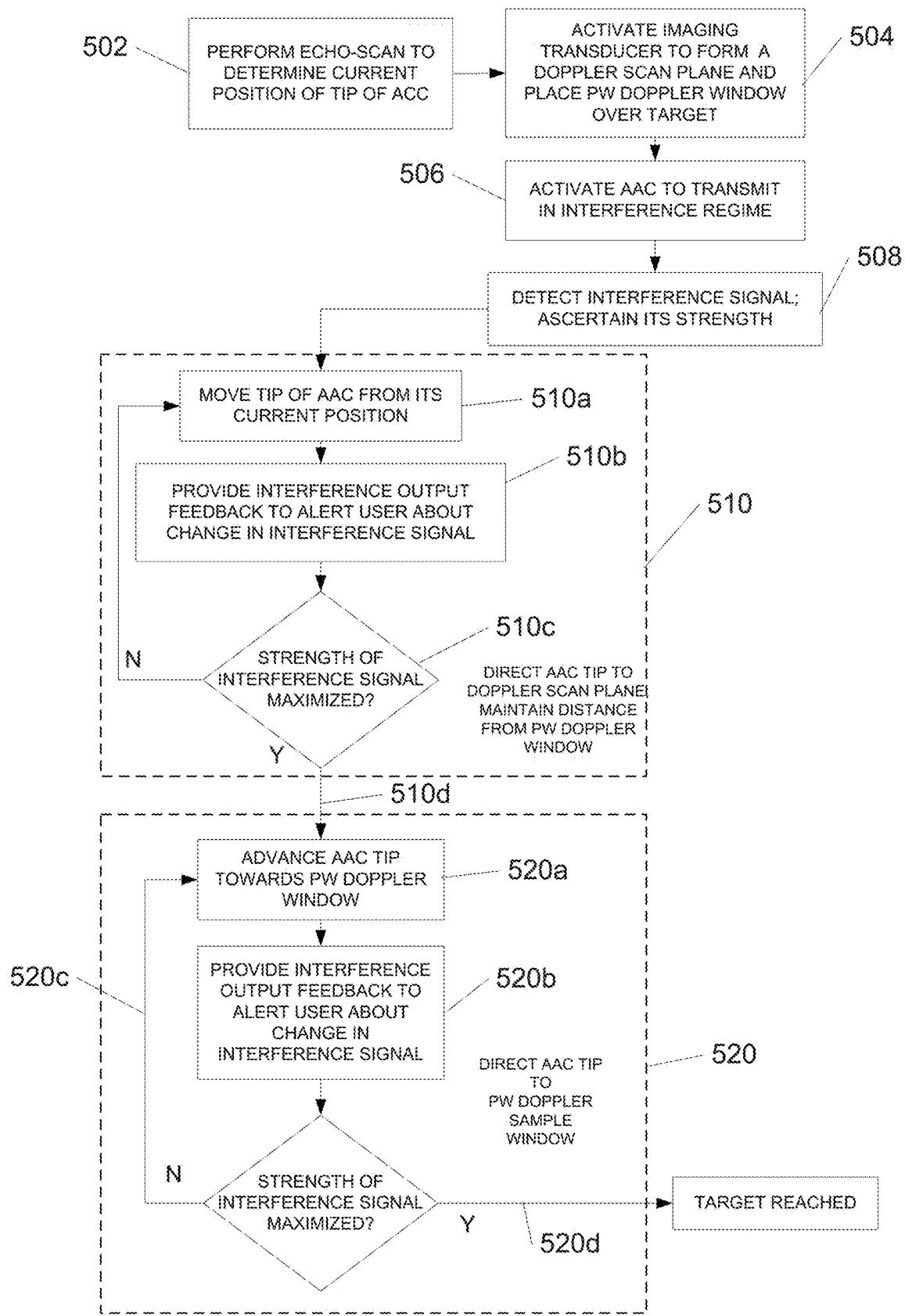
FIG. 5A is a flow-chart showing an algorithm of navigation of an AAC of the invention with the use of interference ultrasonography. Interference (acoustic interaction) between the vibrating crystal at the AAC tip and a Doppler signal transmitted by the US imaging transducer produces Doppler shift signals for identification and navigation of the AAC tip in PW or color Doppler images. A similar functionality but with a crystal vibrating at a different frequency can be used to produce Doppler shift signals for detection and navigation of the needle tip.

FIG. 5A is a flow-chart of the process of AAC tip navigation towards a target located in a Doppler scan plane. Following (or, optionally, contemporaneously with) performing a conventional echo-scan, at step 502, in order to determine an approximate position of the AAC within the vascular system and placing, at step 504, a PW Doppler window in an appropriate spatial location with respect to the chosen anatomic target, the piezoelectric crystal of the AAC is activated at step 506 as a transmitter operating in the interference regime. The interference signal resulting from the acoustic interference between the signal transmitted by the catheter of the invention and the PW Doppler signal is detected, at step 508, by the US imaging system that generates at least one interference output indicating the strength of the detected interference signal. The interference output from the US imaging system may be an image displayed to the user and/or an audible output, as described above. Based on the imaging system output, the user manually or with the help of a computer system directs, at step 510, the tip of the catheter towards a Doppler scan plane produced by the system by iteratively changing the current position of the tip of the AAC at sub-step 510a in such a fashion as to assure that the detected interference signal is increasing, sub-steps 510b and 510c. The change of the position of the AAC tip at this step can be carried out while maintaining the separation distance between the tip of the AAC and the PW Doppler window. When the interference output from the US imaging system indicates, 510d, that the detected interference signal reached its local maximum and, therefore, the AAC tip has been steered to the Doppler scan plane, the user continues the process of AAC tip navigation at step 520 by advancing the AAC tip in the Doppler scan plane towards the PW Doppler window. Similarly to the process of step 510, the advancement of the AAC tip at step 520 may be performed iteratively, 520a, 520b, 520c, based on the interference output feedback by the imaging system that is indicative of the strength of the detected interference signal. When the US system alerts the user that the detected interference signal reached its maximum intensity, 520*d*, the goal of the active navigation of the AAC of the invention is achieved. It is understood that conventional echo-scan based observation of the advancement of the AAC tip can accompany and complement the active navigation of the tip according to the described method.

Figures 5B, 5C:
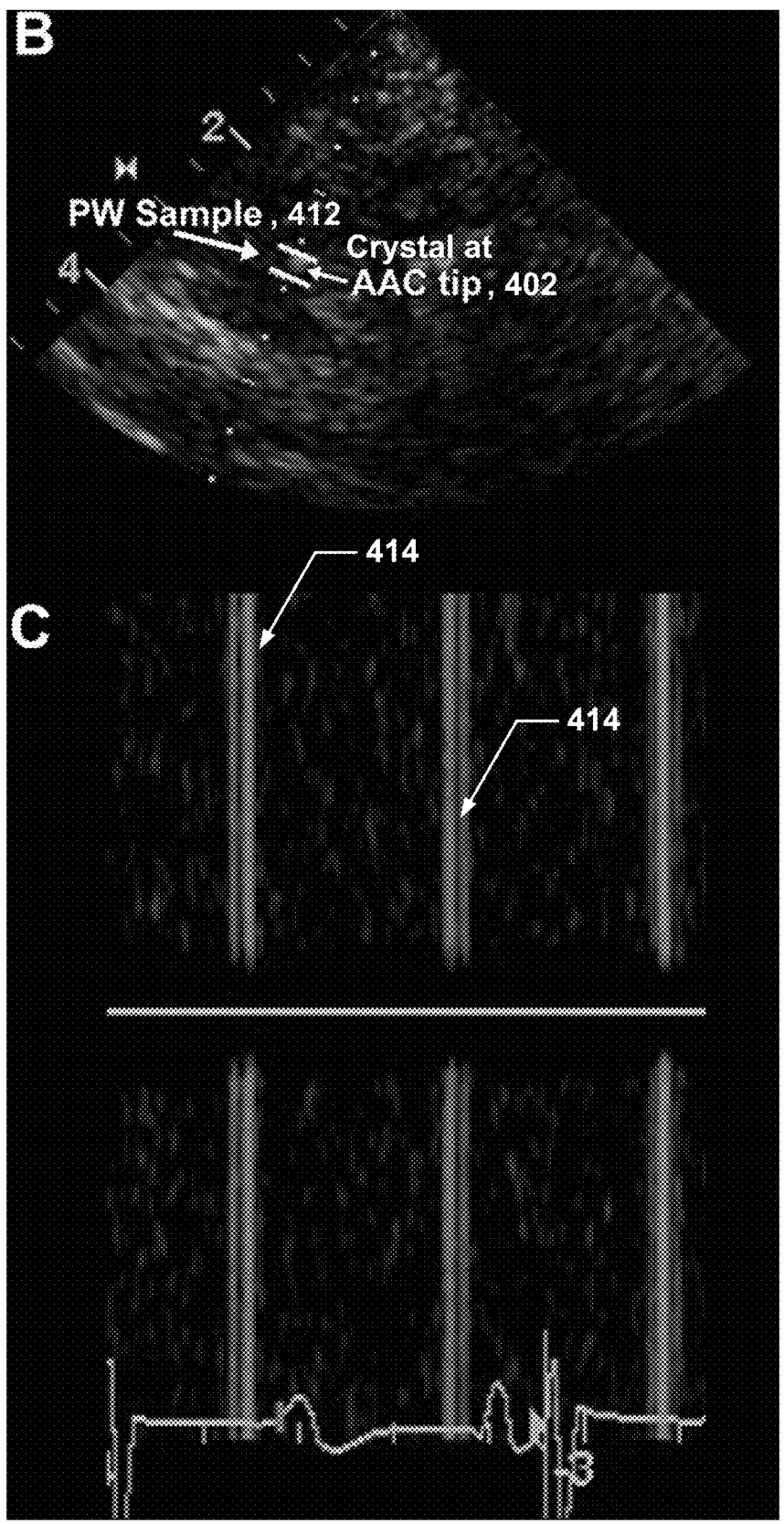
FIG. 5B is a 2D B-mode image representing an in-vivo 2D transthoracic scan of the catheter inside a pig's heart when the AAC tip is within the PW Doppler sample window.
FIG. 5C is a graph corresponding to the image of FIG. 5B and showing, with bright vertical lines, the resulting PW Doppler interference signal that is repeated at the pulse repetition frequency of the signal driving the AAC.
Figures 5D, 5E:
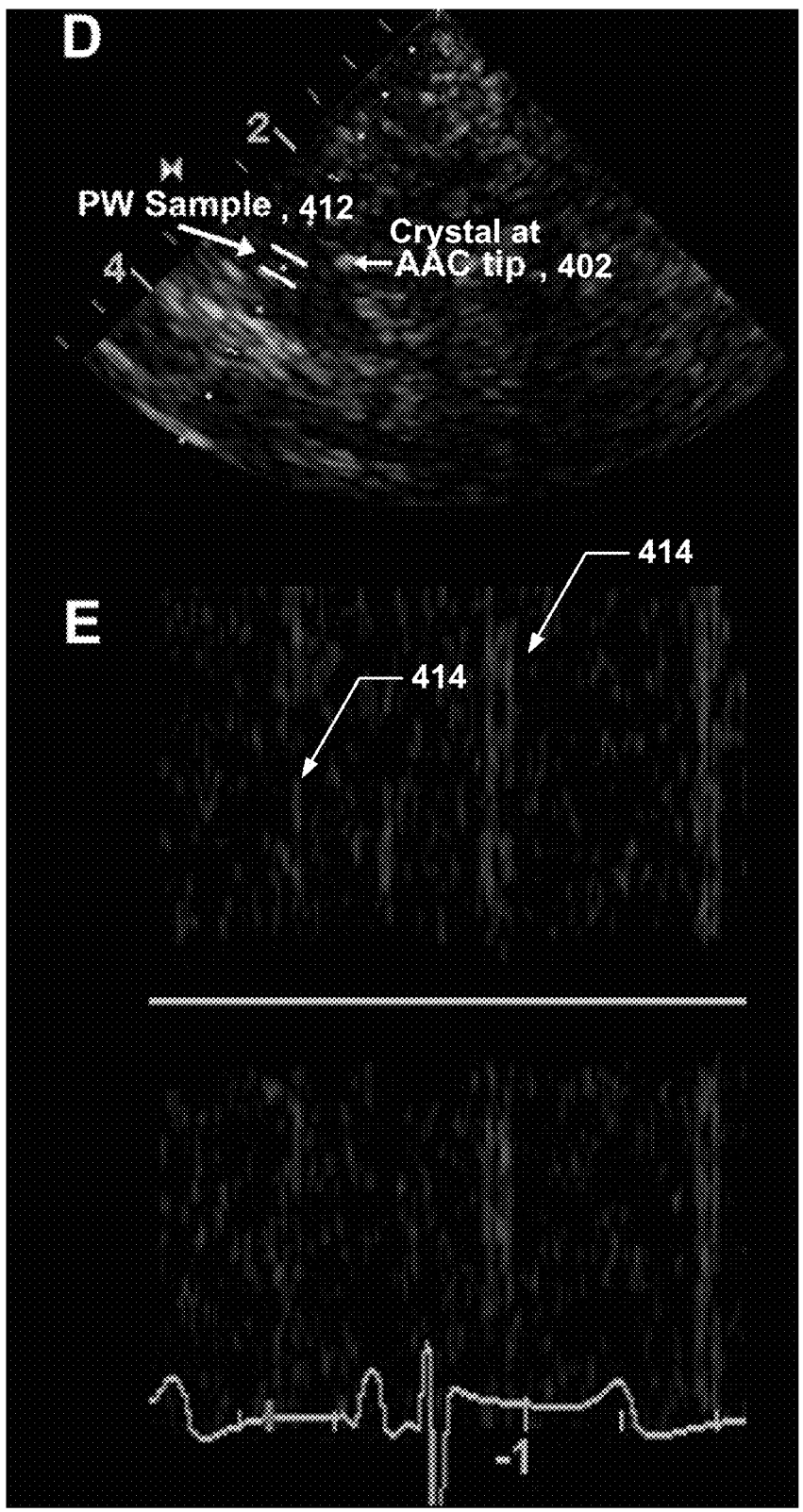
FIG. 5D is a 2D B-mode image representing an in-vivo 2D transthoracic scan of the catheter inside a pig's heart when the AAC tip is outside the PW Doppler sample window still within the 2D-imaging plane.
FIG. 5E is a graph corresponding to the image of FIG. 5D and showing a weakened interference signal.

FIGS. 5B, 5C, 5D, and 5E additionally illustrate an application of the interferometric navigation of the AAC tip using the method of the invention. FIG. 5B demonstrates a transthoracic US scan (2D B-mode image) of the AAC tip placed inside a beating porcine heart in situ. As can be seen from the corresponding FIG. 5C, the intensity of the navigation interference signal 414 has substantial intensity and is easily perceived when the tip is steered into the target area represented by the PW sample window 412. In contradistinction, as shown in FIGS. 5D and 5E, when the AAC tip is outside of the PW sample window 412, the interference signal 414 is weakened, and its brightness is drastically reduced, as shown in FIG. 5E (PW Doppler graph). FIGS. 5D and 5E show the same pig experiment as in FIGS. 5B and 5C but now with the AAC tip outside the target area. During this experiment, the AAC tip was being driven by an (actively transmitting) gated rectangular (square-wave) signal with a frequency of 1.3 kHz within each chirp (pulse) and a pulse repetition frequency of 2 Hz. The difference between the orientation of the display of the interference signal in FIG. 5C (vertical orientation) and that of FIG. 4B (horizontal orientation) is due to the difference of the signal driving the AAC, i.e, a gated square wave (FIG. 5C) versus a continuous sinusoidal wave (FIG. 4B). Here, the US imaging system is additionally configured to generate a clicking audible signal output, the amplitude of which depends on the motion of the AAC tip with respect to the target and allows the user to navigate the AAC tip exclusively in reliance on the intensity of the audible signal.

The above-discussed principle of the catheter navigation towards a single Doppler scan plane can be appropriately extended, according to the idea of the present invention, to a 3D navigation of the AAC. In one embodiment, for example, the 3D navigation can be implemented by generating two intersecting Doppler scan planes with a transducer imaging the 3D space in a real-time bi-plane mode, in a time-sequenced stream of spatial image data. In a specific embodiment, these planes may be mutually orthogonal. For the purposes of this disclosure and accompanying claims, a real-time act performed by a system is understood as an act that is subject to operational deadlines from a given event to the system's response to that event. For example, generation of two Doppler scan planes in real-time is understood to be contemporaneous with the process of catheter navigation, while comparison of data in real-time may be one triggered by the system and executed simultaneously with and without interruption of operation of the system during which such comparison is being performed.

Figure 6A:
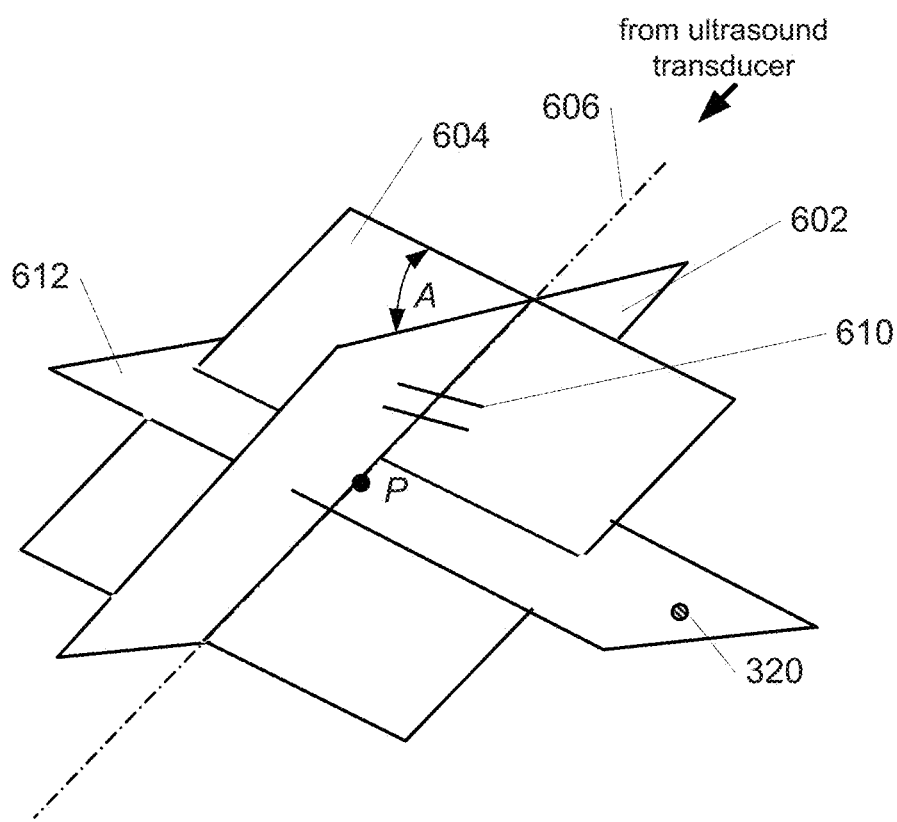
FIG. 6A is a flow chart schematically illustrating a method of the invention to interferometric navigation of the AAC tip with respect to two mutually intersecting Doppler scan planes.

The principle of interferometric navigation of the AAC of the invention in reference to two Doppler scan planes 602 and 604 is further illustrated in FIG. 6A. The Doppler scan planes 602 and 604 are generated by and associated with a transducer (not shown) operating in a 3D-scanning mode. These Doppler scan planes intersect each other along an axis 606 at a dihedral angle A. FIG. 6A also schematically shows the crystalline element 320 that is configured to operate in the interference regime and is affixed to the AAC tip (not shown). On top of the Doppler scan planes 602, 604 there is shown a PW Doppler sample window 610 that in practice may overlap with and correspond to the position of the chosen anatomic target.

It is appreciated that the virtual axis 606 is a locus of points that are located in both Doppler scan planes 602 and 604. Therefore, the strength of a first acoustic interference signal (that is detected by the US imaging system when the transmitting crystal 320 of the AAC 300 of FIG. 3A is placed at a reference point P on the axis 606) exceeds the strength of any other acoustic interference signal (that is detected when the transmitting crystal is placed at any other point located in a plane 612 through which the axis 606 passes perpendicularly at the reference point P). As a result, the AAC tip with a crystal 302 (such as the tip 322 of the embodiment 300 of FIG. 3A) transmitting in the interference regime can be actively navigated and the navigation can be controlled (by maximizing the strength of the interference output generated by the US-imaging system as described in reference to FIG. 5A) from its instantaneous location in the plane 612 towards its designated location P on the axis 606. This navigation may include, for example, initially directing the crystal into a first of the Doppler scan planes (such as the plane 602) and then further directing the crystal along that first scan plane towards another Doppler scan plane (such as plane 604), thereby navigating the crystal (and, therefore, the tip of the AAC) along the axis 606 defined by the intersecting planes 602 and 604.

Figure 6C:
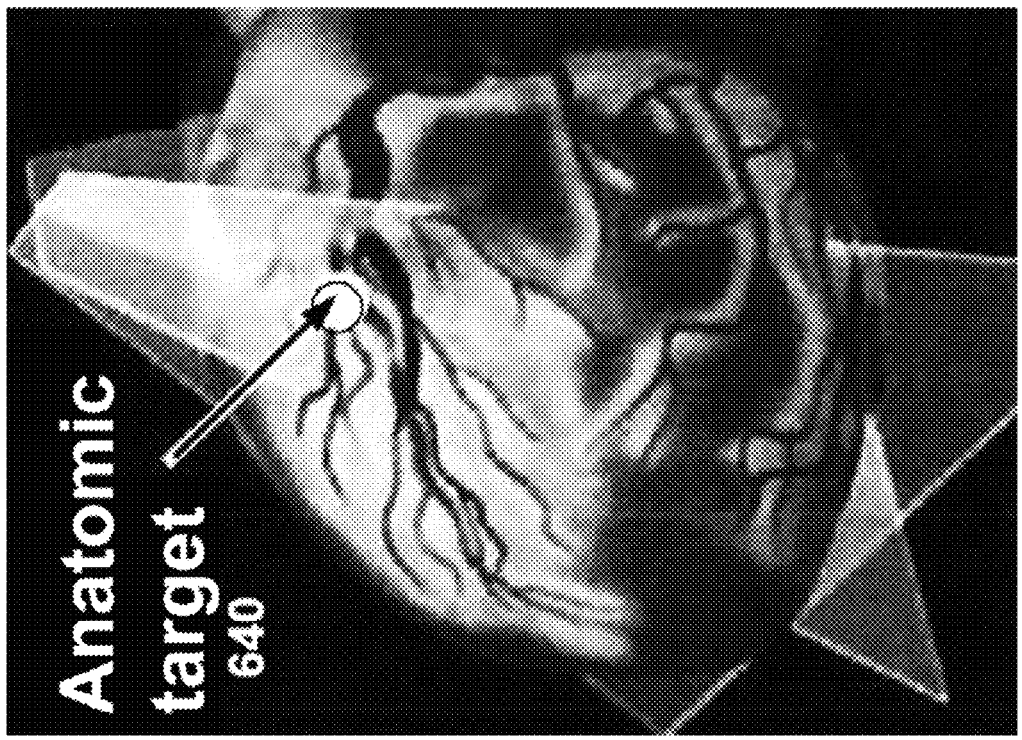
FIG. 6C is a picture schematically showing a biplane Doppler scan arrangement centered on an anatomic target.
Figure 6B:
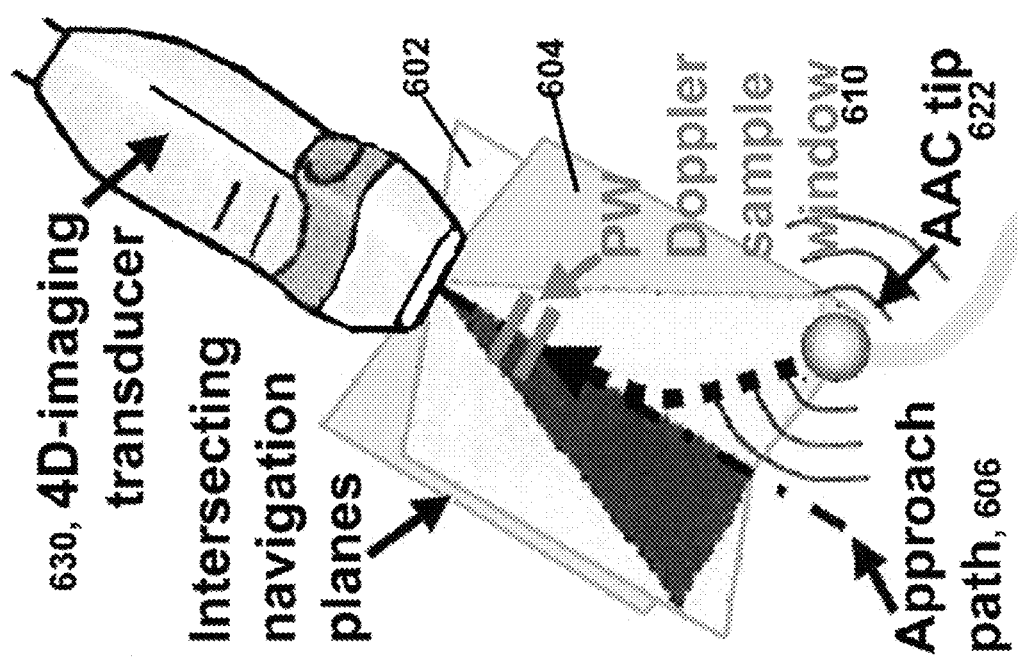
FIG. 6B is a picture illustrating two mutually intersecting Doppler scan planes formed by a four-dimensional (4D; 3 spatial dimensions in real time) imaging transducer and a path of navigation of the AAC tip towards and along an intersection axis.

In practice, a 3D interferometric navigation can be used, for example, to pilot the AAC tip to a point at the endocardial surface that is the closest to the epicardial anatomic target. In reference to FIGS. 6B and 6C, the two Doppler scan planes 602, 604 are projected by a 3D-imaging transducer 630 onto an anatomic target 640 such as the coronary artery in the LV cavity. The AAC tip 322 with the crystal 320 is directed towards the target 640 from inside of the LV along the navigation planes 602, 604 and the intersection axis 606 with a purpose of approaching the target. The determining positions and advancement of the AAC tip within the cardiovascular system towards the target is indicated by increasing intensity of the "navigation signal" (which is either an interference image or audible interference signal) when the AAC tip is positioned within one of the Doppler scan planes (602 or 604). By ascertaining the strength of two interference signals respectively corresponding to relative position of the AAC tip with respect to the planes 602 and 604, the AAC tip is directed towards the "navigation path" (the axis 606) and is further advanced, as confirmed by a continuously increasing interference signal, towards the PW Doppler sample window that has been appropriately spatially overlapped with a target. In addition or alternatively, the PW Doppler sample window can be positioned in the proximity of the actual anatomic target, for example at the nearest point on the endocardial surface, so as to cause the US imaging system to generate the maximum interference signal prior to an accidental piercing the LV wall with the AAC tip. As a result, the determination of positions of the catheter tip within the cardiovascular system is carried out in response to the detected acoustic interference signal. The ceasing of the advancement of the AAC tip during its navigation prior to such accidental piercing of the LV wall can be additionally verified by accounting for the thickness of the LV wall that is simultaneously depicted by and measured with the use of a conventional echo-scan.

Figure 7:
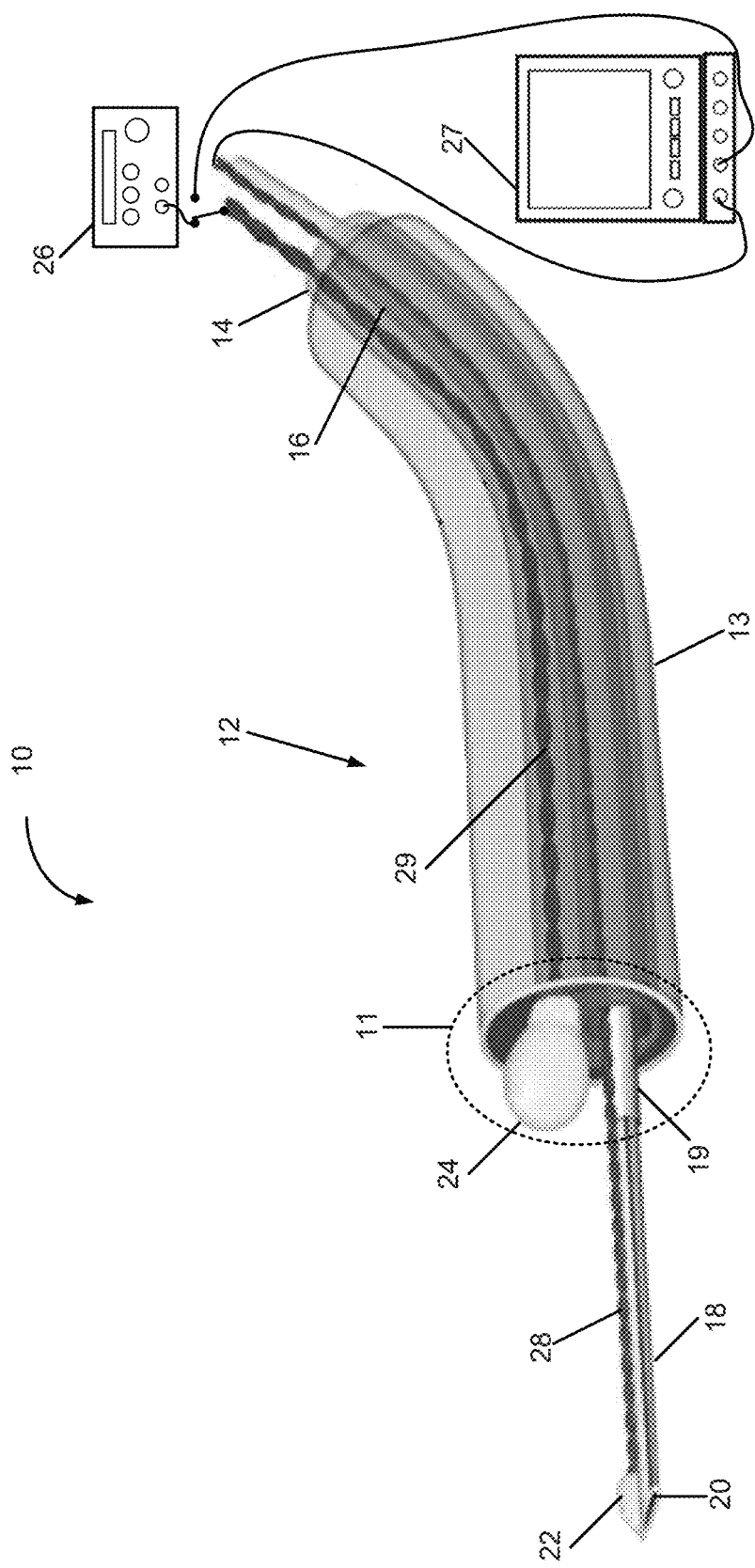
FIG. 7 is a schematic of the AAC system with a detailed depiction of a tip of an injection catheter according to the present disclosure.

Referring to FIG. 7, a system 10 includes an acoustically active catheter 12, or AAC, with injection capabilities and an electrical connection between the AAC 12 and a waveform generator 26 and a system 27. The system 27 may be a sonometry instrument, an Doppler ultrasound imaging system, or any other ultrasound system. It is possible for the electrical connection to be a wired connection as described below, however the electrical connection may also be a wireless communication between the AAC 12 and the waveform generator 26 and the sonometry instrument 27. The acoustical property of the system 10 allows navigation of a catheter tip 11 to a desired anatomic location by means of a crystal 24. The catheter tip includes a retractable needle 18, which can be exposed to a measurable length for depth-controlled injections.

The AAC 12 includes a steerable sheath 13 that covers an outer tube 14. The outer tube 14 contains in its lumen a connecting electrical wire 29 for the crystal 24 and an inner tube 16. The inner tube 16 includes in its lumen a slidable microtube 19 and a connecting electrical wire 28 for a microcrystal 22. A needle 18 is connected to the distal end of the slidable microtube 19. By sliding back or forth, the microtube 19 retracts or exposes the needle 18 into or out of, respectively, the distal end of the inner tube 11. Because the distal end of the inner tube 16 is flush with the catheter tip 11, sliding with the microtube 19 can expose the needle from the catheter tip 11 to a desired exposure length. A distal tip 20 of the needle 18 is outfitted with a microcrystal 22. A connecting wire 28 for the microcrystal 22 is placed along (or could be made to run within the wall or inside the lumen of) the needle 18 and the microtube 19.

The crystals 22 and 24 can be made of lead zirconate titanate (PZT) or polyvinylidene fluoride (PVDF). The crystal 24 can be approximately 2 mm in diameter, whereas the crystal 22 can be smaller, perhaps 1 mm in diameter or less. Because, in the presented example system illustrated in FIG. 7, the crystal 22 is smaller, it is referred to as a "microcrystal" for a descriptive clarity and distinction from the other crystal 22. However, the prefix "micro" is used herein solely for a descriptive clarity. There is no predetermined size of either of the crystals 22 and 24. The actual size and whether one crystal is bigger than the other would depend on a particular application of the invention.

The crystal 24 may be configured to generate different prescribed signals and, therefore, the AAC system 10 can operate in different modes, referred to as an Operating Mode A, an Operating Mode B, and an Operating Mode C. The Operating Mode A provides for detection and navigation of the catheter tip, whereas the Operating Mode B and an Operating Mode C may be used to provide for depth-controlled injections.

In the Operating Mode A, the crystal 24 serves as an acoustic navigation marker. The crystal 24 may be driven by an electrical signal to produce the acoustic signal. An electrical wiring 29 electrically connects the crystal 24 via a switch 25 to a waveform generator 26. The crystal 24 may be driven by a periodic signal of frequency f1 using the waveform generator 26. An ultrasound transducer can be used to interrogate the vibrating crystal 24 with a Doppler signal having a frequency fD. An ultrasound pulser in the ultrasound imaging system controls the timing and frequency of the signal transmitted by the transducer to generate desired ultrasound pulses that form the Doppler signal.

More in particular, in the Operating Mode A, the ultrasound pulser may have a variety of pre-programmed options for number of pulses in a group, signal frequency, etc. The ultrasound waves are generated in a pulsed mode wherein wave pulses comprising a relatively small number of waves are generated in spaced packets that are separated in time by periods with no signal generation. The ultrasound transducer may be operable to both generate ultrasound waves (that is, vibrate in response to an applied current) and to detect ultrasound waves (that is, generating a current in response to ultrasound pressure waves). Ultrasonic waves generated by the transducer can be focused directionally into a relatively narrow beam, a process sometimes referred to as beamforming. Such focusing may be accomplished by electronic beamforming, or by the shape of an acoustic lens disposed in front of the transducer, or by a combination of the electronic beamforming and the acoustic lens.

Furthermore, in the Operating Mode A, interaction of the Doppler signal having the frequency $f_D$ with the crystal 24 vibrating at the frequency $f_1$ produces localization signals with frequencies $f_D+f_1$ and $f_D-f_1$, respectively. The localization signals can be received by the ultrasound transducer, interpreted by the ultrasound imaging system as Doppler shifts, and displayed by the ultrasound imaging system as two unique constant velocities. The waveform generator 26 may achieve effective and unambiguous localization signals by producing $f_1$ at various frequencies and modulation schemes. One of many such examples of $f_1$ can simply be a sinusoidal signal within an audible frequency of 1 kHz. Whereas, $f_D$ produced by the ultrasound transducer can be set, for example, to 1 MHz. Using this practical example and assuming an average speed of sound within a human body of 1540 m/s, the resulting localization signals produced by the Doppler ultrasound system after interaction with the vibrating crystal 24 may be (based on a fundamental Doppler equation) equal to −0.77 m/s and +0.77 m/s.

Furthermore, in the Operating Mode A, the presence of the localization signals indicates that the crystal 24 is within both the Doppler plane and the pulsed-wave (PW) sample window. If the catheter tip 11 moves out of the Doppler plane or away from the PW sample window, the navigation signal is interrupted or disappears. By using various frequencies and modulations of $f_1$, the first and second localization signals for the catheter tip 11 appear on the Doppler ultrasound image screen or could be heard from speakers of the ultrasound imager. Either way, such signals can be made easily and unambiguously distinguishable from signals generated by variable velocities of blood flow or by relatively slow tissue velocities of a beating heart or pulsating blood vessels. Therefore, spatial detection of the crystal 24 can be made when depiction of anatomy is suboptimal or the navigated acoustically active catheter 10 is blurred or shown sparsely by conventional (B-mode) ultrasound imaging, and constitutes the navigation Operating Mode A of the crystal 24. Placement of the crystal at the catheter tip 11 allows localization and navigation of the acoustically active catheter 10 within three-dimensional space of cardiovascular anatomy; however, numerous other than cardiovascular applications and implementations of a variety of minimally invasive tools are enabled by the present invention as well.

In the Operating Mode B, the second signal may be produced by the purposefully placed first and second acoustic markers (crystals) and serves for acoustic communication between the two markers. The markers may alternate in their role of producing the second signal. That is, the first acoustic marker may act as a transmitter and the second acoustic marker as a receiver or, alternatively, the second acoustic marker may act as a transmitter and the first acoustic marker serves as a receiver of an acoustic signal. This process can determine mutual distance between the acoustic markers and is called sonometry. Based on acoustic communication between the first and second acoustic markers, the sonometry system may measure needle exposure length for depth-controlled injections.

For example, the crystal 24 may be treated as the first acoustic marker and the microcrystal 22 may be the second acoustic marker. Thus, the crystal 24 and microcrystal 22 are driven by the sonometry system 27. An electric signal of frequency $f_2$ applied alternatively to the crystal 24 or microcrystal 22 results in acoustical signals of frequency $f_2$ transmitted by one of the crystals and received by the other.

More in particular, in the Operating Mode B the crystal 24 is electrically connected via a wiring 29 and a switch 25 to a sonometry instrument 27. Microcrystal 22 is connected via a wiring 28 to the sonometry instrument 27 as well. The crystal 24 at the catheter tip 11 and the microcrystal 22 at the needle tip 20 are used to measure an instantaneous length of needle exposure from the catheter tip 11, when the needle is not retracted into the inner tube 16. In one intended application, the catheter tip 11 (and, thus crystal 24) touches the inner surface (endocardium) of the LV wall. By transendocardially inserting the needle with the microcrystal 22 at its tip into myocardium of the LV wall, the exposure length of the needle 18 is obtained as the distance between the crystal 24 and microcrystal 22. The distance between the two crystals is an instantaneous measure of the intramyocardial injection depth. Thus, based on the strategic placement of the crystal 24 and the microcrystal 22, the AAC system 10 working in the Operating Mode B can provide instantaneous measurements of the needle 18 exposure lengths and allow depth-controlled injections.

Furthermore, in the Operating Mode B, each of the two crystals 24 and 22 may be operable to both generate ultrasound waves (that is, vibrate in response to an applied current) and to detect ultrasound waves (that is, generating a current in response to ultrasound pressure waves). This alternating transmission and reception of an ultrasound signal by the microcrystal 22 and crystal 24 allows for their mutual acoustic communication and measurement of instantaneous distance between the two crystals. An ultrasound signal pulse, for example of frequency $f_2=1$ MHz, may be emitted from the microcrystal 22 and received by the crystal 24. Or, an ultrasound signal pulse of the same frequency may be emitted from the crystal 24 and received by the microcrystal 24. Transmission of the repetitive pulses could be originating from one crystal only and by receiving by the other crystal only. However, more typically, the crystals may alternate in their pulse emitting and receiving functions, because it allows for checking on the consistency of the measured mutual distance.

More in particular about mutual distance measurement in the Operating Mode B, the speed of sound within the human body is known or can be closely estimated (a practical representative value is 1540 m/s). Using a time-of-flight principle and the value of the sound speed in the human body, a mutual distance between two crystals can then be calculated from a time delay between generating the pulse by one crystal and receiving that pulse by the other crystal. This constitutes the Operating Mode B of crystal 24 in conjunction with the microcrystal 22 for measurements of needle 18 exposure lengths because the microcrystal 24 is at a constant position with respect to the needle tip 20, whereas the crystal 24 is in a constant position at the catheter tip 11.

Furthermore, in the Operating Mode B of the described system, the sonometry instrument 27 produces pulses typically in a rate of hundreds of Hz and, therefore, enables hundreds of measurements per second of the distance between the two crystals. Such rate supports real-time measurement of intramyocardial injection depth in the presented cardiac application. The time-of-flight method of measuring the distance between two ultrasound-transmitting crystals is well established and termed sonometry. The sonometry instrument 27 may be a commercial sonometry system, which may be adapted to carry out the sonometry method described herein for measuring the needle exposure length by a microcrystal 22 located at the needle tip 20.

Figure 18:
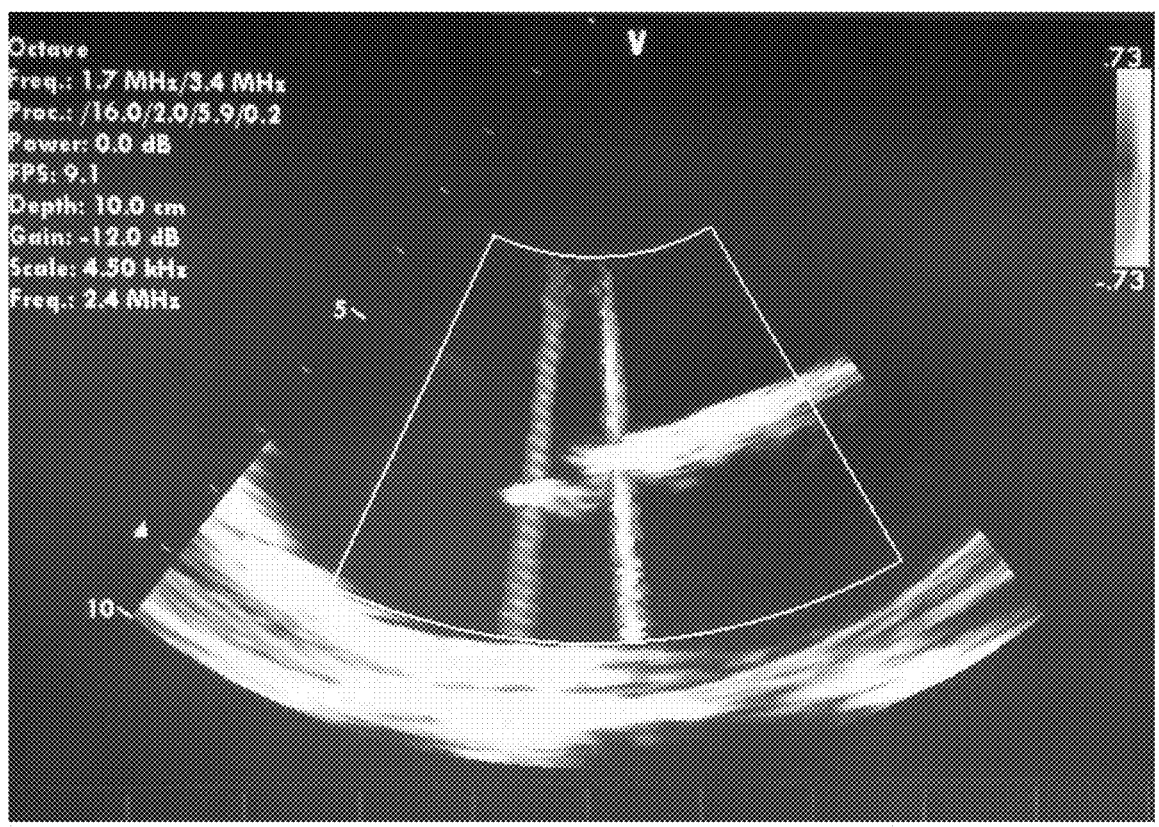
FIG. 18 shows an example color Doppler image indicating the location of a needle and a catheter tip by simultaneously generated but independent color markers.

In the Operating Mode C, the system 27 may be a Doppler ultrasound system. The crystal 24 and the microcrystal 22 may generate acoustic signals at different frequencies. The Doppler ultrasound system 27 may display the positions of the catheter tip and the needle tip using the different interference signals simultaneously on the display using different colors. In other words, there would be a color Doppler marker of the needle tip and another color Doppler marker of the catheter tip (FIG. 18). The interference signals may be caused by the interaction of acoustic signals generated by a transducer of the Doppler ultrasound system 27 and the two acoustic signals generated by the crystal 24 and the microcrystal 22. The Doppler ultrasound system 27 may include one or more filters to filter the two desired interference signals and suppress the undesired signals from the background tissues or other sources.

Figure 8:
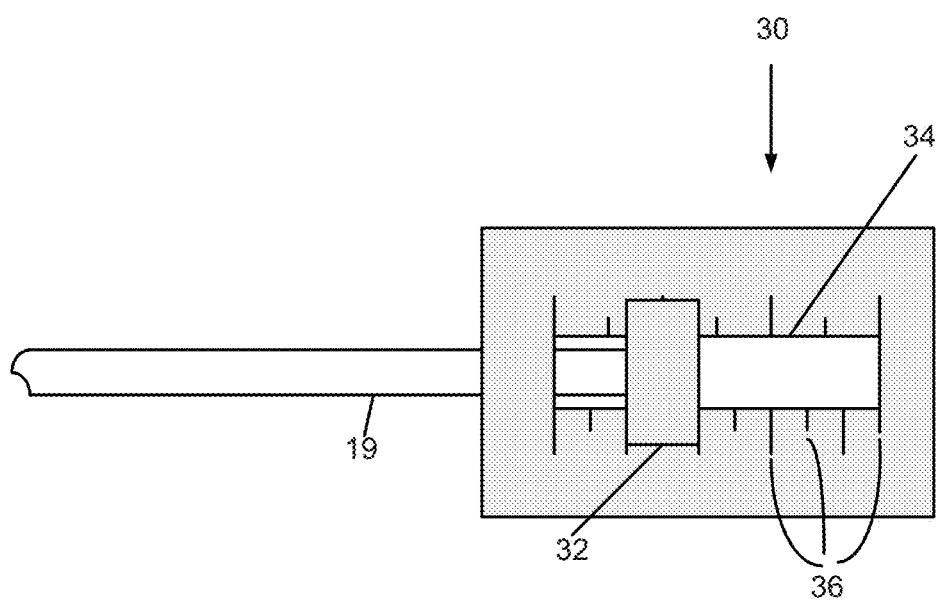
FIG. 8 is a schematic of a handle for positioning a needle according to the present disclosure.

Referring to FIG. 8, the AAC system 10 may also include a handle 30 at a proximal end of the catheter 12. The handle 30 is configured to expose or retract the needle 18 when manipulated by a user. The handle 30 may have a slider 32 connected to the needle 18 by tubing 19 and configured to expose the needle 18 by a defined length. The needle 18 can be exposed or retracted by translating the slider 32 along a track 34. The handle can be calibrated with a plurality of calibration marks 36 such that the user can approximate the distance of the needle tip 20 relative to the catheter tip 11, that is, can approximate the exposure length of the needle 18. Therefore, the handle 30 with the slider 32, track 34, and calibration marks 36 is practical for exposure and retraction of the needle 18. However, the actual instantaneous exposure length of the needle 18 is given by the distance between the needle tip 20 and the catheter tip 11. Such distance is obtained by sonometry between the microcrystal 22 and crystal 24, respectively, and in the currently-described example, represents the intramyocardial injection depth. This novel injection depth measurement principle can be used in a variety of applications other than the presented example of transendocardial insertion of the needle into the LV wall.

Figure 9A:
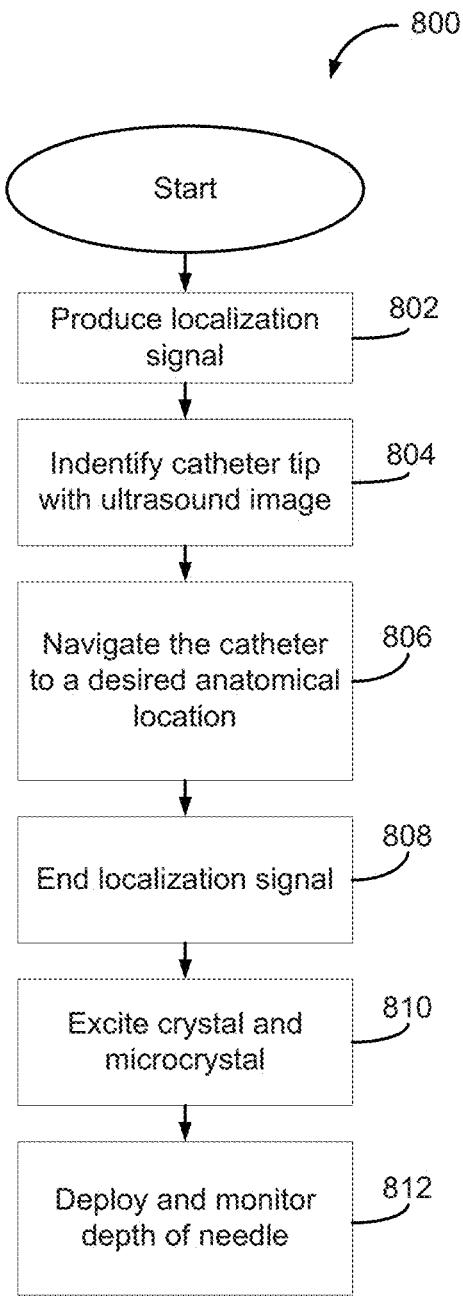
FIG. 9A is a process flowchart for a method of delivering a needle to an anatomical location and monitoring the injection depth of a needle.

Referring to FIG. 9A, a flowchart illustrating a process 800 for navigating the AAC 12 and depth-controlled injection of the needle tip 20 is shown. The crystal 24 may be excited using the waveform generator 26 at a frequency $f_1$, and a Doppler waveform having a frequency $f_D$ may be used to interrogate the excited crystal 24. Localization signals due to interaction of the Doppler waveform and the waveform from the waveform generator may be produced as shown in step 802. An ultrasound transducer may receive the localization signals, allowing for imaging and identification of the excited crystal 24 and the catheter tip 11 as seen in step 804. The ultrasound image of the catheter tip 11 may be used to assist navigation of the AAC 12 to a desired anatomical location, as can be seen in step 806. The localization signal produced by the waveform generator 26 may be terminated as shown in step 808, and an excitation signal produced by the sonometry instrument 27 may be produced as shown in step 810. The sonometry instrument may be configured to repetitively and alternately excite the crystal 24 and the microcrystal 26. It is also possible for the sonometry instrument to be configured to repetitively excite only one of the crystal 24 and the microcrystal 26. The excitation of the crystal 24 and the microcrystal 26 allows for determination of the instantaneous depth of the needle 18. The needle 18 may be inserted into the anatomical target, and the real-time depth of the tip of the needle 18 relative to the distal end of the AAC 12 may be monitored as seen in step 812.

Figure 9B:
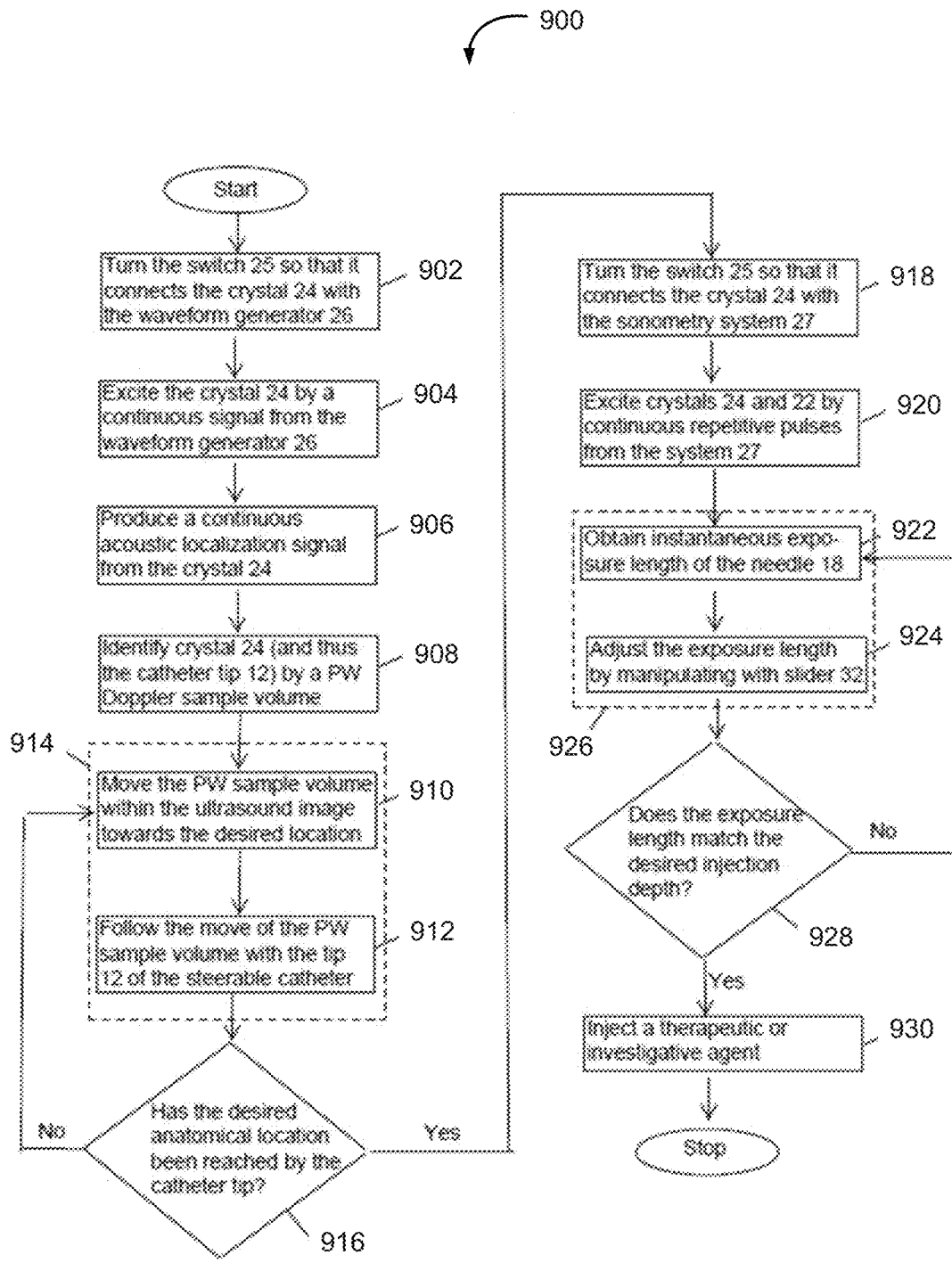
FIG. 9B is a process flowchart setting forth some examples of steps of a method for delivering a needle to a desired anatomic location and determining the depth of a needle according to the present disclosure.

Referring to FIG. 9B, an example process 900 for navigating the catheter tip 11 to a desired anatomic location and delivering a needle to this location for a depth-controlled targeted injection of a therapeutic or investigative agent is shown. As can be seen in step 902, the switch 25 is turned so as to connect the waveform generator 26 with the crystal 24. In step 904, the waveform generator excites the crystal 24 by a continuous signal and leads to crystal vibrations. In step 906, the interaction of the vibrating crystal 24 with a Doppler ultrasound beam produces a continuous acoustic localization signal that is received by an ultrasound transducer. In step 908, the crystal 24 is identified within the Doppler imaging plane and within the PW Doppler sample window located in that imaging plane. Because the crystal 24 is permanently attached to the catheter tip 11, the step 908 actually identifies the catheter tip. The identification is based on an unambiguous, visible and audible, signal produced by the ultrasound system operating in the PW Doppler mode. In step 910, the PW sample window is interactively moved towards the desired anatomic location (in the PW Doppler mode, the anatomic ultrasound image is simultaneously shown). In step 912, the catheter is navigated, by means of steering and advancing the distal end of the catheter towards the PW sample window until the localization signal is obtained, thus confirming that the catheter tip 11 is contained within the PW sample window. The succession of steps 910 and 912 constitutes a procedure 914, that is, navigation of the catheter tip 11 by an ultrasound imaging system operating in the PW Doppler mode. In step 916, the user determines whether the desired anatomic location has been reached by the catheter tip 11. If not, the navigation procedure 914 is repeated until the PW sample window is at the desired location and the catheter tip 11 is identified within that sample window. During catheter navigation, the microcrystal 22 is not active and the needle 18 is completely retracted within the lumen of the inner tube 16 so that the needle and microcrystal 22 are protected and the sharp tip of the needle cannot cause an accidental injury during catheter navigation. One practical application of the procedure 914 would be navigation of the catheter tip 11 into a contact with the inner surface of the LV wall at a location of myocardial infarction.

FIG. 9B further shows steps after the desired anatomic location has been reached by the catheter tip 11. In step 918, the switch 25 is turned so that it disconnects the crystal 24 from the waveform generator 26 and connects the crystal to the sonometry instrument 27. The microcrystal 22 is already directly connected to the sonometry instrument 27. In step 920, the sonometry instrument 27 alternatively excites crystals 24 and 22. In step 922, instantaneous exposure length of the needle 18 is obtained. Because the needle would typically be retracted into the lumen of the inner tube 16 at the start of step 922, the needle is exposed to a certain exposure length from the inner tube 16 in step 924. Steps 922 and 924 constitute a depth-controlled needle insertion procedure 926, because by further exposing the needle from the inner tube, the needle is inserted into the anatomic location. In our practical example, the catheter tip is in contact with the inner surface of the LV wall and, therefore, the needle is inserted into the myocardium. The needle exposure length procedure 926 can be accomplished by utilizing either the operating Mode B or the operating Mode C. If the operating Mode B is use, then 926 is a sonometric procedure, as described earlier. If operating Mode C is used in the procedure 926, it means that the needle is exposed to a particular length based on real-time visual identification of the needle tip by a color Doppler marker as the needle is being inserted into the cardiac wall. Also, that color Doppler marker would show the spatial relation (distance) of the needle tip with respect to an independent color Doppler marker of the AAC tip. FIG. 18 shows how two independent color Doppler markers, one indicating the needle tip and the other indicating the AAC tip, may look like.

In step 928, the user determines, based on the instantaneous exposure length of the needle, whether the needle tip reached the desired injection depth. If not, the procedure 926 is repeated. If yes, the needle has been delivered into the desired anatomic location and depth-controlled injection of a therapeutic or investigative agent can be performed in step 930. This step concludes the entire process 900, that is, the method of navigating a catheter tip for delivering the needle to a desired anatomic location and performing a depth-controlled injection into that location. In our practical application, a therapeutic or investigative agent could be deposited via the inserted needle into the intramyocardial location of infarction.

EXAMPLES

Example 1

(FIG. 10)—Precision and Accuracy of Needle Sonometry in Water

Figure 10:
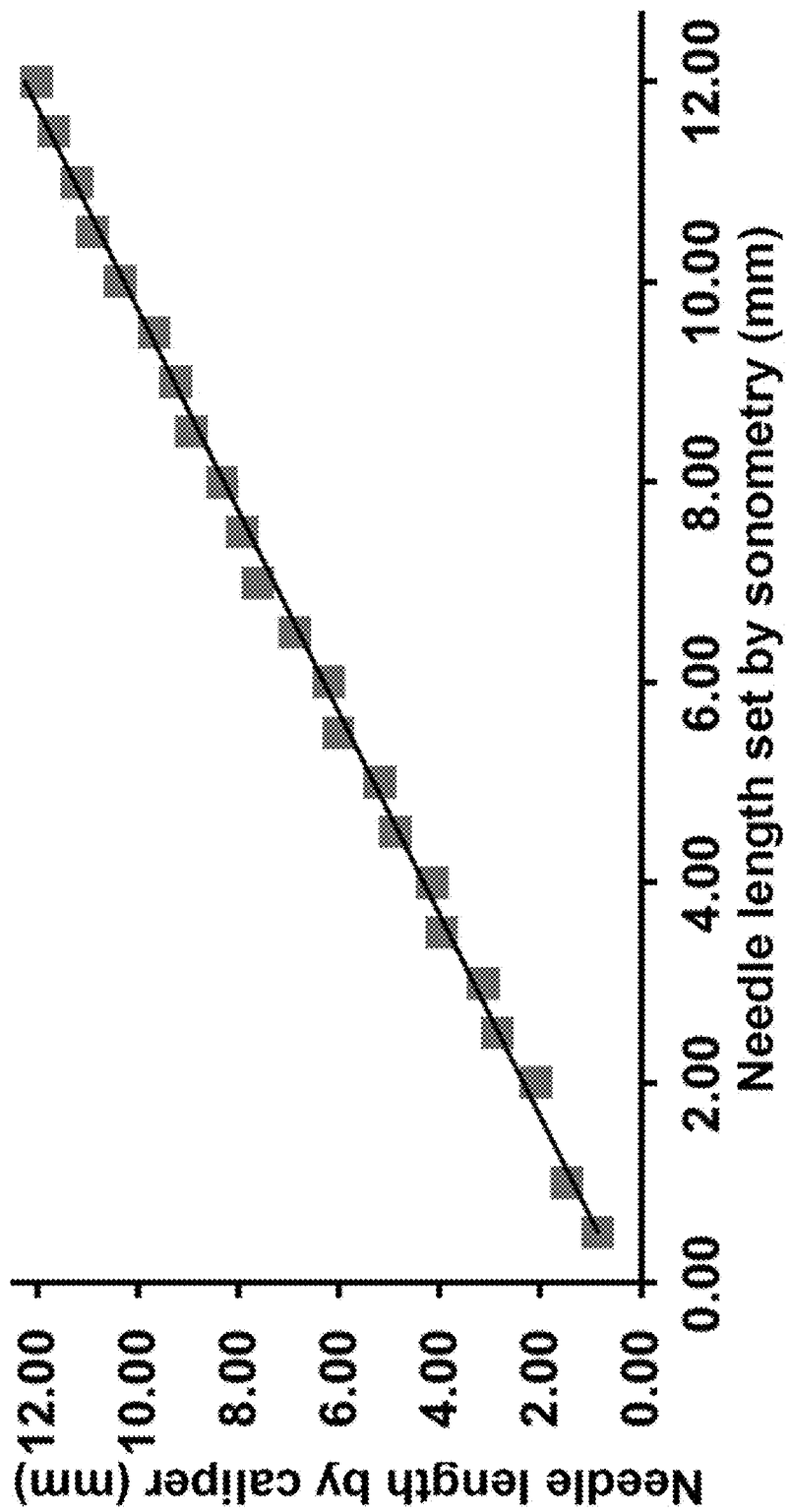
FIG. 10 is a graphical representation of a needle length measured by a caliper and in a water bath by sonometry during an initial pilot study.

In a water tank, the needle exposure length was set by sonometry between the microcrystal and crystal to incremental length extents within a range from 0.5 to 12.0 mm, relevant to transendocardial injections. The "true" needle exposure length was measured directly by a caliper at each testing increment. As can be seen in FIG. 10, each length measurement set by sonometry and then checked by using a caliper as the reference had excellent precision (very high correlation of $R^2=0.998$) and accuracy (very low mean difference of −0.31 mm and standard deviation of 0.15 mm).

Example 2

Needle Sonometry in a Heart Specimen

Figure 11B:
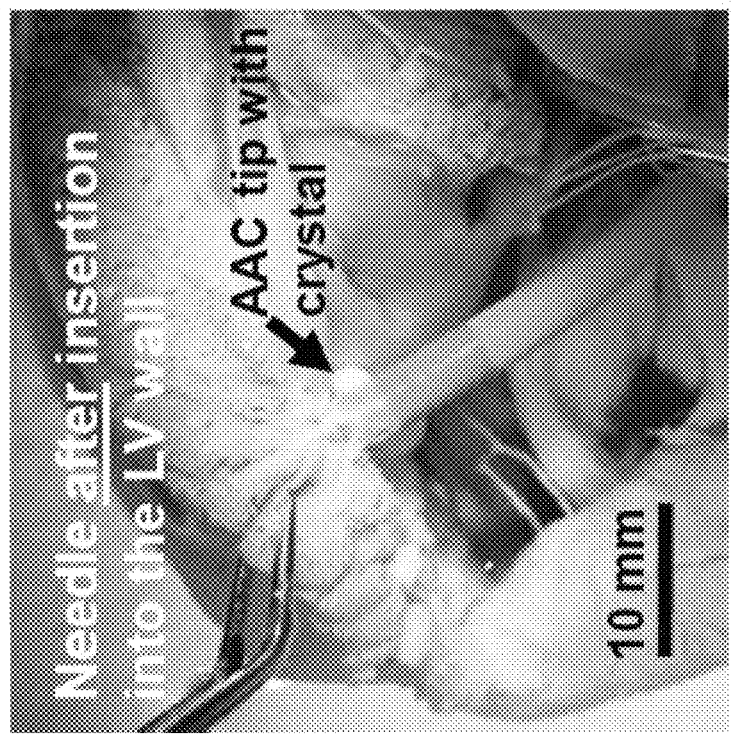
FIG. 11B is an example of a needle and crystal during insertion into a pig heart.
Figure 11A:
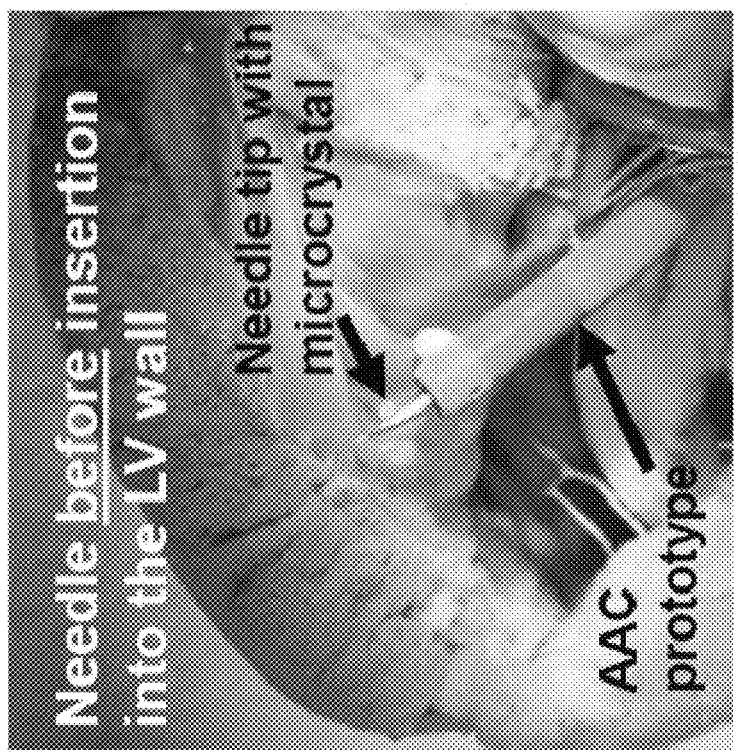
FIG. 11A is an example of a needle and crystal before insertion into a pig heart.
Figure 11C:
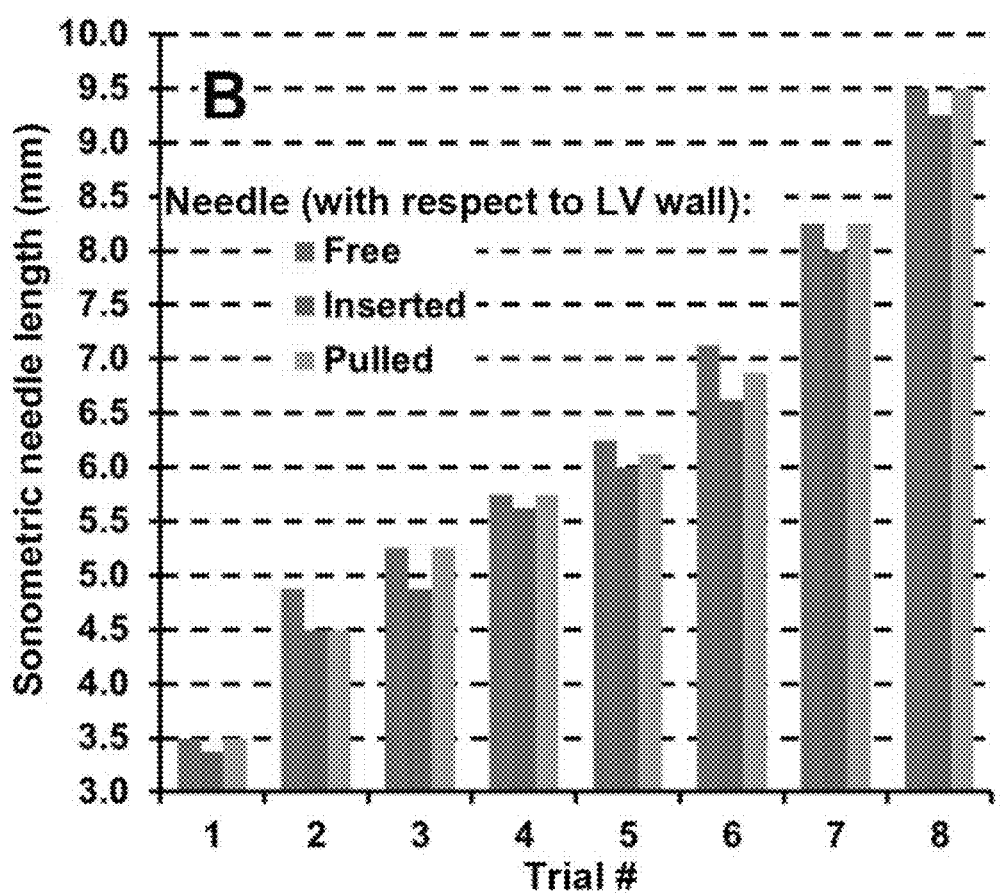
FIG. 11C is a graphical representation of a needle length before ("free"), during, and after ("pulled") insertion into a left ventricular wall of an excised pig heart during multiple pilot trials. Measurement differences in each trial document the ability to detect the effect of inserting and extracting the needle on its actual exposure length.

A freshly excised and dissected pig heart specimen was placed in a water tank. A tip of an AAC prototype, incorporating the needle with the microcrystal attached at its distal end, was advanced into the LV cavity through the mitral valve, as shown in FIG. 11A. As shown in FIG. 11B, the catheter was further advanced so that its tip became in a direct contact with the inner surface of the LV wall. Using the catheter handle and slider, the needle at the tip of the catheter was inserted into the LV wall at various pre-set insertion lengths. FIGS. 11A a11d 11B show the needle and microcrystal before insertion and the catheter tip with the crystal during insertion, respectively. As can be seen in FIG. 11C, sonometry allows for acoustic navigation of the crystal and needle before insertion, during needle insertion into the myocardium, and after pulling the catheter and freeing the needle. A decrease in sonometrically measured needle length when inserted into the LV wall is consistent with a slight push-back of the needle during muscle penetration. In most of the presented trials, the original needle exposure length was nearly or completely recovered after pulling the needle out of the LV wall. The changes in actual needle exposure length before, during, and after insertion emphasize the need for the accurate instantaneous measurement of that length, as provided by the current invention.

Example 3

Tests in A Water Tank with Simulated Human Chest Attenuation

Figure 12A:
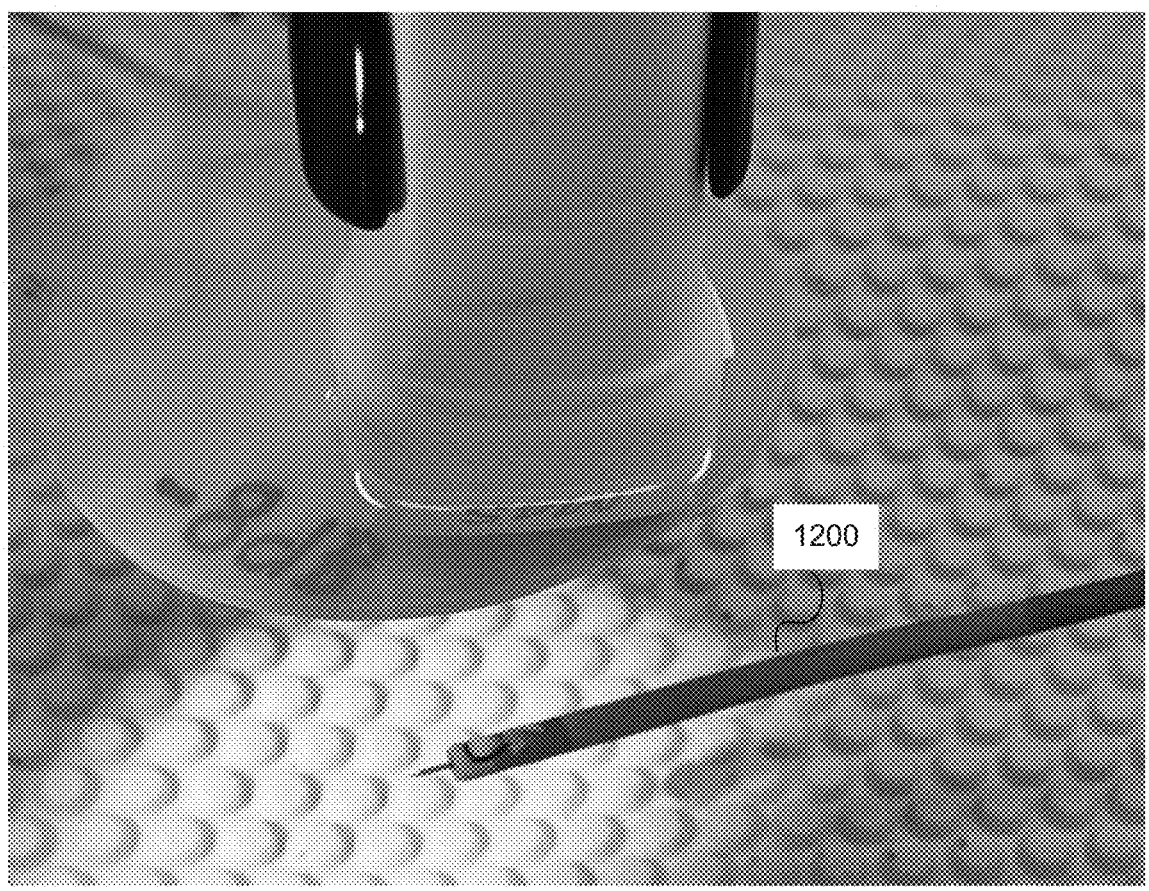
FIG. 12A shows an experimental setting in vitro in a water bath with an US transducer, attenuative polyurethane pad (to simulate chest attenuation), and the AAC prototype with an exposed needle for catheter tip identification by a PW Doppler ultrasound scan.

FIG. 12A shows an example of a needle and crystal for catheter tip identification in a water tank by a PW Doppler ultrasound system. The catheter 1200 may include the steerable catheter sheath that is customized by attaching a miniature piezoelectric crystal to its tip. The crystal may be driven by an external waveform generator. By interacting with a signal transmitted by an ultrasound transducer, the vibrating crystal produces a distinctive pattern in a PW Doppler spectral plot or forms a large color marker in a color Doppler scan. Both the artificially generated spectral pattern and color marker allow unambiguous identification of the catheter tip.

The experimental setting included a Vivid 7 scanner (GE Vingmed Ultrasound AS, Horton, Norway) equipped with M4S and 3V transducers set to a 2-MHz transmit frequency. A polyurethane pad, inducing approximately an 8-dB ultrasound signal loss at 1 MHz, was interposed under water between the catheter sheath and the probe to simulate ultrasound signal attenuation by a human chest. In FIG. 12A, the system includes the M4S transducer, the attenuative polyurethane pad, and the catheter sheath (including an injection insert) in a water bath with an ultrasound absorption lining at the bottom.

Figure 12B:
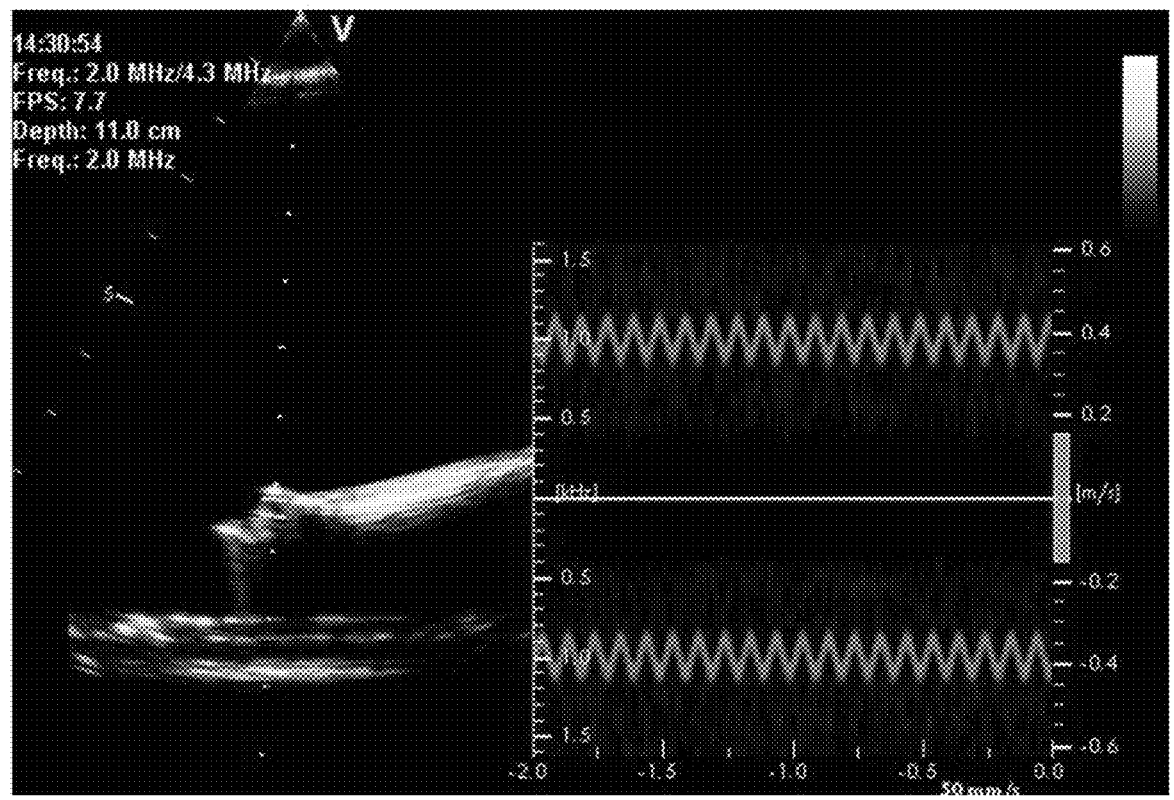
FIG. 12B shows, on the left, an ultrasound image of the AAC tip with an overlapping PW Doppler sample window. On the right, there is an example of Doppler shift signals that signify detection of the AAC tip.

FIG. 12B shows, on the left, an ultrasound image of the AAC distal end with an exposed needle at its tip and a PW Doppler sample window overlapping the catheter tip. On the right, there is an example of Doppler shift signals that signify detection of the AAC tip. Compared to FIG. 4B, the detected Doppler shift signals are of sinusoidal shape, which was achieved by modulating the signal that drives the crystal at the catheter sheath tip. In FIG. 12B, the crystal at the catheter sheath tip was driven by a sinusoidal signal with a 1-kHz frequency and 3-V peak-to-peak amplitude. Considering a 1,540-m/s ultrasound propagation speed, the crystal vibrations induced a Doppler shift of +0.38 m/s. Because the 1-kHz sinusoidal signal was frequency-modulated (the signal frequency was changing by +100 Hz with a rate of 10 Hz), it appeared on the ultrasound spectral plot as a horizontal wave with a 10-Hz frequency centered at approximately +0.4 m/s and −0.4 m/s levels. Modulation was employed to assure that the wave will be clearly distinguishable from any patterns of blood flow velocity spectra in a beating heart. The placement of the PW Doppler window completely over, partially over, or away from the catheter tip results in a strong identification signal, weak identification signal, or its disappearance, respectively. In this way, the appearance of the identification signal facilitates detection and navigation of the catheter tip. The identification signal can also be heard, and the audible strength of the identification signal contributes to the convenience and accuracy of its navigation function.

Figure 13A:
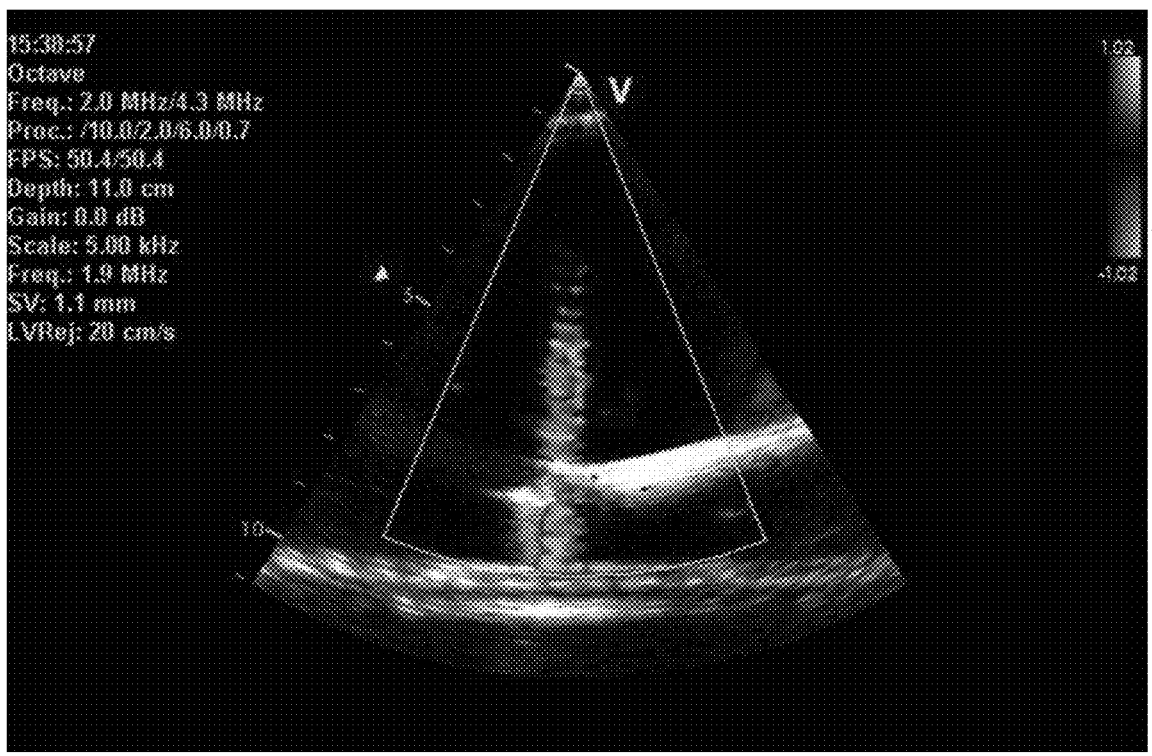
FIG. 13A shows a first example of a catheter tip identification in a water tank by a color Doppler ultrasound scan. Compared to FIG. 12B, a waveform of a different shape and frequency was used to drive the crystal and the AAC tip to achieve the color pattern (color marker) of the catheter tip.
Figure 13B:
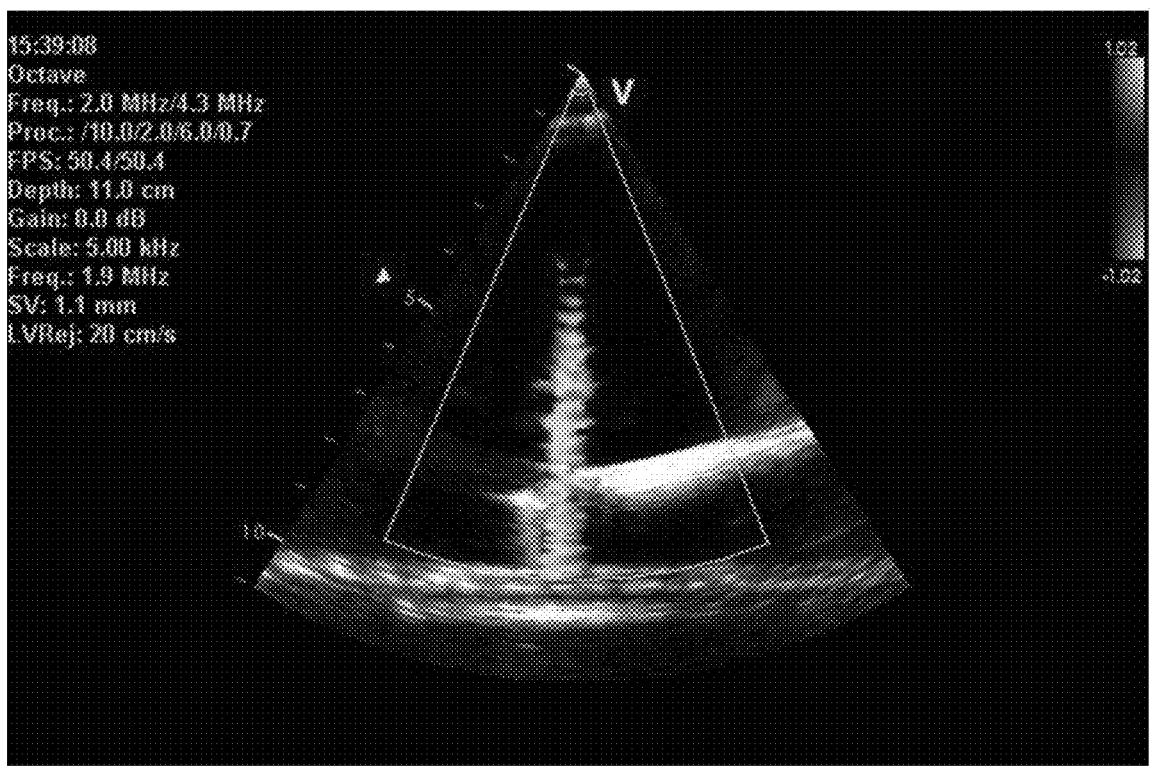
FIG. 13B shows a second example of a catheter tip identification in a water tank by a color marker using a color Doppler ultrasound scan.

FIG. 13A shows a first example of tip identification in a water tank by a color Doppler marker produced by the Doppler ultrasound system. In this example, the crystal was driven by a square-wave signal, which is typically rich with high frequency harmonics. An interference of these harmonics with the color Doppler scan plane induced a large, clearly visible color marker spreading along the scan lines interrogating the catheter tip (i.e., the vibrating crystal). While the amplitude of the driving signal, which was set to 400-mV peak-to-peak in this example, controls the thickness of the marker, the frequency controls a color of the marker. In FIG. 13A, the blue color marker is induced by a 103-kHz square-wave signal. In FIG. 13B, the orange color marker is induced by a 102-kHz square-wave signal.

Unlike in PW Doppler images shown in FIG. 12B, where the PW Doppler sample window had to be interactively moved to identify the catheter tip, the color Doppler marker occurred as long as the tip was located within the imaging plane and tracked its motion in the real time. The color appearance of the Doppler marker depends, however, not only on the frequency of the driving signal, but is also affected by the selected Doppler velocity scale and position of the catheter tip within the image field.

Figure 13C:
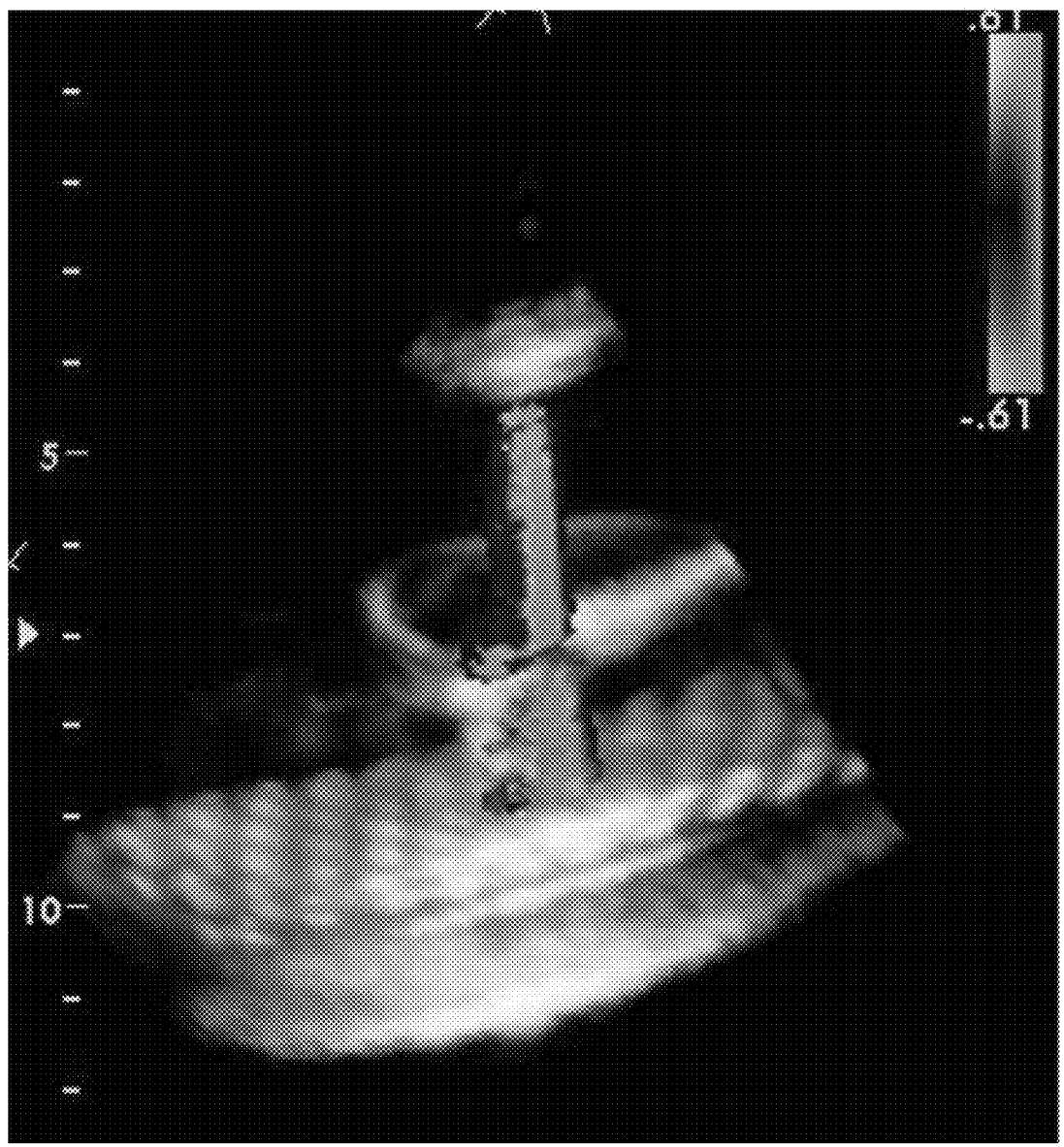
FIG. 13C shows an example 3D depiction of the catheter tip identified bythe color marker.

FIG. 13C shows an example 3D depiction of the catheter with the color Doppler marker. In FIG. 13C, the 3D depiction of the catheter with the color marker demonstrates the concept of real-time spatial identification and guidance of the catheter tip by 3D Doppler ultrasound. Note the depiction of the attenuative polyurethane pad at the top, the spatial appearance of the color marker in the middle, and the rendition of the ultrasound absorptive lining at the bottom of the image.

Example 4

Studies with A Pig Heart Specimen

Figure 14A:
FIG. 14A shows an experimental in vitro setting that includes a formalin-fixed and dissected pig heart.

FIG. 14A shows the experimental setting, which included a formalin-fixed pig heart that was cut-open along the left ventricular lateral wall from the apex to base and positioned into a water bath on top of an ultrasound absorptive lining. An attenuative pad was interposed between the heart and the ultrasound transducer. The catheter was inserted into the left ventricle via the aortic root and valve, and its distal end is directly visible through the opening in the LV lateral wall.

Figure 14B:
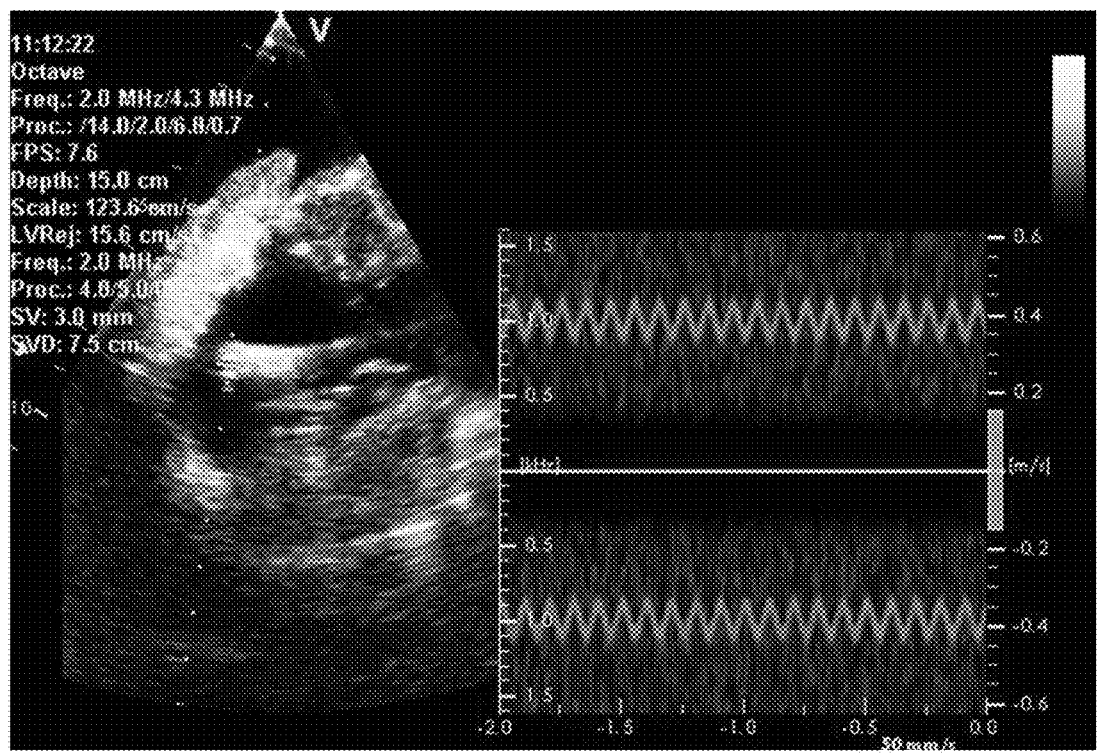
FIG. 14B shows that crystal at the AAC tip was identified by a PW Doppler window.
Figure 14C:
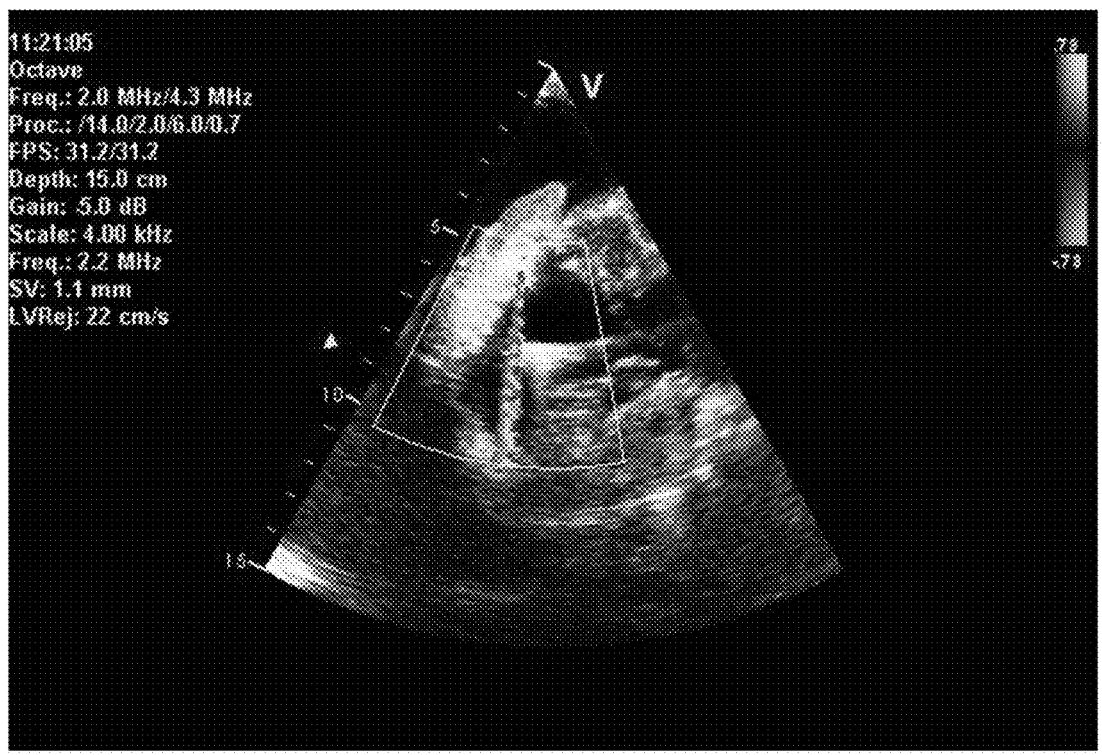
FIG. 14C shows that the crystal was identified by a color Doppler marker.
Figure 14D:
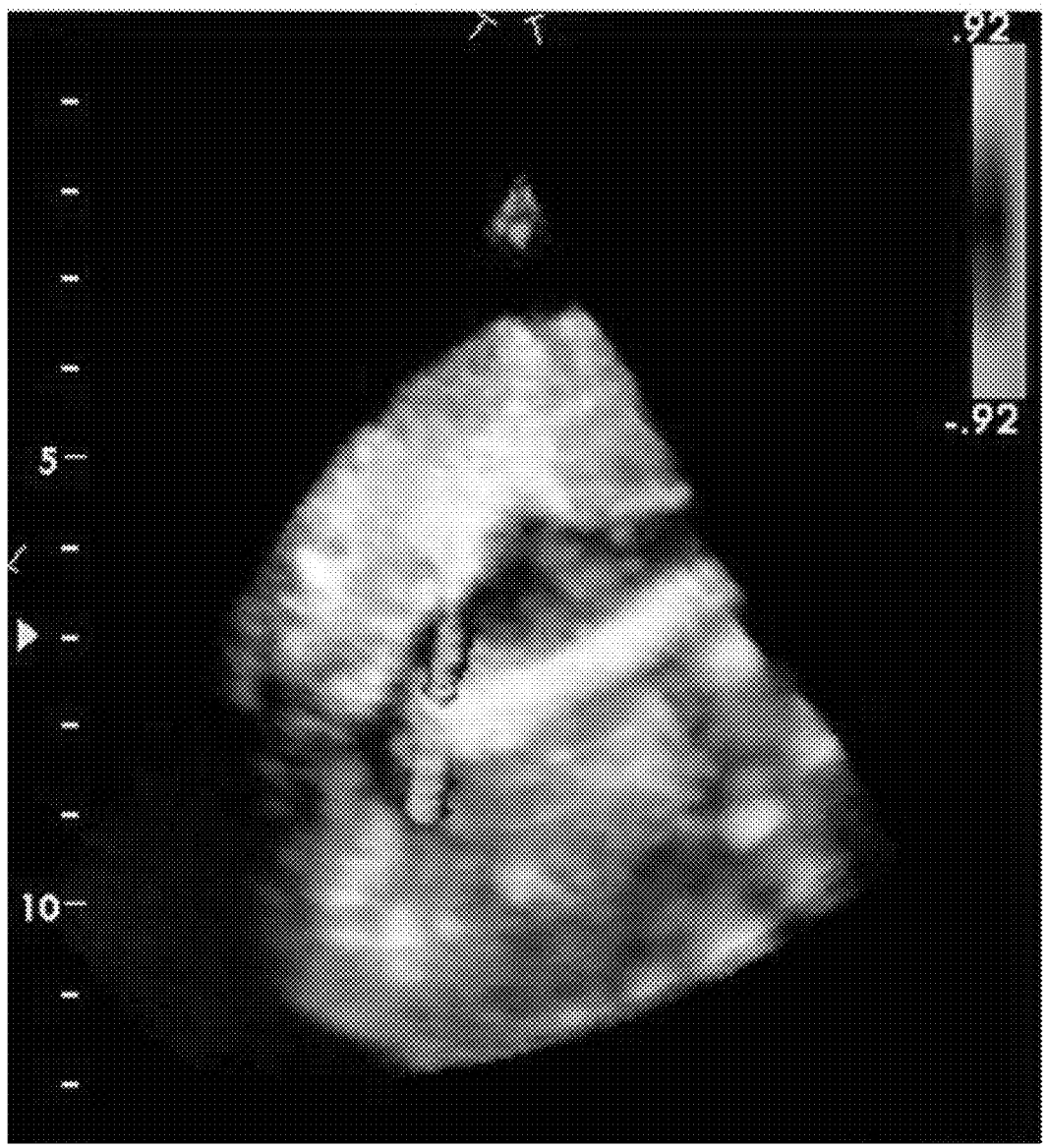
FIG. 14D shows that the crystal was identified by a color Doppler marker in a real-time 3D projection.

FIG. 14B shows the AAC tip being overlappedby a PW Doppler sample window on the right and the corresponding identification Doppler shift signals on the right. FIG. 14C shows the same anatomic scenario, but the AAC tip was identified by a color Doppler marker. FIG. 14D shows that the crystal was identified by a color Doppler marker in a real-time 3D projection.

Figure 15A:
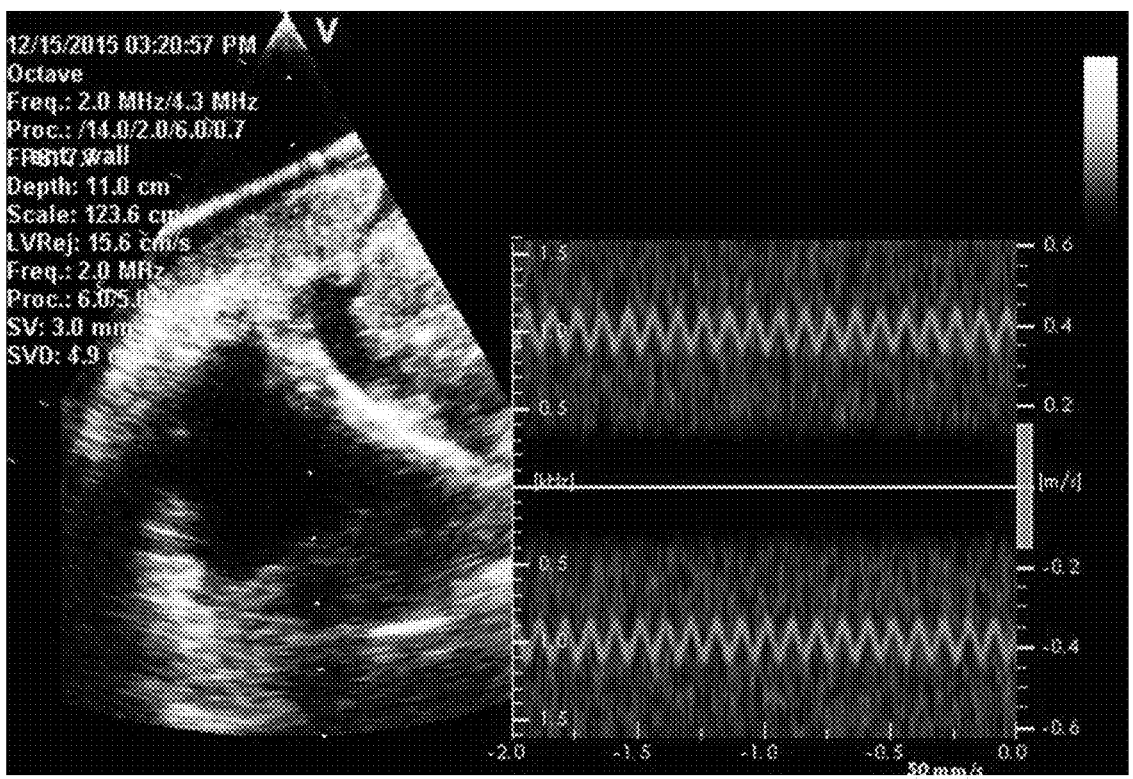
FIG. 15A shows identification of the catheter tip steered towards the left ventricular anterior wall by the PW Doppler sample window.
Figure 15B:
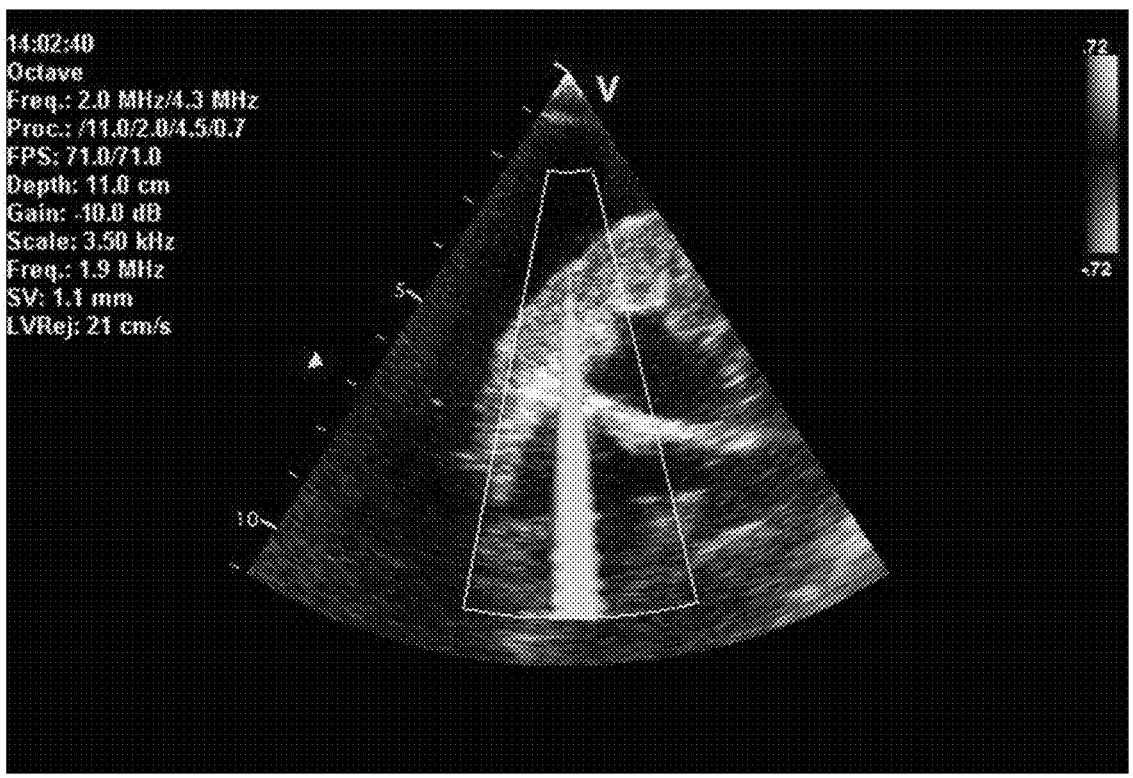
FIG. 15B shows identification of the catheter tip steered towards the left ventricular anterior wall by the color Doppler marker.
Figure 15C:
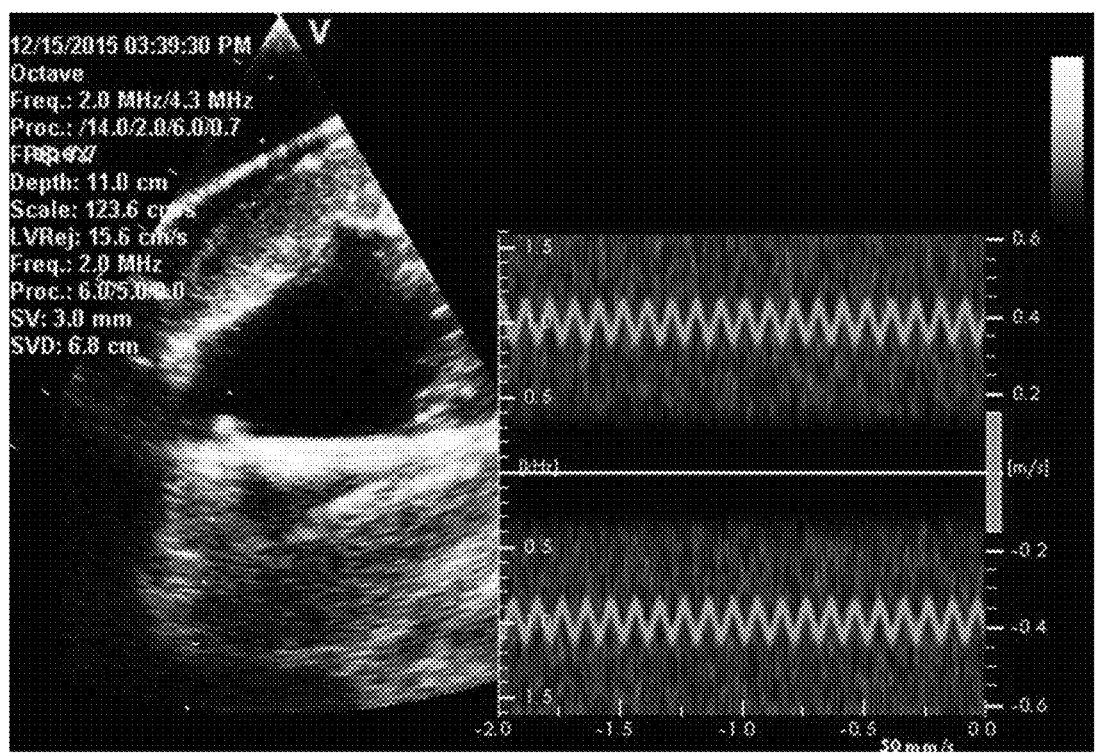
FIG. 15C shows identificatioin of the catheter tip steered towards the left ventricular posterolateral wall by the PW Doppler sample window.
Figure 15D:
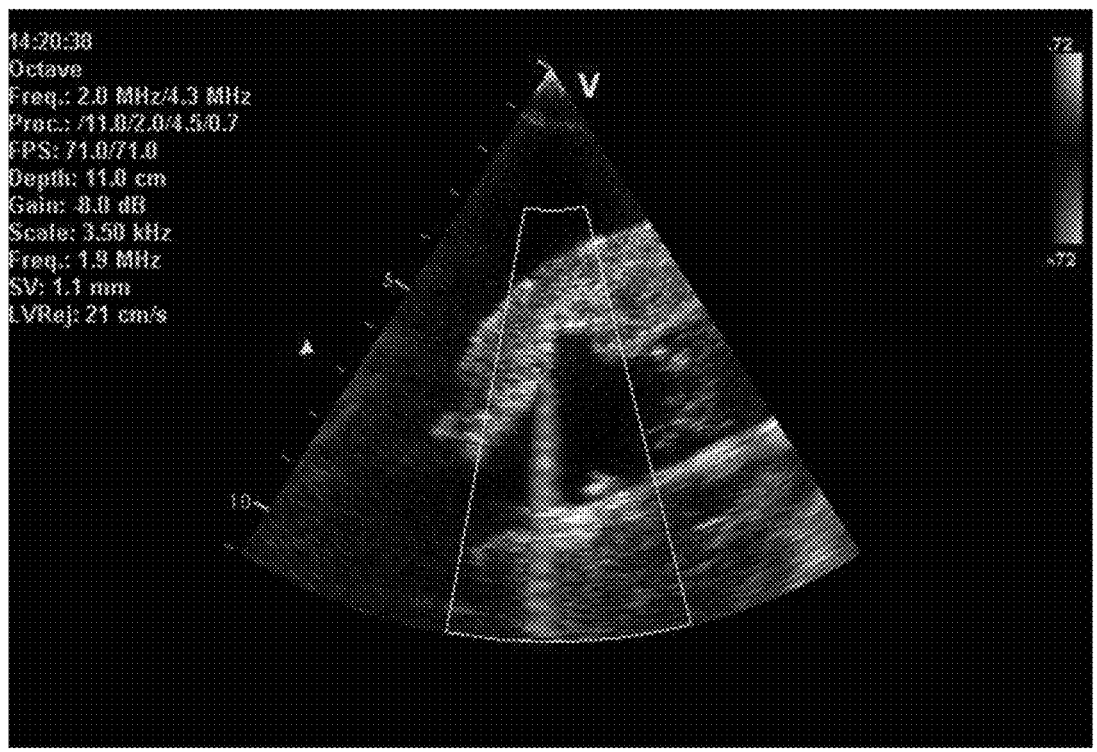
FIG. 15D shows identification of the catheter tip steered towards the left ventricular posterolateral wall by the color Doppler marker.

FIG. 15A shows that the AAC tip after it was repeatedly steered towards the LV anterior wall and identified by the PW Doppler sample window. FIG. 15B shows and the same anatomic situation, but the AAC tip was identified by the color Doppler marker. FIG. 15C shows the catheter tip after it was repeatedly steered towards the LV posterolateral wall and identified by the PW Doppler sample window. FIG. 15D shows the same anatomic situation, but the AAC tip was identified by the color Doppler marker.

Notice that in B-mode, ie, without Doppler identification, the catheter tip may visually merge with anatomy and a blurry ultrasound depiction of the crystal may be easily confused with a small intraventricular anatomical structure. The studies demonstrate catheter tip identification within replicated cardiac anatomy and simulated intracardiac blood flow, respectively.

Example 5

Studies with A Beating Mechanical Heart

Figure 16A:
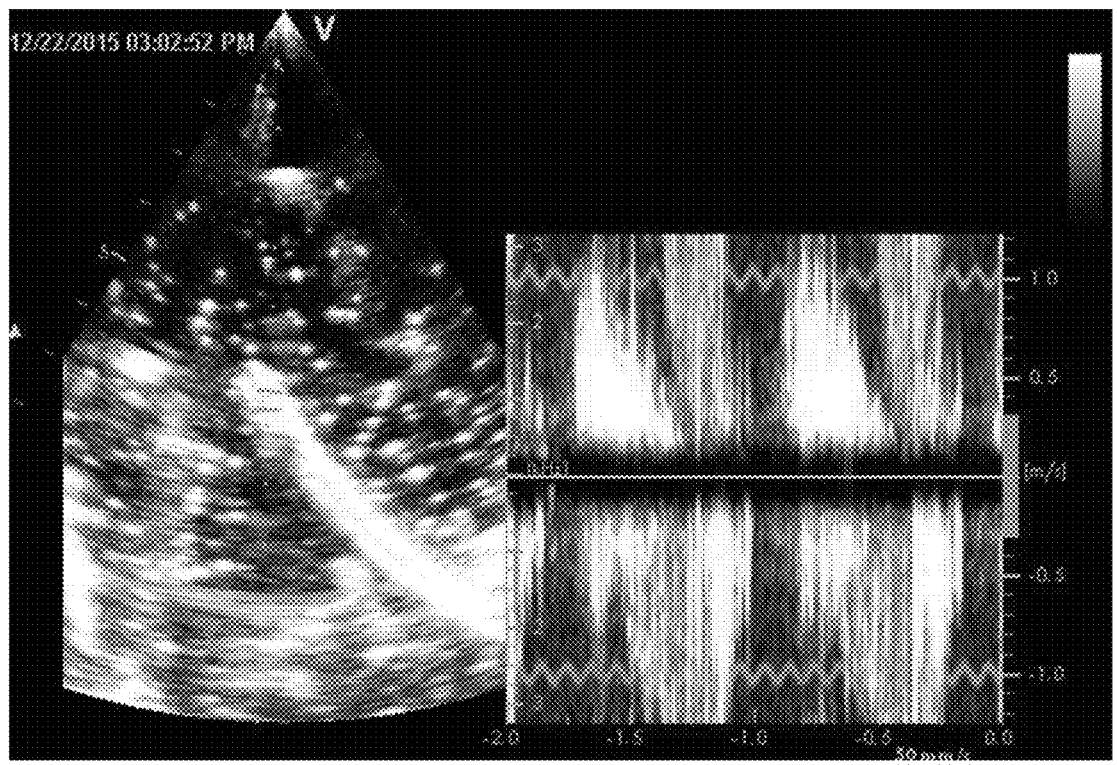
FIG. 16A shows an example experiment that identifies a catheter tip in a beating mechanical LV model by a PW Doppler window.

FIG. 16A shows the experimental setting, which includes a Pulse Duplicator (ViVitro Labs, Inc., Victoria, Canada), which replicates cardiac mechanical function by a beating LV made of an elastic hemi ellipsoid membrane, functional porcine valves in mitral and aortic positions, and an adjustable heart rate and stroke volume. The model features thin acrylic windows allowing ultrasound scans in various projections and allows catheter placement via the mitral valve into the ventricular chamber. The LV rate was set to 70 beats per minute with a stroke volume of 60 ml in this example.

FIG. 16A shows an example experiment that identifies a catheter tip in a mechanical heart by a PW Doppler sample window. Despite enhancement of a Doppler flow signal by injecting air bubbles and massive mitral regurgitation notwithstanding, the PW Doppler window clearly identified the catheter tip by corresponding Doppler shift signals (sinusoidal waves) positioned at +1 m/s and −1 m/s in the spectral plot. This specific position of the waves was achieved by driving the crystal at the catheter tip with a modulated sinusoidal signal with a frequency of 2.6 kHz.

Figure 16B:
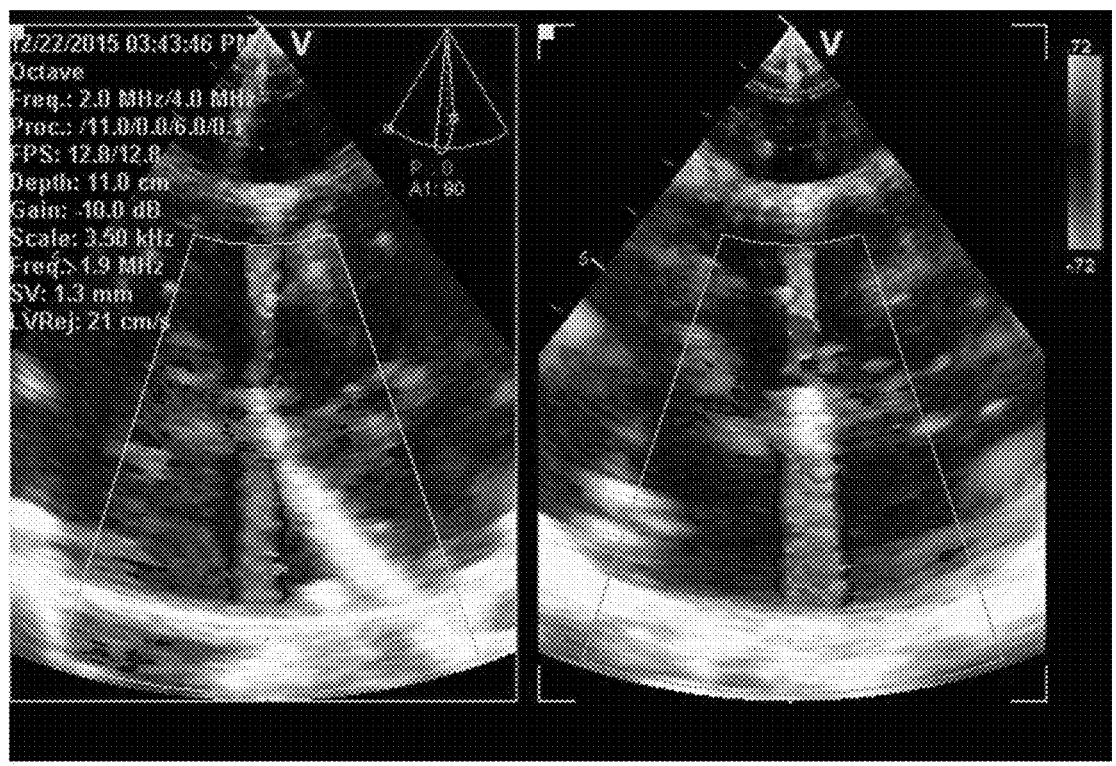
FIG. 16B shows an example color Doppler image with color markers identifying the catheter tip inside the beating mechanical LV model using imaging projections oriented along (left) and across (right) the catheter. A 4D US transducer and simultaneous real-time biplane imaging was used in this example.
Figure 16C:
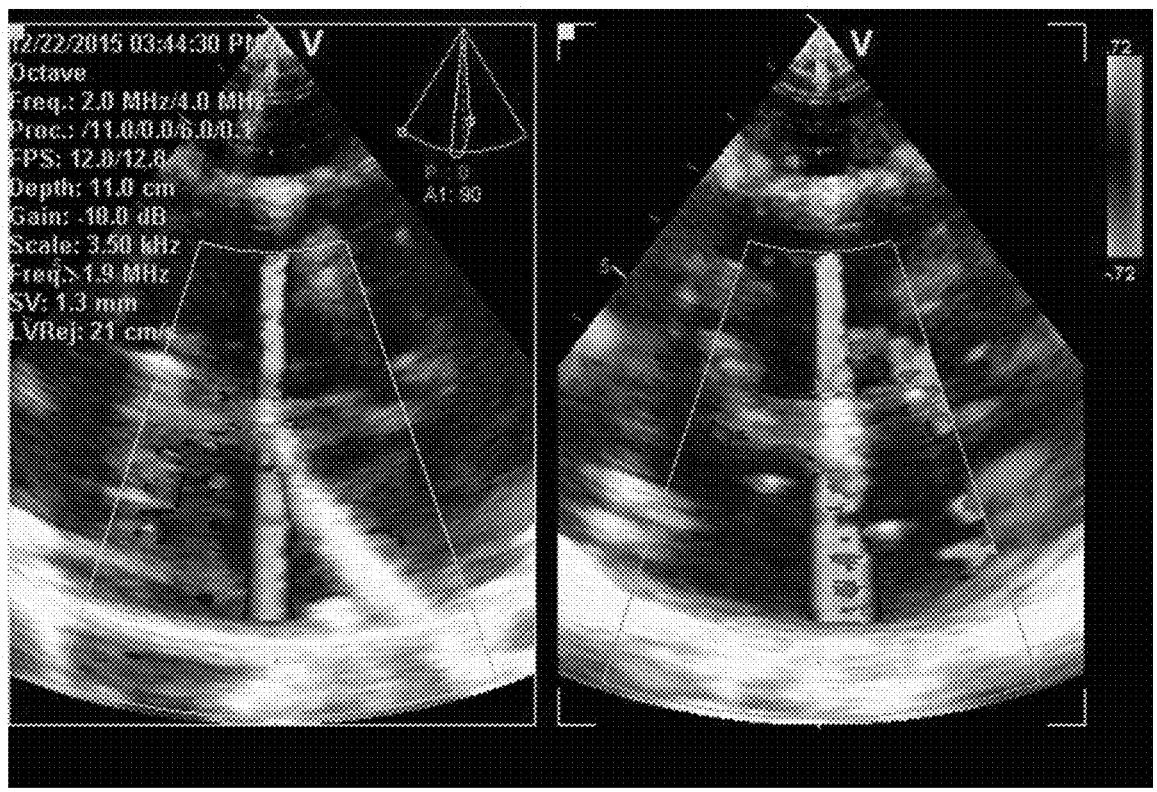
FIG. 16C shows a second example biplane color Doppler image, which is identical to FIG. 16B except that the color marker changed from blue to orange by adjusting the frequency of the driving signal.

FIG. 16B shows an example color Doppler image identifying the catheter tip inside the beating mechanical ventricle by two perpendicular scan planes, simultaneously generated by a 4D imaging transducer. The plane on the left is oriented along the catheter tip, whereas the plane of the right is oriented across the catheter tip. FIG. 16C shows a second example color Doppler image identifying the catheter tip inside the beating mechanical ventricle. The difference from FIG. 16B is only in a small change in frequency of the signal driving the crystal, which resulted in an orange (rather than blue) color Doppler marker of the AAC tip in the biplane projection.

Interactive positioning of the PW Doppler window identifies the crystal affixed at the tip of the catheter by the characteristic wave occurring in the Doppler spectral plot. In this way, the catheter tip will be identified within ultrasound depiction of cardiovascular anatomy. The color Doppler marker may identify the crystal at the catheter tip and tracks motion of the tip. Color of the marker may change by alternating between two different frequencies of the signal that drives the crystal. Selection of a distinctive color or flashing between two different colors of the marker is intended for optimal identification of the Doppler marker within the intraventricular flow of a beating heart. By properly adjusting amplitude and frequency of the signal driving the crystal and color Doppler gain, patterns of ventricular filling flow were subdued and the catheter tip was clearly identified by the color Doppler marker.

Example 6

Detection of the Tip of the Acoustically Active Catheter in a Beating Pig Heart

Figure 17A:
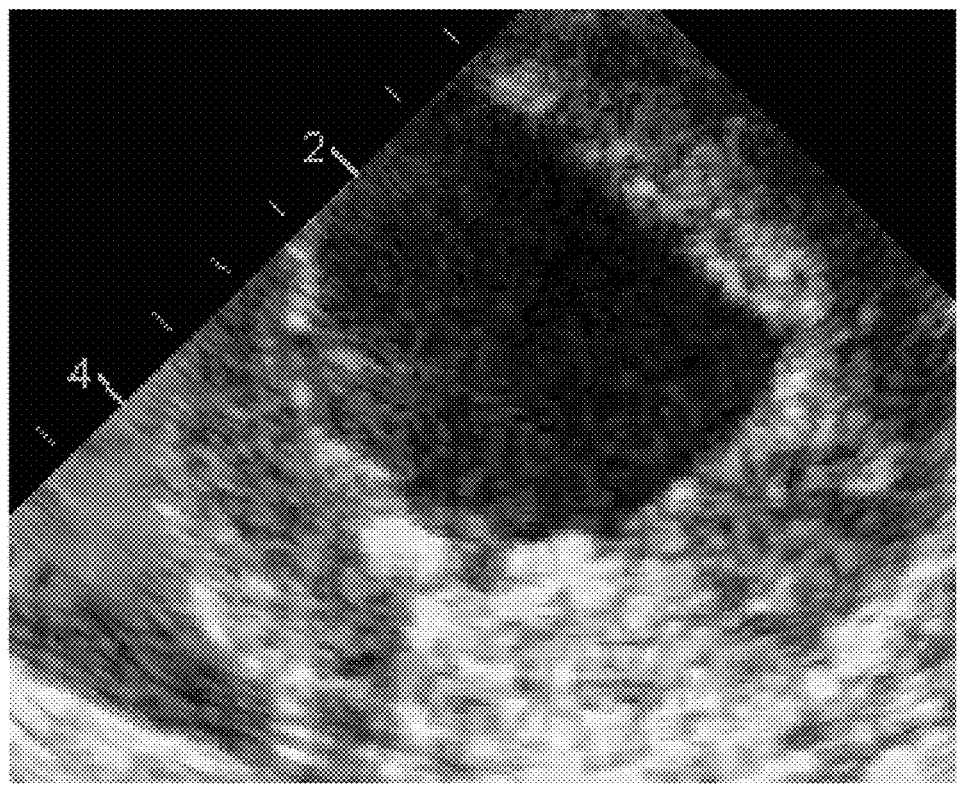
FIG. 17A shows an example image in a short-axis cardiac scan in B-mode including a catheter tip.
Figure 17B:
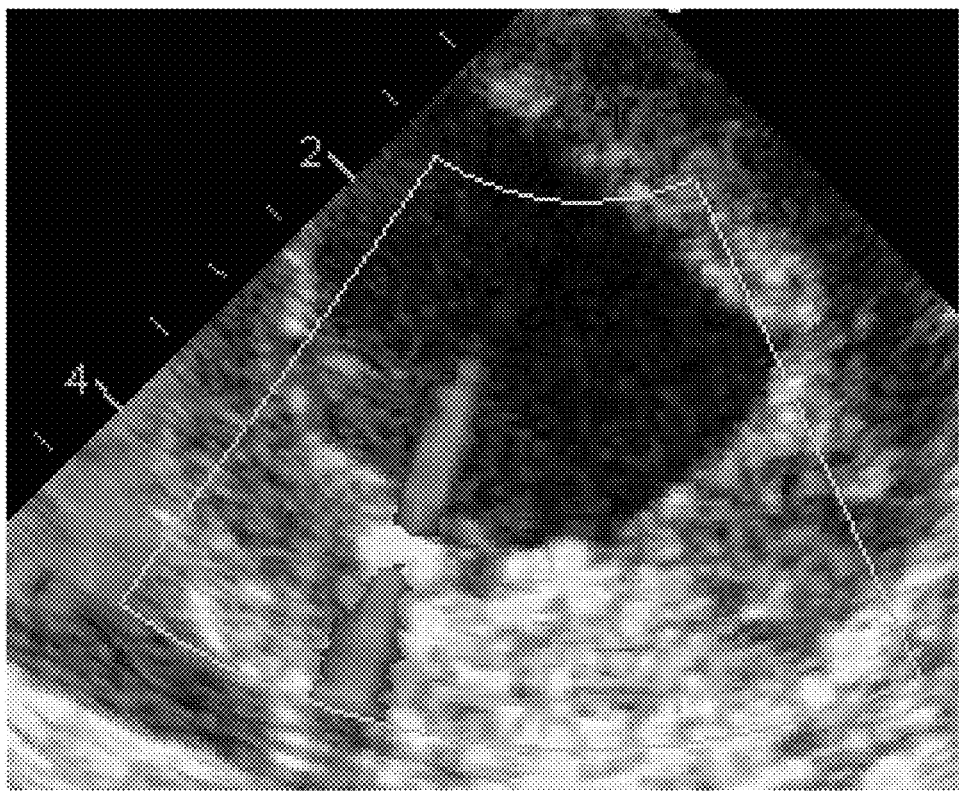
FIG. 17B shows an example color Doppler image of the same projection as in FIG. 17A, but identifying the location of the catheter tip by a color marker.

The AAC has an acoustically active tip that allows unambiguous detection and accurate guidance of the catheter tip by conventional color Doppler echocardiography. The presented example is from tests in pigs. FIG. 17A shows an example image in a short-axis cardiac scan in B-mode including a catheter tip, which is, however, visually indistinguishable. FIG. 17B shows an example a color Doppler marker indicating the location of a catheter tip.

Example 7

Examples of Acoustically Active Catheter

The example shows an example design of the AAC that provides color Doppler markers of the catheter tip (blue marker) and the needle tip (red marker). Both markers are independent and track motion of the catheter or retraction/exposure of the needle in real time. FIG. 18 shows an example color Doppler image indicating the location of a needle and a catheter tip.

Example 8

Acoustically Active Cannula

Figure 19A:
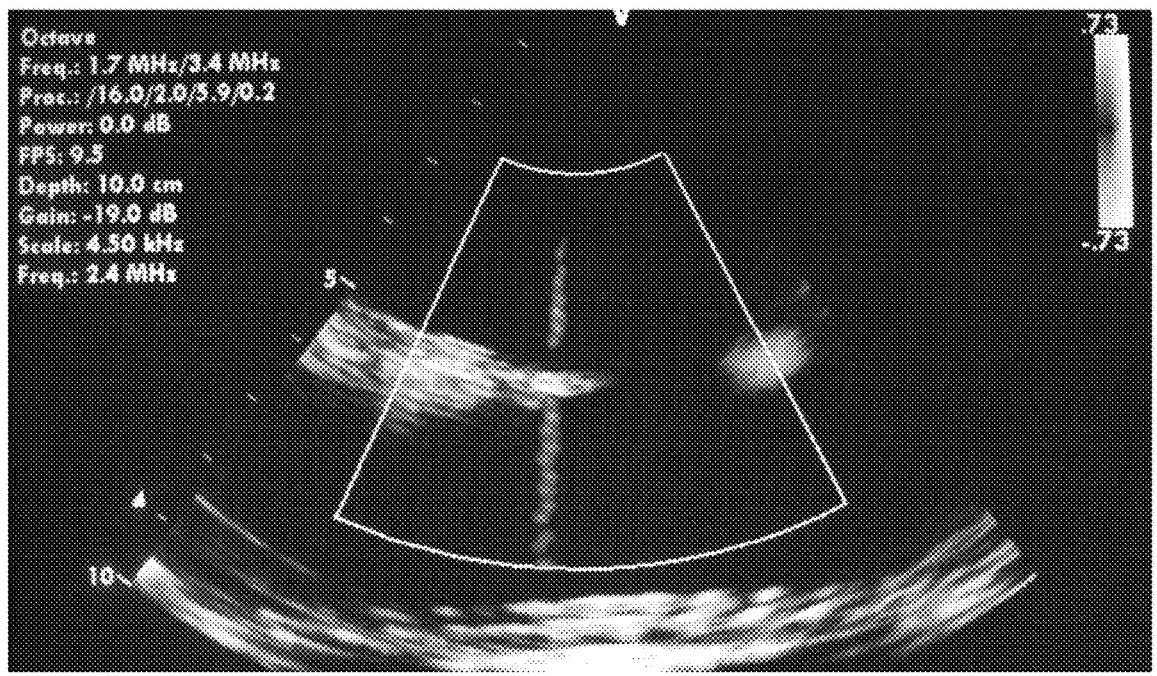
FIG. 19A shows a first example color Doppler image indicating by a color marker the location of a tip of an acoustically active cannula in a projection along the cannula.
Figure 19B:
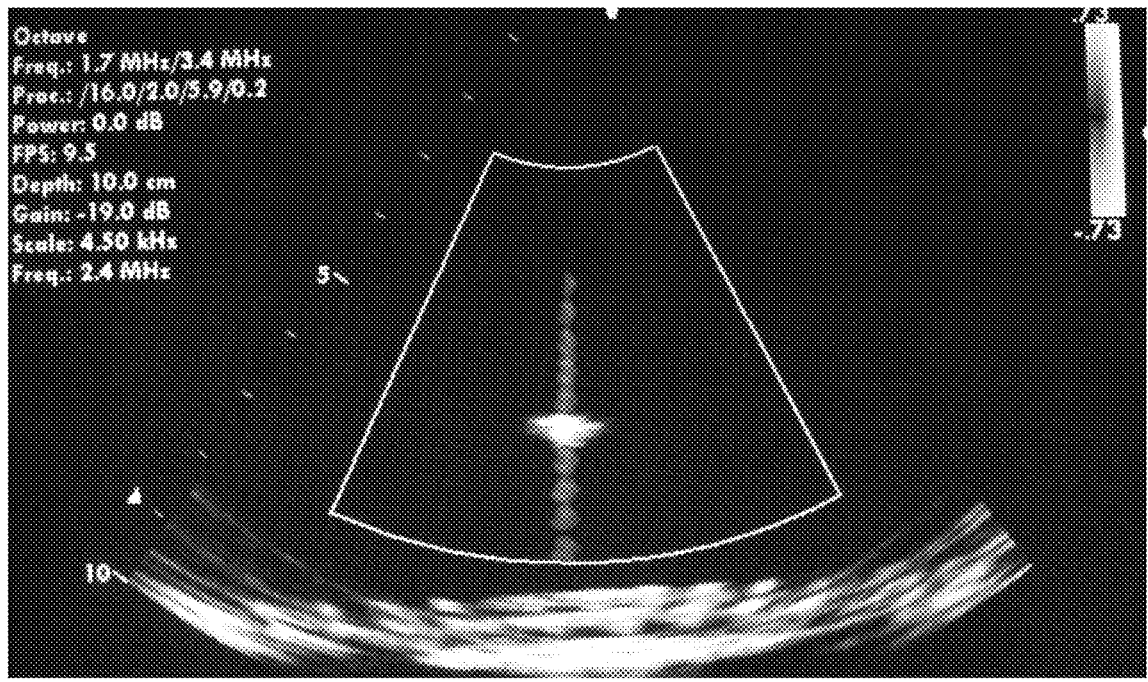
FIG. 19B shows a second example color Doppler image indicating by a color marker the location of a tip of an acoustically active cannula in a projection across the cannula.

This cannula (16 G=1.3 mm outer diameter) is fitted with a microcrystal (~0.7 mm in diameter) and is intended for navigation of its tip into the lumen of a vein or an artery when access to such vessels is otherwise done blindly or under difficult circumstances (emergency, collapsed vessels, etc). The navigation principle may work with a biopsy cannula and many other similar minimally invasive instruments and applications. FIG. 19A shows a first example color Doppler image indicating the location of an acoustically active cannula, when the US scan is oriented along the cannula. FIG. 19B shows a second example color Doppler image indicating the location of an acoustically active cannula, when the US scan is oriented across the cannula.

The present invention has been described in terms of one or more preferred embodiments, and it should be appreciated that many equivalents, alternatives, variations, and modifications, aside from those expressly stated, are possible and within the scope of the invention.

The invention claimed is:

1. A system, comprising:
an injection catheter, the injection catheter comprising:
    an outer tube comprising a first lumen;
    an inner tube disposed within the first lumen of the outer tube, the inner tube comprising a second lumen;
    a needle slidably disposed within the second lumen of the inner tube;
    a first acoustic marker coupled to the injection catheter at a location proximate to a distal end of the injection catheter and configured to generate a first acoustic signal;
    a second acoustic marker coupled to the needle at a location proximate to the distal end of the needle and configured to generate a second acoustic signal; and
a sonometry system configured to measure an exposure length of the needle based on acoustic communication between the first and second acoustic markers by alternating between transmission of one of the first and second acoustic markers and reception of the other one of the first and second acoustic markers in order to determine a measurement of distance between the first and second acoustic markers as the exposure length of the needle.

2. The system of claim 1, wherein the first and second acoustic markers include piezoelectric crystals.

3. The system of claim 2, wherein the piezoelectric crystals are made of lead zirconate titanate or polyvinylidene fluoride.

4. The system of claim 1, further comprising a first electrical wiring in electrical communication with the first acoustic marker.

5. The system of claim 1, further comprising a second electrical wiring in electrical communication with the second acoustic marker.

6. The system of claim 1, further comprising:
a waveform generator electrically connected to at least one of the first acoustic marker or the second acoustic marker and wherein the at least one of the first acoustic marker or the second acoustic marker is configured to generate an acoustic signal in response to electrical input received from the waveform generator.

7. The system of claim 1 further comprising an ultrasound system electrically connected to at least one of the first acoustic marker or the second acoustic marker and wherein said acoustic marker is configured to generate an acoustic signal in response to electrical input received from the ultrasound system.

8. A method, comprising:
providing a catheter comprising a catheter tip equipped with a needle and a first crystalline element adapted to actively generate a first acoustic wave at a first frequency;
generating, by an ultrasound imaging system including an ultrasound transducer, an image of the catheter tip arranged within a body based on an ultrasound echo produced by ultrasound waves generated by the ultrasound transducer and reflected by the catheter tip;
detecting, by the ultrasound imaging system, an acoustic interference signal formed by the first acoustic wave generated by the first crystalline element and a second acoustic wave generated by the transducer;
generating a third acoustic wave having a second frequency using a second crystalline element located at a needle tip of the needle;
providing acoustic communication between the first and second crystalline elements to determine a needle exposure length by alternating between transmission of one of the first and second crystalline elements and reception of the other one of the first and second crystalline elements in order to determine a measurement of distance between the first and second crystalline elements as the needle exposure length, and
displaying, by the ultrasound imaging system, the needle exposure length and a position of the catheter tip in response to the detected acoustic interference signal.

9. The method according to claim 8, wherein determining a desired change of a position of the catheter tip includes changing a position of the catheter tip so as to increase an intensity of said acoustic interference signal.

10. The method according to claim 8, wherein detecting the acoustic interference signal includes detecting an acoustic interference signal having intensity that depends on a separation distance between the catheter tip and a Doppler scan plane associated with the transducer.

11. The method according to claim 8, wherein determining a desired change of a position of the catheter tip includes changing a position of the catheter tip in reference to a target within a cardiovascular system and an output, which is generated by the ultrasound imaging system in response to the detected acoustic interference signal and which represents a distance between the target and the catheter tip.

12. The method according to claim 8, wherein detecting the acoustic interference signal includes generating an output, from the ultrasonic imaging system, that represents an intensity of the identified acoustic interference signal.

13. The method according to claim 8, wherein generating the image further comprises:
spatially overlapping a pulsed-wave Doppler window, produced by the transducer, with an anatomic target within the body; and
generating an output, from the ultrasonic imaging system, that represents an intensity of the acoustic interference signal.

14. The method according to claim 13, wherein determining a desired change of a position of the catheter tip includes navigating the catheter tip towards said anatomic target by determining a location associated with maximum intensity of the acoustic interference signal.

15. The method according to claim 13, further comprising:
directing the crystalline element into a first scan plane and then further directing the crystal along that first scan plane towards a second scan plane; and thereby
navigating the crystalline element and the catheter tip of the AAC along an axis defined by the first and second scan planes.

16. A method, comprising:
producing a first signal having a first frequency using a first acoustic marker located at a catheter tip of an injection catheter, the injection catheter comprising a needle;
producing a second signal having a second frequency using a second acoustic marker located at a needle tip of the needle;
providing acoustic communication between the first and second acoustic markers to measure an exposure length of the needle by alternating between transmission of one of the first and second acoustic markers and reception of the other one of the first and second acoustic markers in order to determine a measurement of distance between the first and second acoustic markers as the exposure length of the needle; and
receiving by an ultrasound transducer third and fourth signals having third and fourth frequencies,
wherein the third and fourth frequencies are formed due to interaction of the first signal from the first acoustic marker with the Doppler signal transmitted by an ultrasound imaging transducer.

17. The method of claim 16, wherein the third and fourth signals have frequencies f3 and f4, respectively, and the third signal frequency is equal to the first signal frequency, f1, added to the Doppler imaging signal frequency, fD, such that f3=fD+f1 and the fourth signal frequency is equal to the first signal frequency subtracted from the Doppler imaging signal frequency such that f4=fD−f1.

18. The method of claim 17, wherein the interference signals of frequencies f3 and f4 are processed as identification Doppler shifts in pulsed-wave Doppler scans and color markers in color Doppler scans.

19. The method of claim 16, further comprising navigating a catheter tip and contacting an anatomic target with the catheter tip.

20. The method of claim 16, further comprising the alternating acoustic communication steps of:
transmitting the second signal having a second frequency f2 by the first acoustic marker while the second acoustic marker is receiving that signal; and
transmitting the second signal with the second acoustic marker while the first acoustic marker is receiving that signal.

21. The method of claim 20, wherein the acoustic communication alternates in transmission between the first and second acoustic markers to allow for measurement of the needle exposure length.

22. The method of claim 16, further comprising penetrating an anatomic target with the needle.

23. The method of claim 21, further comprising the step of obtaining a measurement of the needle insertion depth within the anatomic target.

24. The method of claim 22, further comprising changing the measured needle exposure length.

25. The method of claim 23, further comprising inserting the needle to a desired depth within the anatomic target.

26. The method of claim 24, comprising injecting an investigative or therapeutic agent via the inserted needle into the desired depth within the anatomic target.

27. A system, comprising:
    an injection catheter, the injection catheter comprising:
        an outer tube comprising a first lumen;
        an inner tube disposed within the first lumen of the outer tube, the inner tube comprising a second lumen;
        a needle slidably disposed within the second lumen of the inner tube;
        a first acoustic marker coupled to the injection catheter at a location proximate to a distal end of the injection catheter and configured to generate a first acoustic signal;
        a second acoustic marker coupled to the needle at a location proximate to the distal end of the needle and configured to generate a second acoustic signal; and
    a sonometry system configured to measure an exposure length of the needle based on acoustic communication between the first and second acoustic markers, and wherein the sonometry system is configured to measure the exposure length of the needle based on measuring a time delay between at least one of:
    generating the first acoustic signal with the first acoustic marker and receiving the first acoustic signal with the second acoustic marker, or
    generating the second acoustic signal with the second acoustic marker and receiving the second acoustic signal with the first acoustic marker.

28. The system of claim 27, wherein the first and second acoustic markers include piezoelectric crystals.

29. The system of claim 28, wherein the piezoelectric crystals are made of lead zirconate titanate or polyvinylidene fluoride.

30. The system of claim 27, further comprising a first electrical wiring in electrical communication with the first acoustic marker.

31. The system of claim 27, further comprising a second electrical wiring in electrical communication with the second acoustic marker.

32. The system of claim 27, further comprising:
    a waveform generator electrically connected to at least one of the first acoustic marker or the second acoustic marker and wherein the at least one of the first acoustic marker or the second acoustic marker is configured to generate an acoustic signal in response to electrical input received from the waveform generator.

33. The system of claim 27 further comprising an ultrasound system electrically connected to at least one of the first acoustic marker or the second acoustic marker and wherein said acoustic marker is configured to generate an acoustic signal in response to electrical input received from the ultrasound system.

* * * * *

UNITED STATES PATENT AND TRADEMARK OFFICE
CERTIFICATE OF CORRECTION

PATENT NO. : 11,123,141 B2  
APPLICATION NO. : 15/136064  
DATED : September 21, 2021  
INVENTOR(S) : Marek Belohlavek et al.

Page 1 of 1

It is certified that error appears in the above-identified patent and that said Letters Patent is hereby corrected as shown below:

In the Claims

Column 30, Claim 15, Line 12, "AAC" should be --catheter--.

Signed and Sealed this  
Eighth Day of March, 2022

Drew Hirshfeld  
*Performing the Functions and Duties of the*  
*Under Secretary of Commerce for Intellectual Property and*  
*Director of the United States Patent and Trademark Office*